United States Patent
Woster et al.

(10) Patent No.: US 10,118,903 B2
(45) Date of Patent: Nov. 6, 2018

(54) AMINOTRIAZOLE-BASED KDM1A INHIBITORS AS EPIGENETIC MODULATORS

(71) Applicant: MUSC FOUNDATION FOR RESEARCH DEVELOPMENT, Charleston, SC (US)

(72) Inventors: Patrick M. Woster, Charleston, SC (US); Craig J. Kutz, Johns Island, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days.

(21) Appl. No.: 15/115,342

(22) PCT Filed: Feb. 6, 2015

(86) PCT No.: PCT/US2015/014830
§ 371 (c)(1),
(2) Date: Jul. 29, 2016

(87) PCT Pub. No.: WO2015/120281
PCT Pub. Date: Aug. 13, 2015

(65) Prior Publication Data
US 2017/0001968 A1  Jan. 5, 2017

Related U.S. Application Data

(60) Provisional application No. 61/937,034, filed on Feb. 7, 2014.

(51) Int. Cl.
*C07D 249/14* (2006.01)
*C07D 257/06* (2006.01)
*C07D 403/12* (2006.01)
*C07D 405/12* (2006.01)

(52) U.S. Cl.
CPC ......... *C07D 249/14* (2013.01); *C07D 257/06* (2013.01); *C07D 403/12* (2013.01); *C07D 405/12* (2013.01)

(58) Field of Classification Search
None
See application file for complete search history.

(56) References Cited

U.S. PATENT DOCUMENTS

2007/0112006 A1* 5/2007 Schiemann ........ C07D 231/38
514/246

FOREIGN PATENT DOCUMENTS

WO  WO 2010/084160  7/2010
WO  WO 2011/131697  10/2011

OTHER PUBLICATIONS

Ito et al. in Cancer Science 94(1), 3-8 (2003).*
STN Registry database entry for CAS RN 1275231-67-8 (Entered STN Apr. 5, 2011), Accessed Jul. 2, 2017.*
Culhane, et al., "A mechanism-based inactivator for histone demethylase LSD1," *J. Am. Chem. Soc.*, 128(14):4536-4537, 2006.
Culhane, et al., "Comparative analysis of small molecules and histone substrate analogues as LSD1 lysine demethylase inhibitors," *J. Am. Chem. Soc.*, 132(9):3164-3176, 2010.
Duan, et al., "Design and synthesis of novel 1, 2,3-triazole-dithiocarbamate hybrids as potential anticancer agents," *Eur. J. Med. Chem.*, 62, 11-19, 2013.
Duan, et al., "Design, synthesis and antiproliferative activity studies of novel 1, 2,3-triazole-dithiocarbamate-urea hybrids," *Eur. J. Med. Chem.*, 64:99-110, 2013.
Forneris, et al., "Structural basis of LSD1-CoREST selectivity in histone H3 recognition," *J. Biol. Chem.*, 282(28):20070-20074, 2007.
Sharma, et al., "(Bis)urea and (bis)thiourea inhibitors of lysine-specific demethylase 1 as epigenetic modulators," *J. Med. Chem.*, 53(14):5197-5212, 2010.

(Continued)

*Primary Examiner* — Alicia L Otton
(74) *Attorney, Agent, or Firm* — Parker Highlander PLLC

(57) ABSTRACT

In some aspects, the present invention provides compounds of the formula (IV), wherein the variables are as defined herein, which may be used as inhibitors of histone demethylase or spermine oxidase. Also provided herein are pharmaceutical compositions of the compounds and methods using the compounds in the treatment of diseases such as cancer and cardiovascular disease.

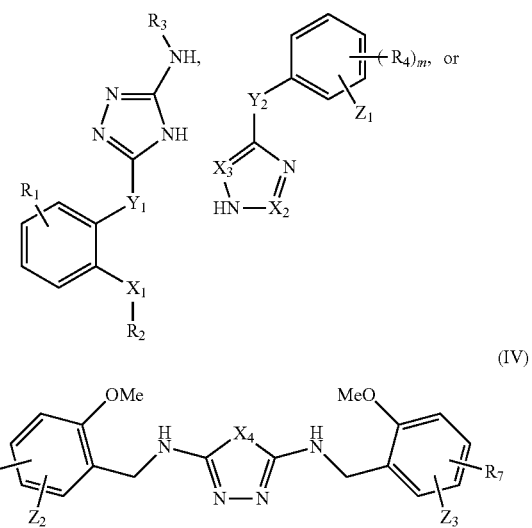

18 Claims, 11 Drawing Sheets
Specification includes a Sequence Listing.

(56) References Cited

OTHER PUBLICATIONS

Sharma, et al., "Polyamine-based small molecule epigenetic modulators," *MedChemComm*, 3:14-21, 2012.

Szewczuk, et al., "Mechanistic analysis of a suicide inactivator of histone demethylase LSD1." *Biochemistry*, 46(23):6892-6902, 2007.

Yang, et al., "Structural basis of histone demethylation by LSD1 revealed by suicide inactivation." *Nat. Struct. Mol. Biol.*, 14(6):535-539, 2007.

Zheng, et. al., "Triazole-dithiocarbamate based selective lysine specific demethylase 1 (LSD1) inactivators inhibit gastric cancer cell growth, invasion, and migration," *J. Med. Chem.*, 56(21):8543-60, 2013.

National Center for Biotechnology Information. PubChem Compound Database; CID=3613730, https://pubchem.ncbi.nlm.nih.gov/compound/3613730 (accessed Jan. 3, 2017).

PCT Search Report and Written Opinion for PCT/US2015/014830, dated Jul. 20, 2015.

Sorna, V., et al., "High-throughput virtual screening identifies novel N'-(1-phenylethylidene)-benzohydrazides as potent, specific, and reversible LSD1 inhibitors." *J Med Chem*, 23: 9496-508, 2013.

Hitchin, J. R., et al., "Development and evaluation of selective, reversible LSD1 inhibitors derived from fragments." *MedChemComm*, 4: 1513-1522, 2013.

Zheng, Y. C., et al., "Triazole-Dithiocarbamate Based Selective Lysine Specific Demethylase 1 (LSD1) Inactivators Inhibit Gastric Cancer Cell Growth, Invasion, and Migration." *J. Med. Chem.*, 56: 8543-8560, 2013.

Kutz, C. J.; Holshouser, S. L.; Marrow, E. A.; Woster, P. M., "3,5-Diamino-1,2,4-triazoles as a novel scaffold for potent, reversible LSD1 (KDM1A) inhibitors." *MedChemComm*, 5 (12): 1863-1870, 2014.

Fiskus, W. et al., "Highly effective combination of LSD1 (KDM1A) antagonist and pan-histone deacetylase inhibitor against human AML cells.", 28 (11): 2155-64, 2014.

Schmitt, M. L. et al., "Nonpeptidic Propargylamines as Inhibitors of Lysine Specific Demethylase 1 (LSD1) with Cellular Activity." *J Med Chem*, 56 (18): 7334-42, 2013.

Willmann, D. et al., "Impairment of prostate cancer cell growth by a selective and reversible lysine-specific demethylase 1 inhibitor." *Int J Cancer*, 131 (11): 2704-9, 2012.

Dulla, B., et al., "Synthesis and evaluation of 3-amino/guanidine substituted phenyl oxazoles as a novel class of LSD1 inhibitors with anti-proliferative properties." *Organic & biomolecular chemistry*, 11 (19): 3103-7, 2013.

Hazeldine, S., et al., "Low molecular weight amidoximes that act as potent inhibitors of lysine-specific demethylase 1." *J Med Chem*, 55 (17): 7378-91, 2012.

* cited by examiner

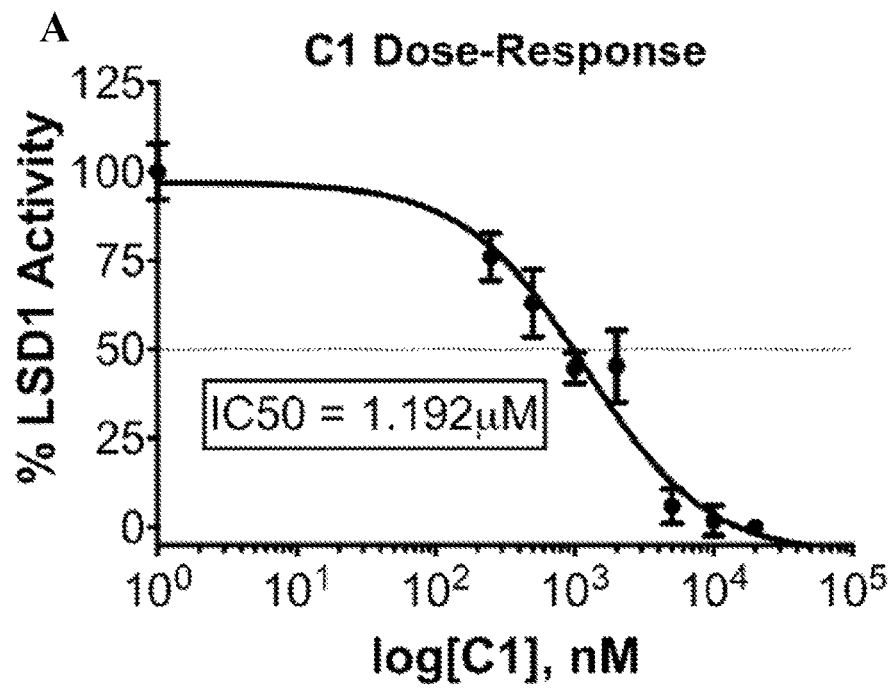
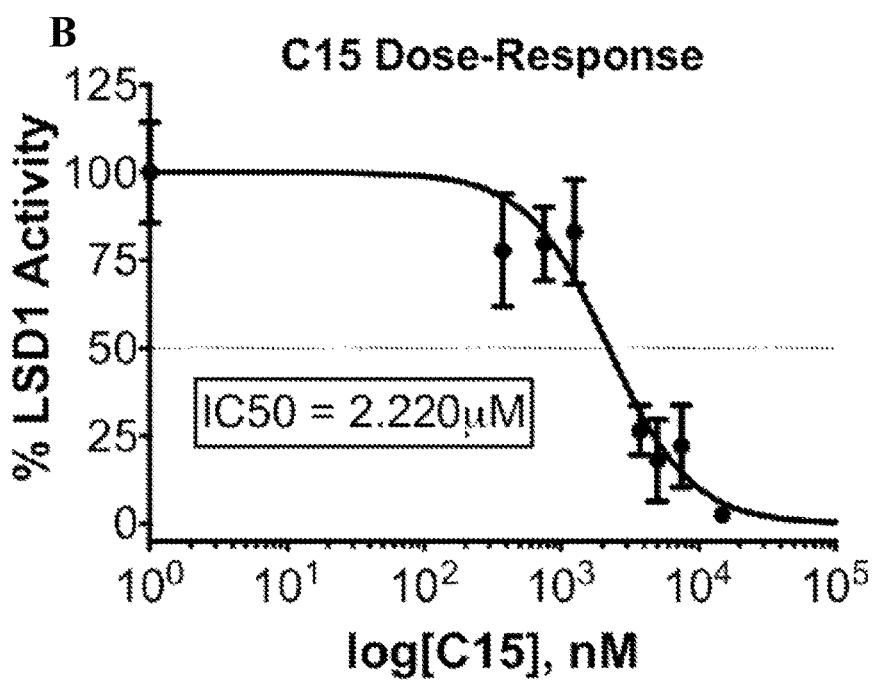
FIG. 3a-b

SEQUENCE LISTING

<160> NUMBER OF SEQ ID NOS: 1

<210> SEQ ID NO 1
<211> LENGTH: 21

```
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (4)..(4)
<223> OTHER INFORMATION: dimethylated lysine

<400> SEQUENCE: 1

Ala Arg Thr Lys Gln Thr Ala Arg Lys Ser Thr Gly Gly Lys Ala Pro
1               5                   10                  15

Arg Lys Gln Leu Ala
            20
```

AMINOTRIAZOLE-BASED KDM1A INHIBITORS AS EPIGENETIC MODULATORS

This application is a national phase application under 35 U.S.C. § 371 of International Application No. PCT/US2015/014830, filed Feb. 6, 2015, which claims the benefit of U.S. Provisional Application No. 61/937,034, filed on Feb. 7, 2014, the entirety of each of which are incorporated herein by reference.

This invention was made with Government support under Grant No. RO1 CA149095 awarded by the National Institutes of Health and Grant No. TL1 TR000061 funded by the NIH National Center for Advancing Translational Sciences. The Government has certain rights in the invention.

Pursuant to 37 C.F.R. 1.821(c), a sequence listing is submitted herewith as an ASCII compliant text file named "MESCP0082US_ST25.txt", created on Jul. 26, 2016 and having a size of ~1 kilobytes. The content of the aforementioned file is hereby incorporated by reference in its entirety.

BACKGROUND OF THE INVENTION

I. Field of the Invention

The present invention relates generally to the fields of biology and medicine. More particularly, it concerns compounds, compositions and methods for the treatment and prevention of diseases such as those associated with oxidative stress and inflammation.

II. Description of Related Art

There are numerous lysine methylation sites on histone tails, and post-translational modifications at specific lysine marks can promote transcriptional activation or silencing. Histone 3 lysine 4 (H3K4) is a transcription-activating chromatin mark at gene promoters, and demethylation of this mark by LSD1 may prevent expression of tumor suppressor genes important in human cancer (Huang, et al., 2007). Because LSD1 is overexpressed in a number of human cancers (neuroblastoma, retinoblastoma, prostate cancer, breast cancer, lung cancer and bladder cancer), (Hayami, et al., 2011; Lim, et al., 2010; Schulte, et al., 2009; Rotili and Mai, 2011) the enzyme has emerged as an important target for the development of specific inhibitors as a new class of antitumor drugs (Stavropoulos and Hoelz, 2007).

To date, a handful of small molecule inhibitors of LSD1 have been described (FIG. 1). Effective LSD1 inhibitors include tranylcypromine-based analogues such as 1 and 2 (WO 2010/084160 and WO 2011/131697), oligoamines such as verlindamycin (aka 2d) 34 and related isosteric ureas and thioureas, (Sharma, et al., 2010; Sharma, et al., 2012) and peptide based LSD1 inhibitors 4 and 5 (Culhane, et al., 2006; Culhane, et al., 2010; Szewczuk, et al., 2007; Yang, et al., 2007). Forneris et al., 2007 described a 21-mer peptide analogous to the histone 3 lysine 4 substrate region of LSD1, wherein Lys4 was replaced by a methionine (compound 6, FIG. 1), which acts as a competitive inhibitor. This linear peptide was a potent inhibitor of recombinant LSD1 with a Ki value of 0.04 mM, and of LSD1 bound to CoREST with a $K_i$ value of 0.05 mM (Forneris, et al., 2007). Unfortunately, most of the available inhibitors are based on the tranylcypromine scaffold, and thus there is a potential for undesired off-target effects mediated by monoamine oxidase and other flavin-dependent amine oxidases. In addition, inhibitors based on a linear peptide backbone are susceptible to hydrolysis and difficult to deliver. Additionally, several triazole LSD1 inhibitors have been described in the literature but rely on the dithiocarbamate moiety of the compound rather than the heteroaryl group for their pharmalogical activity (Duan, et al., 2013a; Duan, et al., 2013b; Zheng, et al., 2013). Furthermore, these compounds act by inactivating the enzyme rather than reversible competitive inhibitors for the enzyme's natural substrate. Additionally, LSD1 forms several catalytically active complexes which are implicated in many other disease states such as cardiovascular disease. As such, new inhibitors of LSD1 would be beneficial, including for the treatment of cancer, cardiac disease, and other diseases or disorders.

SUMMARY OF THE INVENTION

The present disclosure provides novel compounds which maybe used to inhibit the demethylase LSD1 and as therapeutic agents for diseases and disorders associated with misregulation of LSD1.

In one aspect, the present invention provides a compound of the formula:

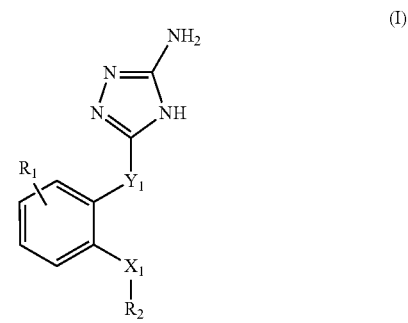

wherein: $R_1$ is hydrogen, halo, hydroxy, amino, nitro, cyano, alkyl$_{(C \leq 12)}$, or substituted alkyl$_{(C \leq 12)}$; $Y_1$ is alkanediyl$_{(C \leq 12)}$, alkylaminodiyl$_{(C \leq 12)}$, alkoxydiyl$_{(C \leq 12)}$, or a substituted version of any of these groups; $X_1$ is —O—, —S—, or —NR$_3$—, wherein $R_3$ is hydrogen or alkyl$_{(C \leq 6)}$; and $R_2$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; provided that $R_2$ is not phenyl when $X_1$ is —O—; or a pharmaceutically acceptable salt or tautomer thereof. In some embodiments, the formula is further defined as:

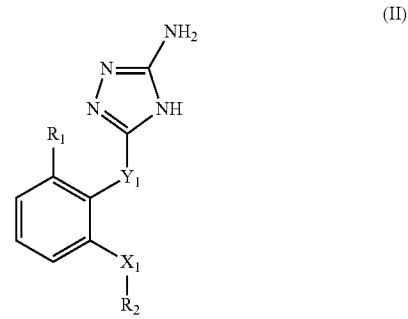

wherein: $R_1$ is hydrogen, halo, hydroxy, amino, nitro, cyano, alkyl$_{(C \leq 12)}$, or substituted alkyl$_{(C \leq 12)}$; $Y_1$ is alkanediyl$_{(C \leq 12)}$, alkylaminodiyl$_{(C \leq 12)}$, alkoxydiyl$_{(C \leq 12)}$, or a substituted version of any of these groups; $X_1$ is —O—, —S—, or —NR$_3$—, wherein $R_3$ is hydrogen or alkyl$_{(C≤6)}$; $R_2$ is alkyl$_{(C≤12)}$, aryl$_{(C≤12)}$, aralkyl$_{(C≤12)}$, heteroaryl$_{(C≤12)}$, heteroaralkyl$_{(C≤12)}$, or a substituted version of any of these groups; provided that $R_2$ is not phenyl when $X_1$ is —O—; or a pharmaceutically acceptable salt of tautomer thereof. In some embodiments, $R_1$ is hydrogen. In other embodiments, $R_1$ is halo. In some embodiments, $R_1$ is —Br or —Cl. In some embodiments, $R_1$ is —Cl. In some embodiments, $Y_1$ is alkylaminodiyl$_{(C≤12)}$. In some embodiments, $Y_1$ is —CH$_2$NH— or —NHCH$_2$—. In some embodiments, $X_1$ is —O—, —S—, or —NH—. In some embodiments, $X_1$ is —O—. In other embodiments, $X_1$ is —S—. In some embodiments, $R_2$ is alkyl$_{(C≤12)}$ or substituted alkyl$_{(C≤12)}$. In some embodiments, $R_2$ is alkyl$_{(C≤12)}$. In some embodiments, $R_2$ is methyl. In other embodiments, $R_2$ is aryl$_{(C≤12)}$ or substituted aryl$_{(C≤12)}$. In some embodiments, $R_2$ is aryl$_{(C≤12)}$. In some embodiments, $R_2$ is 1-napthyl, 2-napthyl, 4,4'-diphenyl, 4-methylphenyl, 3,5-dimethylphenyl, 4-t-butylphenyl, 2-isopropyl-4-methylphenyl, 2-methylphenyl, or 2,3-dimethylphenyl. In other embodiments, $R_2$ is substituted aryl$_{(C≤12)}$. In some embodiments, $R_2$ is 4-fluorophenyl, 2-methoxyphenyl, 3-methoxyphenyl, 4-methylthiophenyl, 4-trifluoromethyloxyphenyl, 4-trifluoromethylthiophenyl, 2,4-dibromophenyl, 3,4-dimethoxyphenyl, 3,5-dimethoxyphenyl, 3,5-trifluoromethylphenyl, 3,4,5-trimethoxyphenyl, 2-ethoxy-4-methylphenyl, 4-bromo-2-trifluoromethylphenyl, 2-methoxy-4-methylphenyl, or

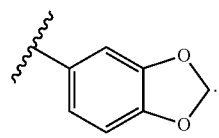 [SMILES: *c1ccc2c(c1)OCO2]

In other embodiments, $R_2$ is heteroaryl$_{(C≤12)}$ or substituted heteroaryl$_{(C≤12)}$. In some embodiments, $R_2$ is heteroaryl$_{(C≤12)}$. In some embodiments, $R_2$ is indolyl. In some embodiments, the formula is selected from:

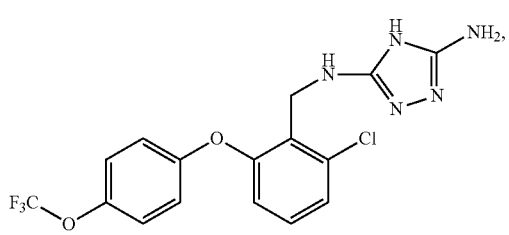

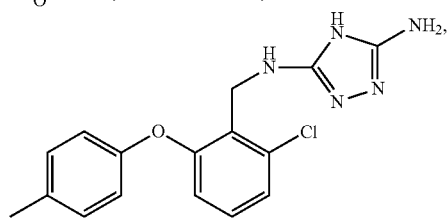

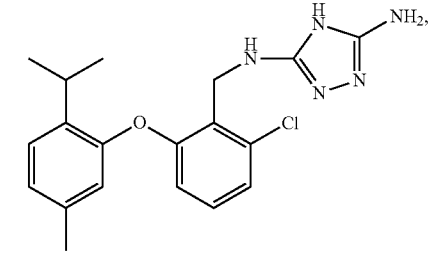

-continued

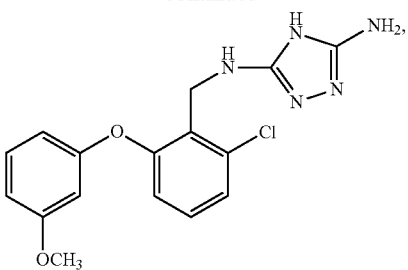

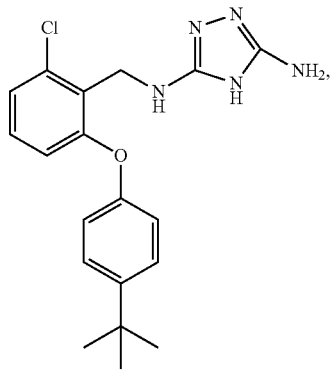

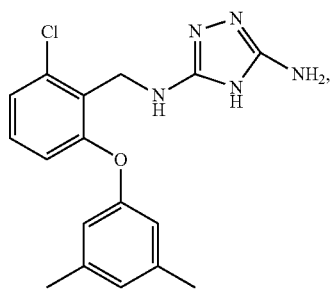

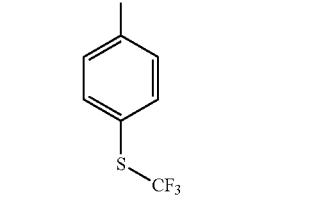

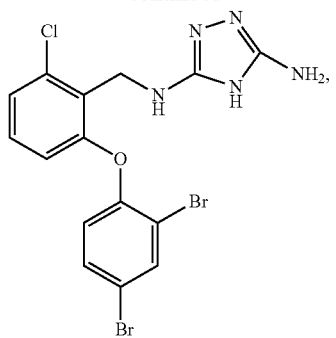
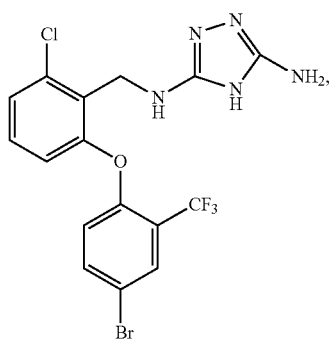
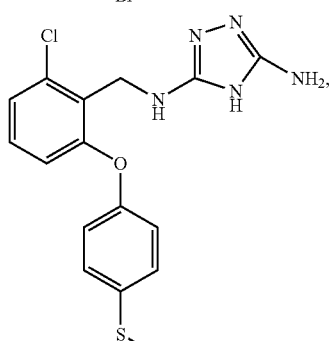
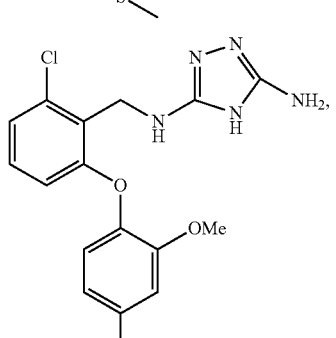
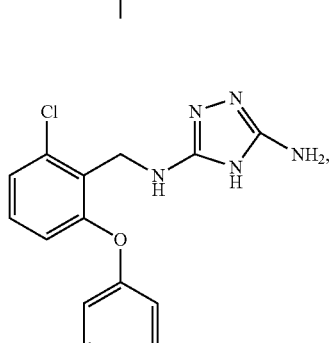
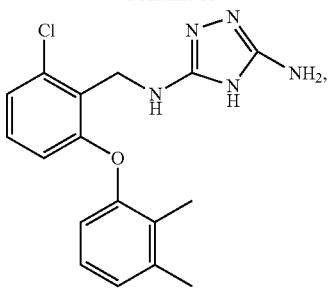
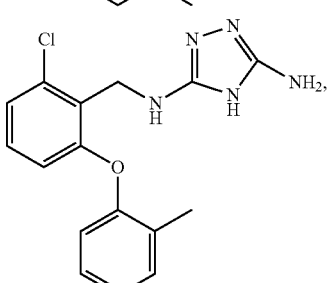
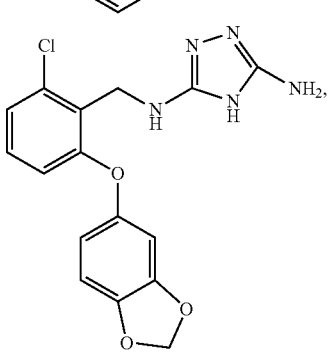
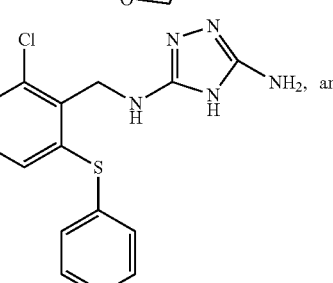
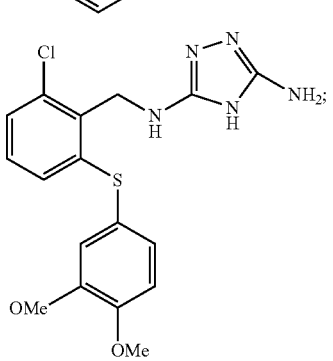
or a pharmaceutically acceptable salt thereof. In another aspect the present invention relates to a compound of the formula:

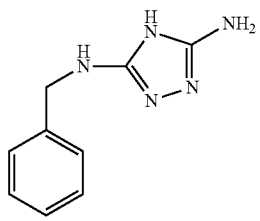 [SMILES: Nc1nnc(NCc2ccccc2)[nH]1]

or a pharmaceutically acceptable salt thereof.

In yet another aspect, the present invention provides a composition comprising a compound of the present disclosure and an excipient. In some embodiments, the pharmaceutical composition is formulated for oral, intraadiposal, intraarterial, intraarticular, intracranial, intradermal, intralesional, intramuscular, intranasal, intraocular, intrapericardial, intraperitoneal, intrapleural, intraprostatical, intrarectal, intrathecal, intratracheal, intratumoral, intraumbilical, intravaginal, intravenous, intravesicularl, intravitreal, liposomal, local, mucosal, parenteral, rectal, subconjunctival, subcutaneous, sublingual, topical, transbuccal, transdermal, vaginal, via a catheter, via a lavage, via continuous infusion, via infusion, via inhalation, via injection, via local delivery, or via localized perfusion administration. In some embodiments, the pharmaceutical composition is formulated for oral, intraarterial, intraarticular, intradermal, intravenous, local, or topical administration.

In another aspect, the present disclosure provides a method of treating a disease or disorder comprising administering to a patient a therapeutically effective amount of a compound of the formula:

(I)

wherein: $R_1$ is hydrogen, halo, hydroxy, amino, nitro, cyano, alkyl$_{(C\leq12)}$, or substituted alkyl$_{(C\leq12)}$; $Y_1$ is alkanediyl$_{(C\leq12)}$, alkylaminodiyl$_{(C\leq12)}$, alkoxydiyl$_{(C\leq12)}$, or a substituted version of any of these groups; $X_1$ is —O—, —S—, or —NR—, wherein $R_3$ is hydrogen or alkyl$_{(C\leq6)}$; $R_2$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_3$ is hydrogen, hydroxy, alkyl$_{(C\leq12)}$, substituted alkyl$_{(C\leq12)}$, alkoxy$_{(C\leq12)}$, or substituted alkoxy$_{(C\leq12)}$; or

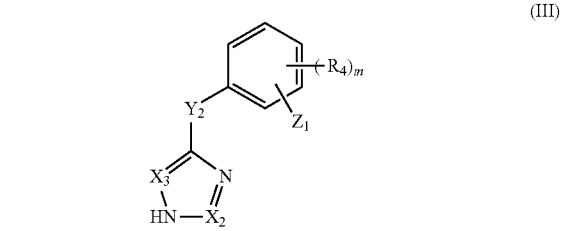

$R_4$ is each independently hydrogen, hydroxy, halo, nitro, or cyano, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, or a substituted version of any of these groups; m is 0, 1, 2, 3, or 4; $X_2$ and $X_3$ are each independently $CR_5$ or N; wherein: $R_5$ is hydrogen, amino, alkyl$_{(C\leq12)}$, substituted alkyl$_{(C\leq12)}$, alkylamino$_{(C\leq12)}$, substituted alkylamino$_{(C\leq12)}$, aryl$_{(C\leq12)}$, substituted aryl$_{(C\leq12)}$, aralkyl$_{(C\leq12)}$, substituted aralkyl$_{(C\leq12)}$, aralkylamino$_{(C\leq12)}$, substituted aralkylamino$_{(C\leq12)}$, alkoxy$_{(C\leq12)}$, or substituted alkoxy$_{(C\leq12)}$; $Y_2$ is alkanediyl$_{(C\leq12)}$, alkylaminodiyl$_{(C\leq12)}$, alkoxydiyl$_{(C\leq12)}$, or a substituted version of any of these groups; and $Z_1$ is halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or

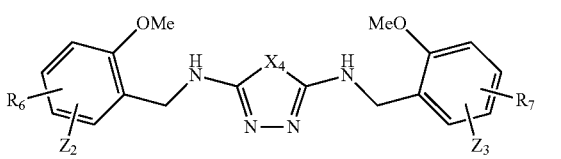

$R_6$ and $R_7$ are each independently hydrogen, hydroxy, halo, nitro, cyano, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; $X_4$ is —$CR_8R_{8'}$—, —$NR_8$—, —O—, or S; wherein: $R_8$ and $R_{8'}$ are each independently hydrogen, alkyl$_{(C\leq12)}$, or substituted alkyl$_{(C\leq12)}$; and $Z_4$ and $Z_5$ are each independently hydrogen, halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or

or a pharmaceutically acceptable salt or tautomer, thereof. In some embodiments, the formula is formula I. In other embodiments, the formula is formula III. In other embodiments, the formula is formula IV. In some embodiments, $R_1$ is hydrogen. In other embodiments, $R_1$ is halo. In some embodiments, $R_1$ is —Br or —Cl. In some embodiments, $R_1$ is —Cl. In some embodiments, $Y_1$ is alkylaminodiyl$_{(C≤12)}$. In some embodiments, $Y_1$ is —CH$_2$NH— or —NHCH$_2$—. In some embodiments, $X_1$ is —O—, —S—, or —NH—. In some embodiments, $X_1$ is —O—. In other embodiments, $X_1$ is —S—. In some embodiments, $R_2$ is alkyl$_{(C≤12)}$ or substituted alkyl$_{(C≤12)}$. In some embodiments, $R_2$ is alkyl$_{(C≤12)}$. In some embodiments, $R_2$ is methyl. In other embodiments, $R_2$ is aryl$_{(C≤12)}$ or substituted aryl$_{(C≤12)}$. In some embodiments, $R_2$ is aryl$_{(C≤12)}$. In some embodiments, $R_2$ is 1-napthyl, 2-napthyl, 4,4'-diphenyl, 4-methylphenyl, 3,5-dimethylphenyl, 4-t-butylphenyl, 2-isopropyl-4-methylphenyl, 2-methylphenyl, or 2,3-dimethylphenyl. In other embodiments, $R_2$ is substituted aryl$_{(C≤12)}$. In some embodiments, $R_2$ is 4-fluorophenyl, 2-methoxyphenyl, 3-methoxyphenyl, 4-methylthiophenyl, 4-trifluoromethyloxyphenyl, 4-trifluoromethylthiophenyl, 2,4-dibromophenyl, 3,5-dimethoxyphenyl, 3,5-trifluoromethylphenyl, 3,4,5-trimethoxyphenyl, 2-ethoxy-4-methylphenyl, 4-bromo-2-trifluoromethylphenyl, 2-methoxy-4-methylphenyl, or

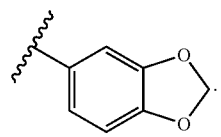 [SMILES: *c1ccc2c(c1)OCO2]

In other embodiments, $R_2$ is heteroaryl$_{(C≤12)}$ or substituted heteroaryl$_{(C≤12)}$. In some embodiments, $R_2$ is heteroaryl$_{(C≤12)}$. In some embodiments, $R_2$ is indolyl. In some embodiments, $X_2$ is CH. In other embodiments, $X_2$ is N. In some embodiments, $X_3$ is CH. In other embodiments, $X_3$ is N. In some embodiments, $Y_2$ is alkylaminodiyl$_{(C≤12)}$. In some embodiments, $Y_2$ is —CH$_2$NH— or —NHCH$_2$—. In some embodiments, m is 0 or 1. In some embodiments, $Z_1$ is halo. In some embodiments, $Z_1$ is —Br, —Cl, or —F. In some embodiments, $Z_1$ is —Cl. In other embodiments, $Z_1$ is alkoxy$_{(C≤12)}$ or substituted alkoxy$_{(C≤12)}$. In some embodiments, $Z_1$ is alkoxy$_{(C≤12)}$. In some embodiments, $Z_1$ is methoxy or ethoxy. In other embodiments, $Z_1$ is aralkoxy$_{(C≤12)}$ or substituted aralkoxy$_{(C≤12)}$. In some embodiments, $Z_1$ is aralkoxy$_{(C≤12)}$. In some embodiments, $Z_1$ is benzyloxy or 4-methylphenylmethoxy. In other embodiments, $Z_1$ is substituted aralkoxy$_{(C≤12)}$. In some embodiments, $Z_1$ is 4-fluorophenylmethoxy, 2-fluorophenylmethoxy, 2-chloro-4-fluorophenylmethoxy, or 2-chlorophenylmethoxy. In some embodiments, $R_4$ is halo. In some embodiments, $R_4$ is —Br, —Cl, or —F. In some embodiments, $R_4$ is —Cl. In other embodiments, $R_4$ is hydrogen. In other embodiments, $R_4$ is alkoxy$_{(C≤12)}$ or substituted alkoxy$_{(C≤12)}$. In some embodiments, $R_4$ is methoxy or ethoxy. In some embodiments, $X_4$ is —NR$_8$— wherein $R_8$ is hydrogen, alkyl$_{(C≤12)}$, or substituted alkyl$_{(C≤12)}$. In some embodiments, $X_4$ is —NH—. In some embodiments, $R_6$ is hydrogen. In some embodiments, $R_7$ is hydrogen. In some embodiments, $R_6$ and $R_7$ are hydrogen. In some embodiments, $Z_2$ is hydrogen. In some embodiments, $Z_3$ is hydrogen. In some embodiments, $Z_2$ and $Z_3$ are hydrogen. In some embodiments, the compound is selected from:

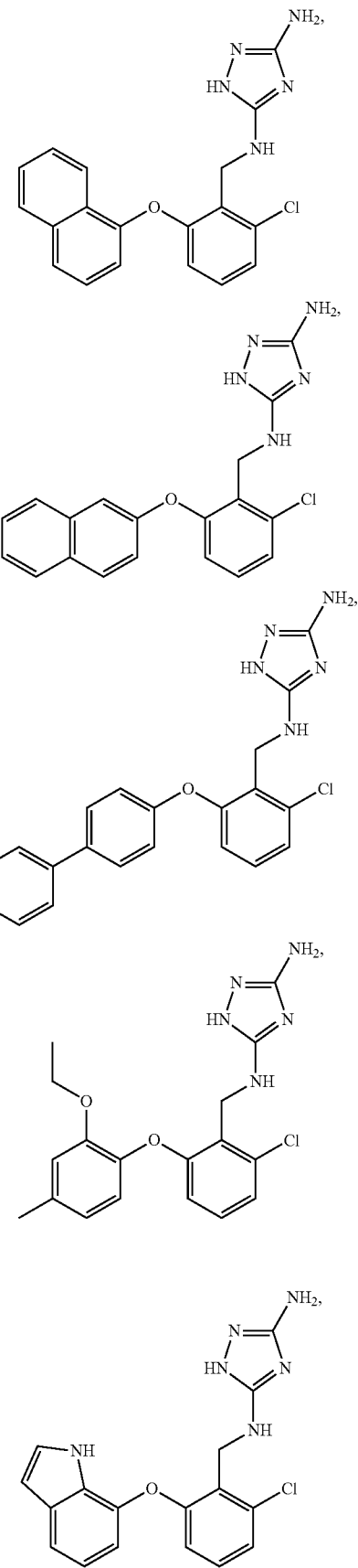

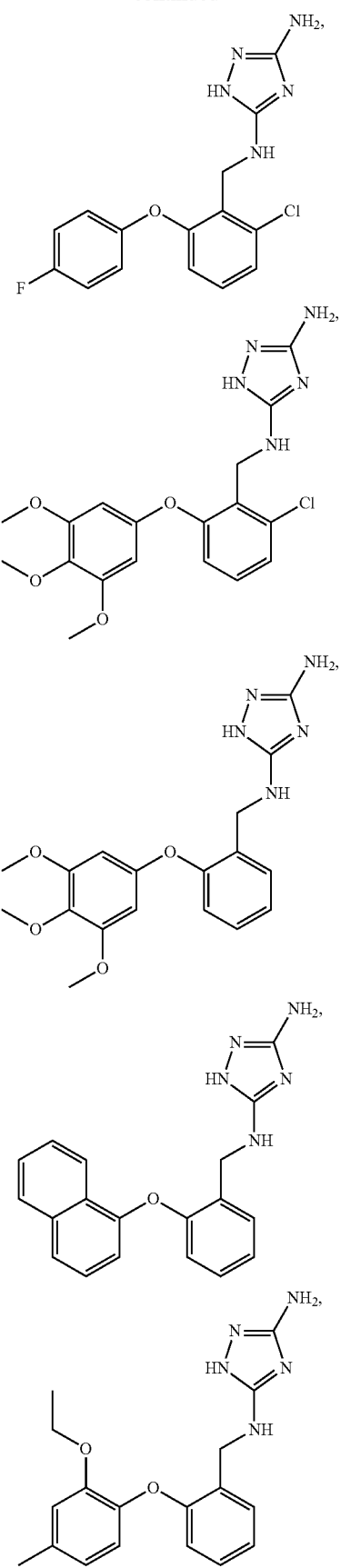 [SMILES: Nc1n[nH]c(NCc2c(Cl)cccc2Oc2ccc(F)cc2)n1 ; COc1cc(Oc2cccc(Cl)c2CNc2nc(N)n[nH]2)cc(OC)c1OC ; COc1cc(Oc2ccccc2CNc2nc(N)n[nH]2)cc(OC)c1OC ; Nc1n[nH]c(NCc2ccccc2Oc2cccc3ccccc23)n1 ; CCOc1cc(C)ccc1Oc1ccccc1CNc1nc(N)n[nH]1]
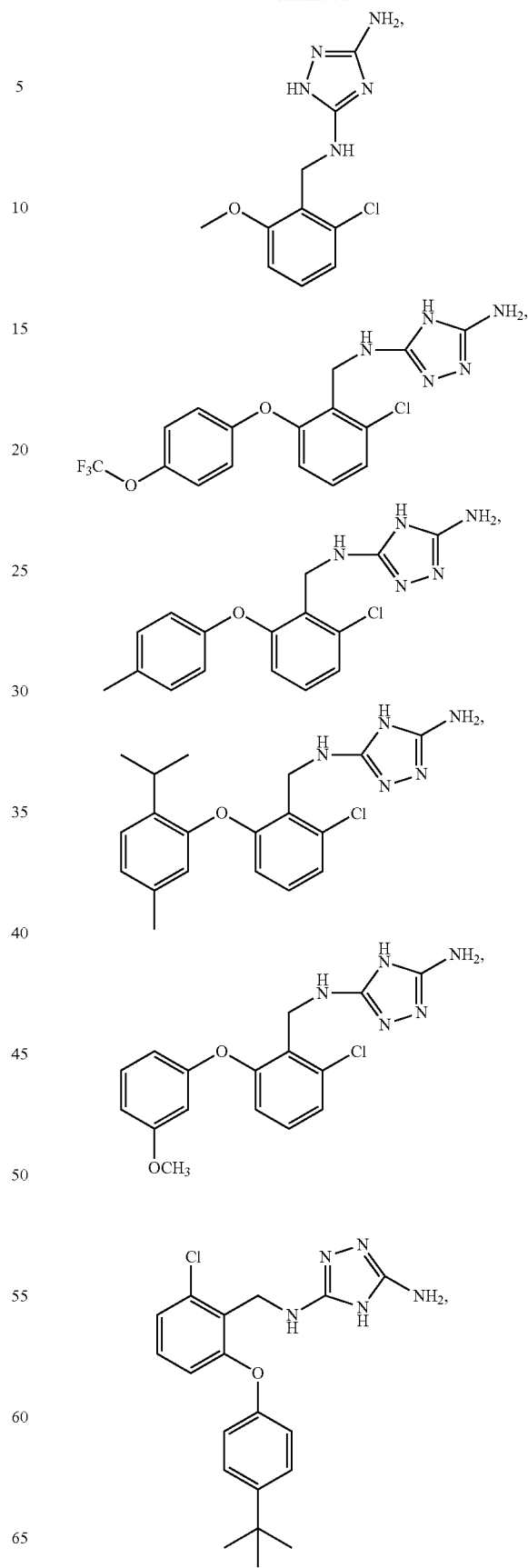

-continued
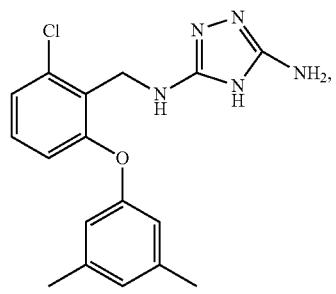
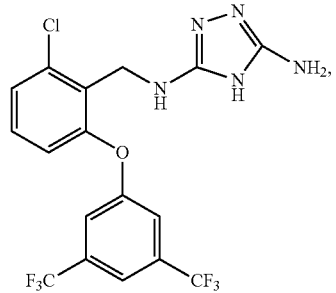
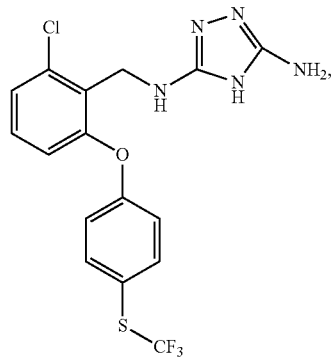
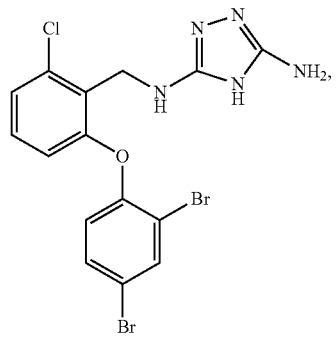
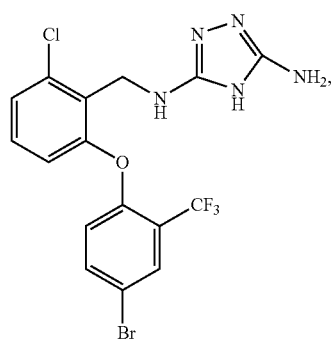
-continued
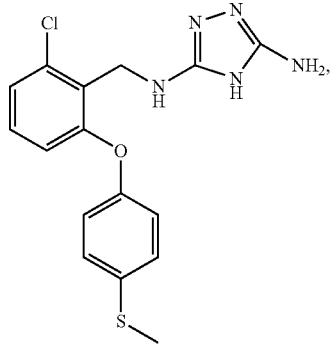
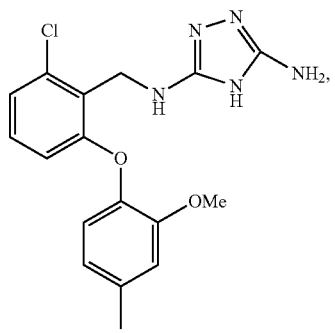
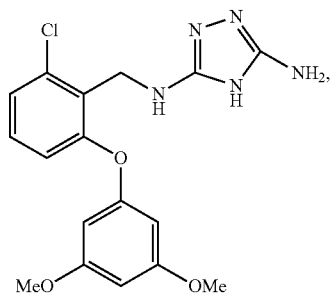
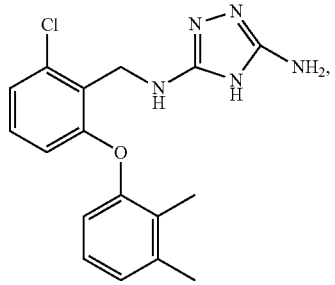
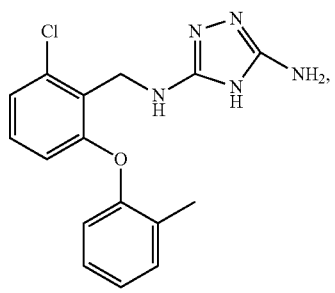

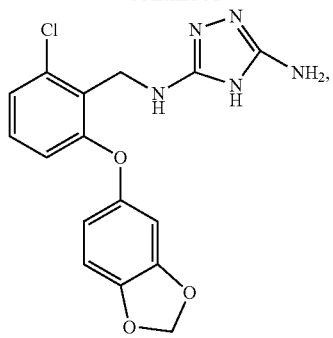
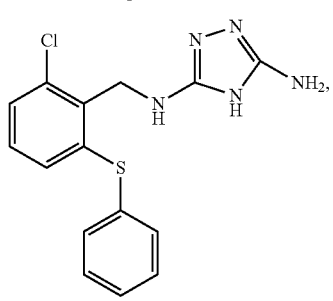
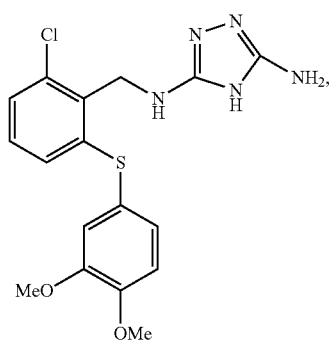
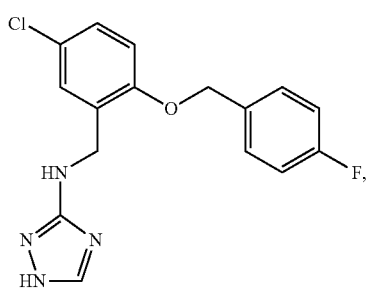
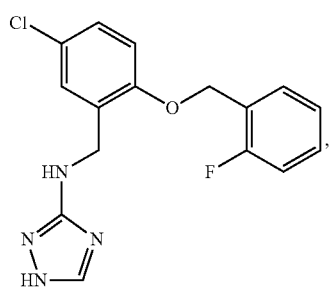
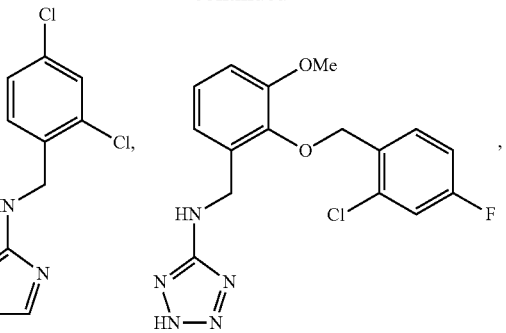
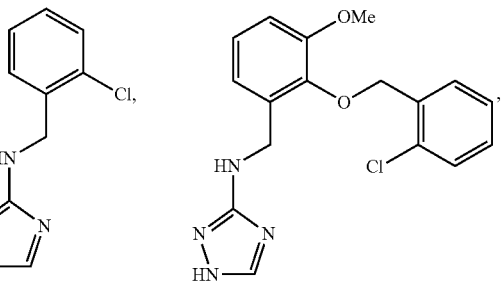
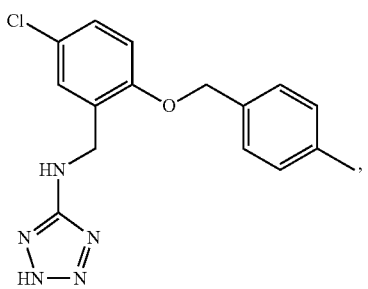
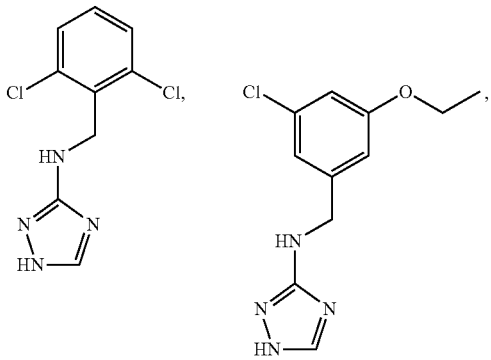
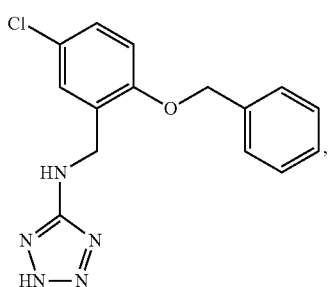

-continued

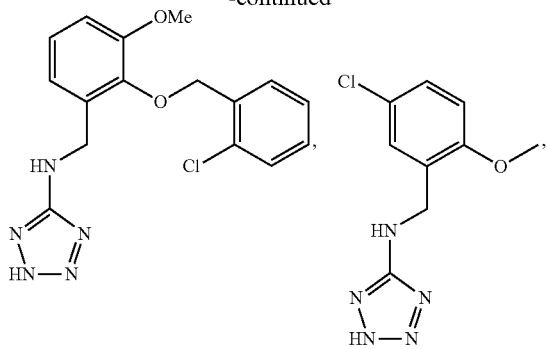

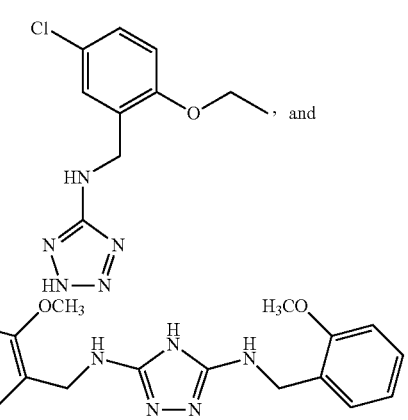

or a pharmaceutically acceptable salt or tautomer, thereof. In some embodiments, the disease is cancer. In some embodiments, the cancer is of the bladder, blood, bone, brain, breast, central nervous system, cervix, colon, eyes, endometrium, esophagus, gall bladder, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In other embodiments, the cancer is a carcinoma, sarcoma, leukemia, melanoma, mesothelioma, multiple myeloma, or seminoma. In some embodiments, the cancer is neuroblastoma, retinoblastoma, prostate cancer, breast cancer, lung cancer, gastric cancer, or bladder cancer. In some embodiments, the gastric cancer develops after an *H. pylori* infection. In some embodiments, the *H. pylori* infection is a chronic infection. In other embodiments, the disease is cardiac disease. In some embodiments, the cardiac disease is caused by an ischemic event. In some embodiments, the disease is a cardiac reperfusion injury. In some embodiments, the disease is heart failure. In some embodiments, the administration reduces an infarct area caused by a cardiac reperfusion injury relative to an untreated patient. In some embodiments, the administration protects from cardiac reperfusion injury by restoring normal ventricular developed pressure. In some embodiments, the patient is a mammal. In some embodiments, the patient is a human.

In yet another aspect, the present disclosure provides a method of inhibiting an enzyme comprising a therapeutically effective amount of a compound of the formula:

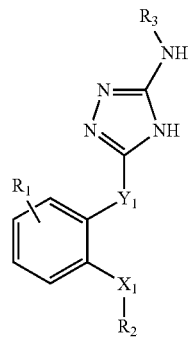

(I)

wherein: $R_1$ is hydrogen, halo, hydroxy, amino, nitro, cyano, alkyl$_{(C\leq12)}$, or substituted alkyl$_{(C\leq12)}$; $Y_1$ is alkanediyl$_{(C\leq12)}$, alkylaminodiyl$_{(C\leq12)}$, alkoxydiyl$_{(C\leq12)}$, or a substituted version of any of these groups; $X_1$ is —O—, —S—, or —NR$_3$—, wherein $R_3$ is hydrogen or alkyl$_{(C\leq6)}$; $R_2$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_3$ is hydrogen, hydroxy, alkyl$_{(C\leq12)}$, substituted alkyl$_{(C\leq12)}$, alkoxy$_{(C\leq12)}$, or substituted alkoxy$_{(C\leq12)}$; or

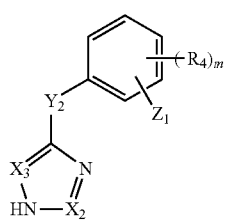

(III)

$R_4$ is each independently hydrogen, hydroxy, halo, nitro, or cyano, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, or a substituted version of any of these groups; m is 0, 1, 2, 3, or 4; $X_2$ and $X_3$ are each independently $CR_5$ or N; wherein: $R_5$ is hydrogen, amino, alkyl$_{(C\leq12)}$, substituted alkyl$_{(C\leq12)}$, alkylamino$_{(C\leq12)}$, substituted alkylamino$_{(C\leq12)}$, aryl$_{(C\leq12)}$, substituted aryl$_{(C\leq12)}$, aralkyl$_{(C\leq12)}$, substituted aralkyl$_{(C\leq12)}$, aralkylamino$_{(C\leq12)}$, substituted aralkylamino$_{(C\leq12)}$, alkoxy$_{(C\leq12)}$, or substituted alkoxy$_{(C\leq12)}$; $Y_2$ is alkanediyl$_{(C\leq12)}$, alkylaminodiyl$_{(C\leq12)}$, alkoxydiyl$_{(C\leq12)}$, or a substituted version of any of these groups; and $Z_1$ is halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or

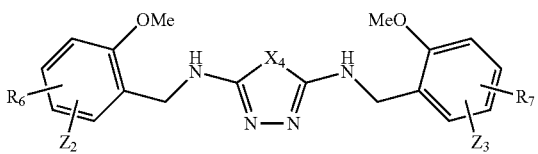

(IV)

$R_6$ and $R_7$ are each independently hydrogen, hydroxy, halo, nitro, cyano, or alkyl$_{(C\leq12)}$, alkenyl$_{(C\leq12)}$, alkynyl$_{(C\leq12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; $X_4$ is —$CR_8R_{8'}$—, —$NR_8$—, —O—, or S; wherein: $R_8$ and $R_{8'}$ are each independently hydrogen, alkyl$_{(C≤12)}$, or substituted alkyl$_{(C≤12)}$; and $Z_4$ and $Z_5$ are each independently hydrogen, halo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; or

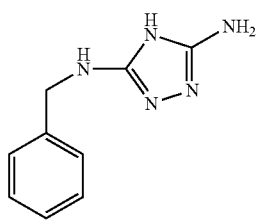 [SMILES: Nc1nnc(NCc2ccccc2)[nH]1]

or a pharmaceutically acceptable salt or tautomer, thereof. In some embodiments, the enzyme is LSD1. In some embodiments, the enzyme is SMOX. In some embodiments, the activity of the enzyme is inhibited by more than 50%. In some embodiments, the activity of the enzyme is inhibited by more than 70%. In some embodiments, the activity of the enzyme is inhibited by more than 90%. In some embodiments, the enzyme is inhibited in vitro. In some embodiments, the enzyme is inhibited in vivo. In some embodiments, the method of inhibiting the enzyme in vivo further comprises administering the compound to a patient in need thereof. In some embodiments, the patient is a mammal. In some embodiments, the patient is a human.

In another aspect, the present disclosure provides a method of reducing the size of a tumor comprising administering to a patient a therapeutically effective amount of a compound of the formula:

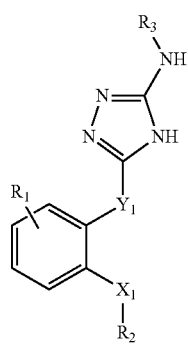

(I)

wherein: $R_1$ is hydrogen, halo, hydroxy, amino, nitro, cyano, alkyl$_{(C≤12)}$, or substituted alkyl$_{(C≤12)}$; $Y_1$ is alkanediyl$_{(C≤12)}$, alkylaminodiyl$_{(C≤12)}$, alkoxydiyl$_{(C≤12)}$, or a substituted version of any of these groups; $X_1$ is —O—, —S—, or —$NR_3$—, wherein $R_3$ is hydrogen or alkyl$_{(C≤6)}$; $R_2$ is alkyl$_{(C≤12)}$, aryl$_{(C≤12)}$, aralkyl$_{(C≤12)}$, heteroaryl$_{(C≤12)}$, heteroaralkyl$_{(C≤12)}$, or a substituted version of any of these groups; and $R_3$ is hydrogen, hydroxy, alkyl$_{(C≤12)}$, substituted alkyl$_{(C≤12)}$, alkoxy$_{(C≤12)}$, or substituted alkoxy$_{(C≤12)}$; or

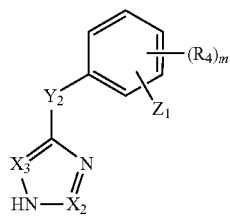

(III)

$R_4$ is each independently hydrogen, hydroxy, halo, nitro, or cyano, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, aryloxy$_{(C≤12)}$, aralkoxy$_{(C≤12)}$, or a substituted version of any of these groups; m is 0, 1, 2, 3, or 4; $X_2$ and $X_3$ are each independently $CR_5$ or N; wherein: $R_5$ is hydrogen, amino, alkyl$_{(C≤12)}$, substituted alkyl$_{(C≤12)}$, alkylamino$_{(C≤12)}$, substituted alkylamino$_{(C≤12)}$, aryl$_{(C≤12)}$, substituted aryl$_{(C≤12)}$, aralkyl$_{(C≤12)}$, substituted aralkyl$_{(C≤12)}$, aralkylamino$_{(C≤12)}$, substituted aralkylamino$_{(C≤12)}$, alkoxy$_{(C≤12)}$, or substituted alkoxy$_{(C≤12)}$; $Y_2$ is alkanediyl$_{(C≤12)}$, alkylaminodiyl$_{(C≤12)}$, alkoxydiyl$_{(C≤12)}$, or a substituted version of any of these groups; and $Z_1$ is halo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; or

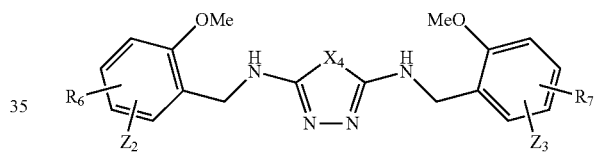

(IV)

$R_6$ and $R_7$ are each independently hydrogen, hydroxy, halo, nitro, cyano, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; $X_4$ is —$CR_8R_{8'}$—, —$NR_8$—, —O—, or S; wherein: $R_8$ and $R_{8'}$ are each independently hydrogen, alkyl$_{(C≤12)}$, or substituted alkyl$_{(C≤12)}$; and $Z_4$ and $Z_5$ are each independently hydrogen, halo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; or

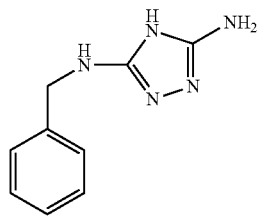

or a pharmaceutically acceptable salt or tautomer, thereof. In some embodiments, the patient is a mammal. In some embodiments, the patient is a human. In some embodiments, the compound is administered once. In some embodiments, the compound is administered two or more times.

In still another aspect, the present disclosure provides a method of preventing tissue damage related to ischemia or reperfusion injury comprising administering to a patient in need thereof a therapeutically effective amount of a compound of the formula:

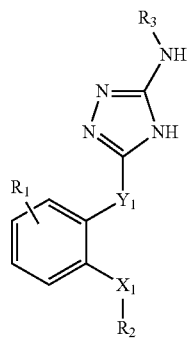

(I)

wherein: $R_1$ is hydrogen, halo, hydroxy, amino, nitro, cyano, alkyl$_{(C \leq 12)}$, or substituted alkyl$_{(C \leq 12)}$; $Y_1$ is alkanediyl$_{(C \leq 12)}$, alkylaminodiyl$_{(C \leq 12)}$, alkoxydiyl$_{(C \leq 12)}$, or a substituted version of any of these groups; $X_1$ is —O—, —S—, or —NR$_3$—, wherein $R_3$ is hydrogen or alkyl$_{(C \leq 6)}$; $R_2$ is alkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, or a substituted version of any of these groups; and $R_3$ is hydrogen, hydroxy, alkyl$_{(C \leq 12)}$, substituted alkyl$_{(C \leq 12)}$, alkoxy$_{(C \leq 12)}$, or substituted alkoxy$_{(C \leq 12)}$; or

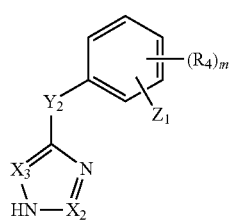

(III)

$R_4$ is each independently hydrogen, hydroxy, halo, nitro, or cyano, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, aryloxy$_{(C \leq 12)}$, aralkoxy$_{(C \leq 12)}$, or a substituted version of any of these groups; m is 0, 1, 2, 3, or 4; $X_2$ and $X_3$ are each independently $CR_5$ or N; wherein: $R_5$ is hydrogen, amino, alkyl$_{(C \leq 12)}$, substituted alkyl$_{(C \leq 12)}$, alkylamino$_{(C \leq 12)}$, substituted alkylamino$_{(C \leq 12)}$, aryl$_{(C \leq 12)}$, substituted aryl$_{(C \leq 12)}$, aralkyl$_{(C \leq 12)}$, substituted aralkyl$_{(C \leq 12)}$, aralkylamino$_{(C \leq 12)}$, substituted aralkylamino$_{(C \leq 12)}$, alkoxy$_{(C \leq 12)}$, or substituted alkoxy$_{(C \leq 12)}$; $Y_2$ is alkanediyl$_{(C \leq 12)}$, alkylaminodiyl$_{(C \leq 12)}$, alkoxydiyl$_{(C \leq 12)}$, or a substituted version of any of these groups; and $Z_1$ is halo, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, or a substituted version of any of these groups; or

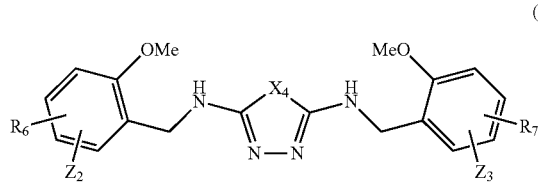

(IV)

$R_6$ and $R_7$ are each independently hydrogen, hydroxy, halo, nitro, cyano, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, or a substituted version of any of these groups; $X_4$ is —CR$_8$R$_{8'}$—, —NR$_8$—, —O—, or S; wherein: $R_8$ and $R_{8'}$ are each independently hydrogen, alkyl$_{(C \leq 12)}$, or substituted alkyl$_{(C \leq 12)}$; and $Z_4$ and $Z_5$ are each independently hydrogen, halo, or alkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, alkoxy$_{(C \leq 12)}$, or a substituted version of any of these groups; or

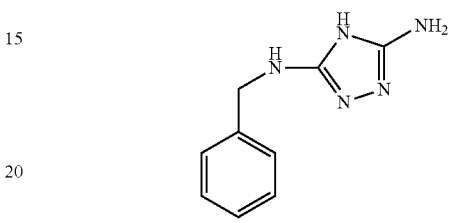

or a pharmaceutically acceptable salt or tautomer, thereof. In some embodiments, the tissue is cardiac tissue. In some embodiments, the ischemia comprised reduced blood flow to the heart. In some embodiments, the tissue damage results from the reperfusion of blood into the tissue after the blood flow has been reduced or stopped to the issue. In some embodiments, the patient is a mammal. In some embodiments, the patient is a human. In some embodiments, the compound is administered once. In some embodiments, the compound is administered two or more times.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3a-b—IC$_{50}$ determination for C1 (A) and C15 (B) against purified recombinant LSD1. Each data point is the average of 3 determinations ±standard error of the mean.

DESCRIPTION OF ILLUSTRATIVE EMBODIMENTS

Figure 1:
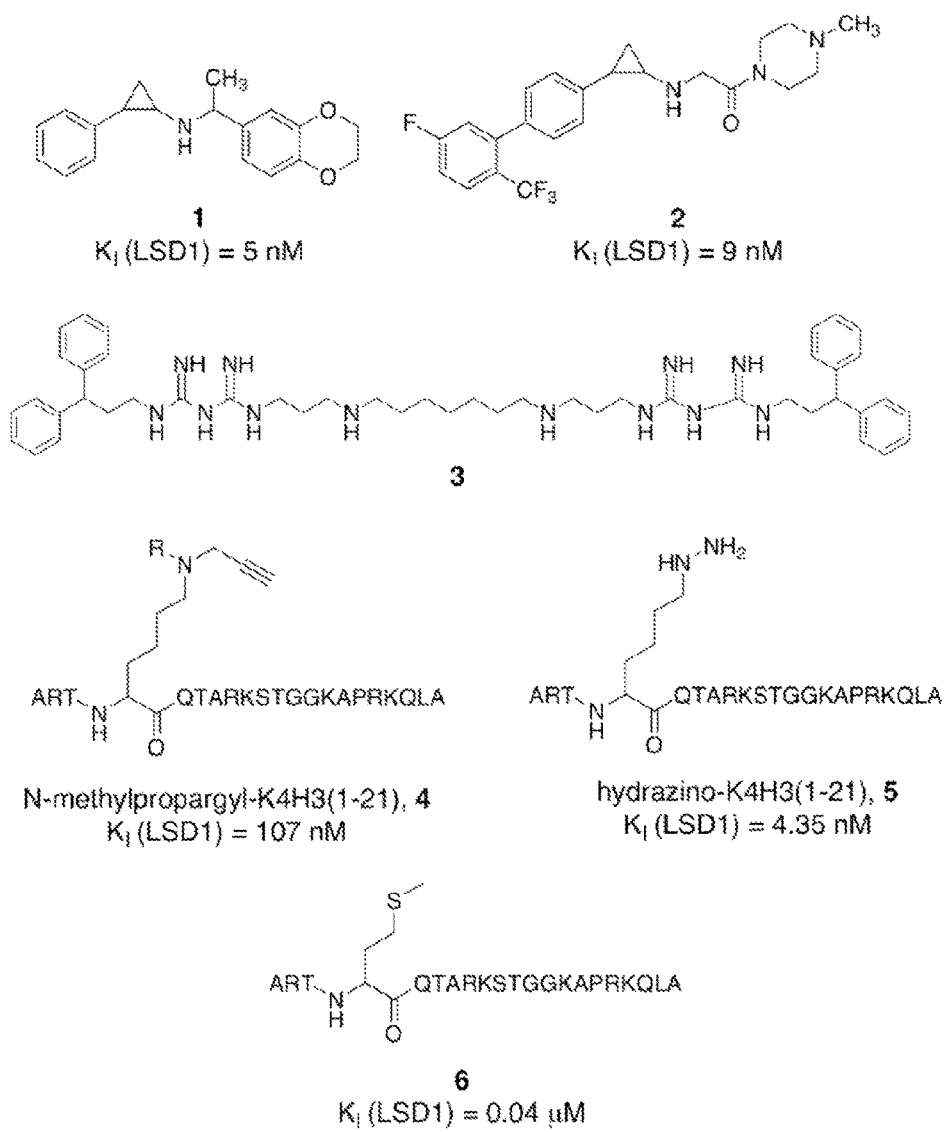
FIG. 1—Structures of the LSD1 inhibitors 1 and 2 (tranylcypromine-based), verlindamycin 3 (oligoamine-based) and 4-6 (peptide based).

Disclosed herein are new compounds and compositions based upon aminotriazole or aminotetrazole which act as inhibitors of LSD1 (KDM1A). In some embodiments, these compounds can be used in compositions or methods of treating disorders and diseases such as cancer or cardiovascular disease.

I. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanate" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "⸺" represents a single bond or a double bond. Thus, for example, the formula

includes

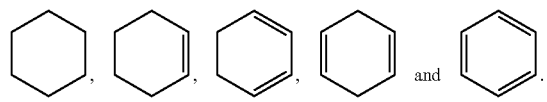

And it is understood that no one such ring atom forms part of more than one double bond. Furthermore, it is noted that the covalent bond symbol "—", when connecting one or two stereogenic atoms, does not indicate any preferred stereochemistry. Instead, it cover all stereoisomers as well as mixtures thereof. The symbol "⩘", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◀" means a single bond where the group attached to the thick end of the wedge is "out of the page." The symbol "⫽" means a single bond where the group attached to the thick end of the wedge is "into the page". The symbol "⩘" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom.

When a group "R" is depicted as a "floating group" on a ring system, for example, in the formula:

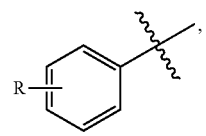

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

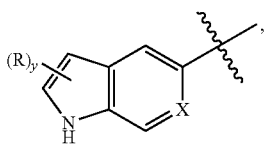

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤8)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl, with the carbon atom that forms the point of attachment also being a member of one or more non-aromatic ring structures wherein the cycloalkyl group consists of no atoms other than carbon and hydrogen. As used herein, the term does not preclude the presence of one or more alkyl groups (carbon number limitation permitting) attached to the ring or ring system. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —CH$_2$— (methylene), —CH$_2$CH$_2$—, —CH$_2$C(CH$_3$)$_2$CH$_2$—, —CH$_2$CH$_2$CH$_2$—, and are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halo are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH$_3$)CH$_2$—, —CH=CHCH$_2$—, and

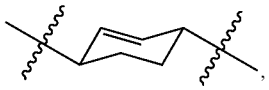 [SMILES: *C1C=CC(*)CC1]

are non-limiting examples of alkenediyl groups. It is noted that while the alkenediyl group is aliphatic, once connected at both ends, this group is not precluded from forming part of an aromatic structure. The terms "alkene" or "olefin" are synonymous and refer to a compound having the formula H—R, wherein R is alkenyl as this term is defined above. A "terminal alkene" refers to an alkene having just one carbon-carbon double bond, wherein that bond forms a vinyl group at one end of the molecule. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —CH=CHF, —CH=CHCl and —CH=CHBr, are non-limiting examples of substituted alkenyl groups.

The term "alkynyl" when used without the "substituted" modifier refers to an monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH$_3$, and —CH$_2$C≡CCH$_3$, are non-limiting examples of alkynyl groups. An "alkyne" refers to the compound H—R, wherein R is alkynyl. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

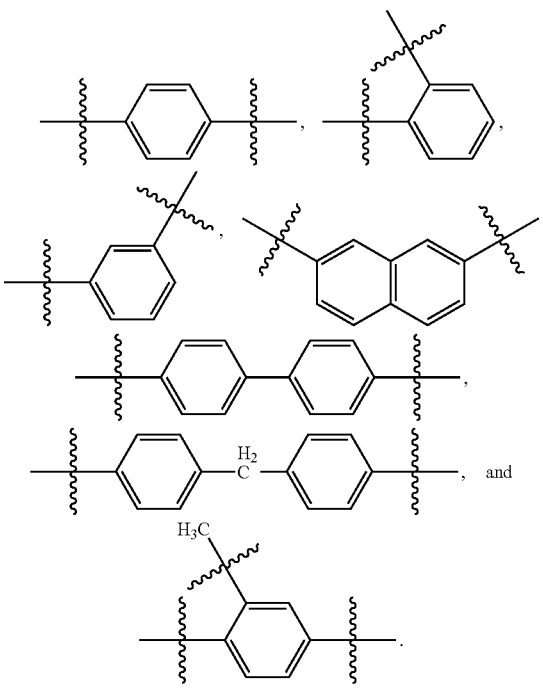

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Furthermore, the substituted modifier includes two adjacent hydrogen atoms having been replaced by —OCH$_2$O— or —OCH$_2$CH$_2$O—, such that a five and six membered ring is formed, respectively.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term aralkyl is used with the "substituted" modifier one or more hydrogen atom from the alkanediyl and/or the aryl group has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Furthermore, the substituted modifier includes two adjacent hydrogen atoms having been replaced by —OCH$_2$O— or —OCH$_2$CH$_2$O—, such that a five and six membered ring is formed, respectively. Non-limiting examples of substituted aralkyls are: (3-chlorophenyl)-methyl, and 2-chloro-2-phenyl-eth-1-yl.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

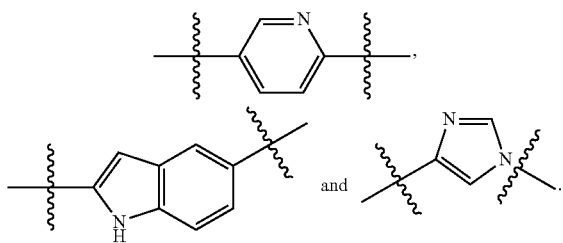

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. Furthermore, the substituted modifier includes two adjacent hydrogen atoms having been replaced by —OCH$_2$O— or —OCH$_2$CH$_2$O—, such that a five and six membered ring is formed, respectively.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH (CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), —O(CH$_3$)$_3$ (tert-butoxy), —OCH(CH$_2$)$_2$, —O-cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O-alkanediyl-O—, or -alkanediyl-O-alkanediyl-. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —OC$_6$H$_5$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", and "heteroarylamino" when used without the "substituted" modifier, refers to groups, defined as —NHR, in which R is alkoxy, alkenyl, alkynyl, aryl, aralkyl, and heteroaryl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$OC_6H_5$, —$C(O)CH_3$, —$NHCH_3$, —$NHCH_2CH_3$, —$N(CH_3)_2$, —$C(O)NH_2$, —$OC(O)CH_3$, or —$S(O)_2NH_2$. The groups —$NHC(O)OCH_3$ and —$NHC(O)NHCH_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "$IC_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, horse, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

Other abbreviations used herein are as follows: $^1$H NMR, proton nuclear magnetic resonance spectroscopy; DMSO, dimethyl sulfoxide; h or hr, hour(s); LSD1, lysine-specific demethylase 1, also known as BHC110 and KDM1A; SMOX, spermine oxidase; HDAC, histone deacetylase; HDAC1, histone deacetylase 1; and REST, RE1 silencing transcription factor.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

II. Compounds and Synthetic Methods

The compounds provided by the present disclosure are shown here and above in the summary of the invention section and in the claims below. For example, the compounds could be of the formula:

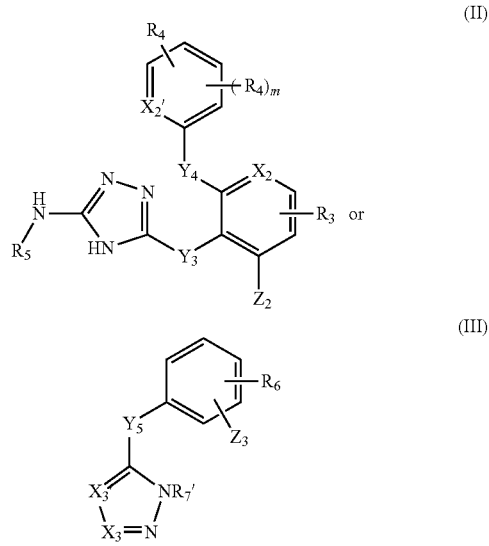

wherein: $R_3$, $R_4$, and $R_{4'}$ are each independently hydrogen, hydroxy, halo, mercapto, nitro, cyano, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, aryloxy$_{(C≤12)}$, aralkoxy$_{(C≤12)}$, alkylthio$_{(C≤12)}$, or a substituted version of any of these groups; or $R_4$ and $R_{4'}$ are taken together to form

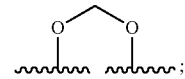 [SMILES: *OCO*]

$R_5$ is hydrogen, alkyl$_{(C≤12)}$, substituted alkyl$_{(C≤12)}$, alkoxy$_{(C≤12)}$, or substituted alkoxy$_{(C≤12)}$; $R_6$ is each independently hydrogen, hydroxy, halo, nitro, or cyano, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, aryloxy$_{(C≤12)}$, aralkoxy$_{(C≤12)}$, or a substituted version of any of these groups; m is 1, 2, 3, or 4; $X_2$ and $X_{2'}$ are each independently $CR_7$, N, S, or O; $X_3$ and $X_{3'}$ are each independently $CR_7$ or N; wherein: $R_7$ and $R_{7'}$ are each independently hydrogen, alkyl$_{(C≤12)}$, substituted alkyl$_{(C≤12)}$, aryl$_{(C≤12)}$, substituted aryl$_{(C≤12)}$, aralkyl$_{(C≤12)}$, substituted aralkyl$_{(C≤12)}$, aralkylamino$_{(C≤12)}$, substituted aralkylamino$_{(C≤12)}$, alkoxy$_{(C≤12)}$, or substituted alkoxy$_{(C≤12)}$; $Y_3$, $Y_4$, and $Y_5$ are each independently —O—, —S—, —NH—, alkanediyl$_{(C≤12)}$, alkoxydiyl$_{(C≤12)}$, alkylaminodiyl$_{(C≤12)}$, substituted alkanediyl$_{(C≤12)}$, substituted alkoxydiyl$_{(C≤12)}$, or substituted alkylaminodiyl$_{(C≤12)}$; $Z_2$ is halo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; or $Z_3$ is hydrogen, halo, or alkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, alkoxy$_{(C≤12)}$, or a substituted version of any of these groups; or

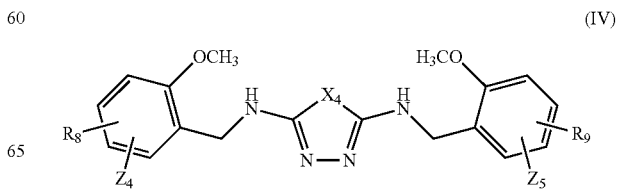

wherein: $R_8$ and $R_9$ are each independently hydrogen, hydroxy, halo, nitro, cyano, or; alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; $X_4$ is —$CR_{10}R_{10'}$, —$NR_{10}$—, —O—, or S; wherein: $R_{10}$ and $R_{10'}$ are each independently hydrogen, alkyl$_{(C\leq12)}$, or substituted alkyl$_{(C\leq12)}$; $Z_4$ and $Z_5$ are each independently hydrogen, halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or a pharmaceutically acceptable salt or tautomer, thereof.

In another embodiment, the compounds have the formula:

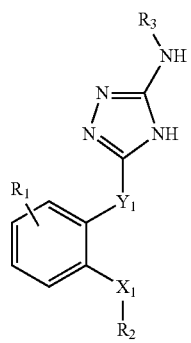

(I)

wherein: $R_1$ is hydrogen, halo, hydroxy, amino, nitro, cyano, alkyl$_{(C\leq12)}$, or substituted alkyl$_{(C\leq12)}$; $Y_1$ is alkanediyl$_{(C\leq12)}$, alkylaminodiyl$_{(C\leq12)}$, alkoxydiyl$_{(C\leq12)}$, or a substituted version of any of these groups; $X_1$ is —O—, —S—, or —$NR_3$—, wherein $R_3$ is hydrogen or alkyl$_{(C\leq6)}$; and $R_2$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; provided that $R_2$ is not phenyl when $X_1$ is —O—; or a pharmaceutically acceptable salt or tautomer thereof.

TABLE 1

Compounds of the Present Disclosure

| Compound ID | Structure |
|---|---|
| C1 | |
| C2 | 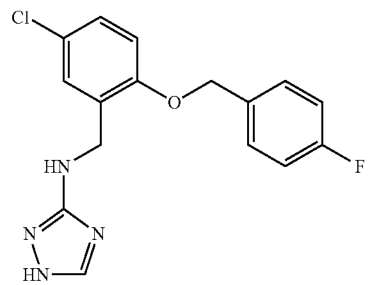 [SMILES: Fc1ccc(COc2ccc(Cl)cc2CNc2nc[nH]n2)cc1] |
| C3 | 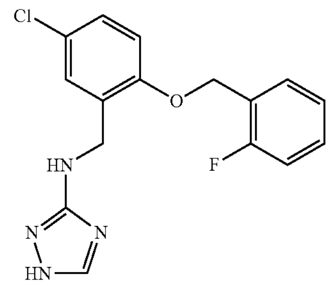 [SMILES: Fc1ccccc1COc1ccc(Cl)cc1CNc1nc[nH]n1] |
| C4 | 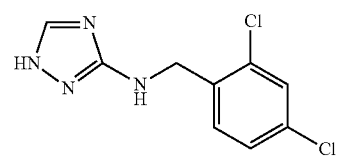 [SMILES: Clc1ccc(CNc2nc[nH]n2)c(Cl)c1] |
| C5 | 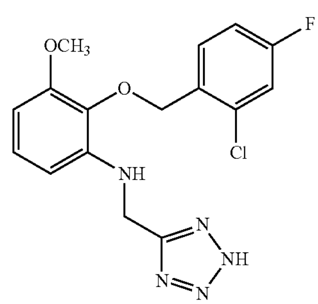 [SMILES: COc1cccc(NCc2nn[nH]n2)c1OCc1ccc(F)cc1Cl] |
| C6 | 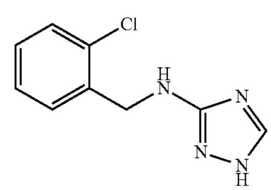 [SMILES: Clc1ccccc1CNc1nc[nH]n1] |
| C7 | 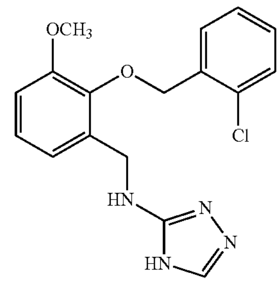 [SMILES: COc1cccc(CNc2nnc[nH]2)c1OCc1ccccc1Cl] |

TABLE 1-continued

Compounds of the Present Disclosure

| Compound ID | Structure |
|---|---|
| C8 | (structure) |
| C9 | (structure) |
| C10 | (structure) |
| C11 | (structure) |
| C12 | (structure) |
| C13 | (structure) |
| C14 | (structure) |
| C15 | (structure) |
| 5a | (structure) |
| 5b | (structure) |
| 5c | (structure) |

TABLE 1-continued

Compounds of the Present Disclosure

| Compound ID | Structure |
|---|---|
| 5d | 3-methoxyphenoxy-chlorobenzyl linked to 3-amino-1,2,4-triazole via NH |
| 5e | benzyl linked to 3-amino-1,2,4-triazole via NH |
| 5f | 4-tert-butylphenoxy-chlorobenzyl linked to 3-amino-1,2,4-triazole via NH |
| 5g | 3,5-dimethylphenoxy-chlorobenzyl linked to 3-amino-1,2,4-triazole via NH |
| 5h | 3,5-bis(trifluoromethyl)phenoxy-chlorobenzyl linked to 3-amino-1,2,4-triazole via NH |
| 5i | 4-(trifluoromethylthio)phenoxy-chlorobenzyl linked to 3-amino-1,2,4-triazole via NH |
| 5j | 2,4-dibromophenoxy-chlorobenzyl linked to 3-amino-1,2,4-triazole via NH |
| 5k | 4-bromo-2-(trifluoromethyl)phenoxy-chlorobenzyl linked to 3-amino-1,2,4-triazole via NH |
| 5l | 4-(methylthio)phenoxy-chlorobenzyl linked to 3-amino-1,2,4-triazole via NH |
| 5m | 2-methoxy-4-methylphenoxy-chlorobenzyl linked to 3-amino-1,2,4-triazole via NH |
| 5n | 3,5-dimethoxyphenoxy-chlorobenzyl linked to 3-amino-1,2,4-triazole via NH |

TABLE 1-continued
Compounds of the Present Disclosure
| Compound ID | Structure |
|---|---|
| 5p | 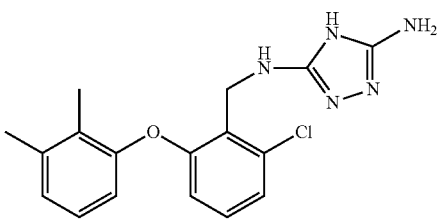 [SMILES: Cc1cccc(Oc2cccc(Cl)c2CNc2nnc(N)[nH]2)c1C] |
| 5q | 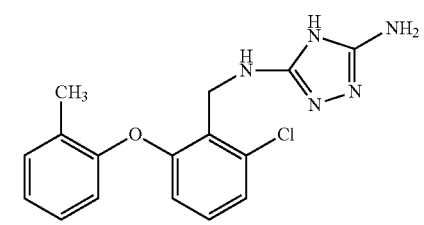 |
| 5r | 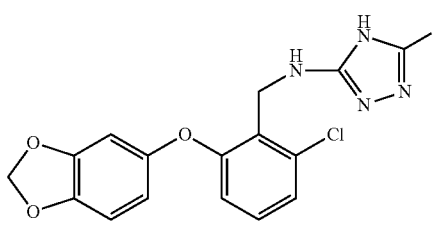 |
| 5s | 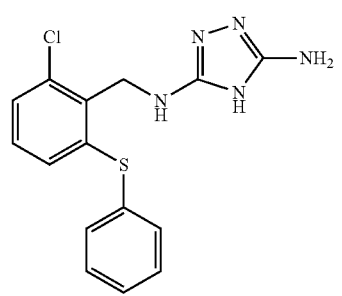 [SMILES: Nc1nnc(NCc2c(Cl)cccc2Sc2ccccc2)[nH]1] |
| 5t | 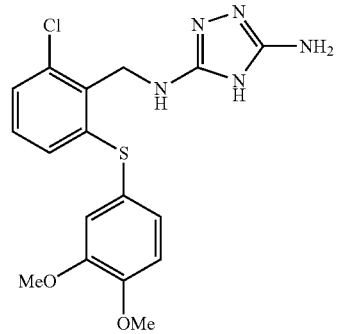 [SMILES: COc1ccc(Sc2cccc(Cl)c2CNc2nnc(N)[nH]2)cc1OC] |
| M1 | 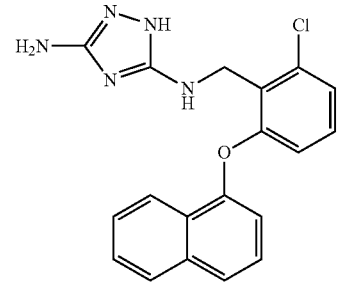 [SMILES: Nc1n[nH]c(NCc2c(Cl)cccc2Oc2cccc3ccccc23)n1] |
| M2 | 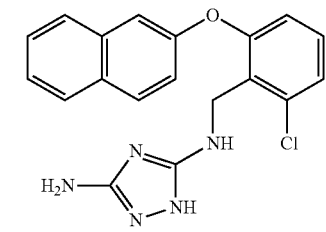 [SMILES: Nc1n[nH]c(NCc2c(Cl)cccc2Oc2ccc3ccccc3c2)n1] |
| M3 | 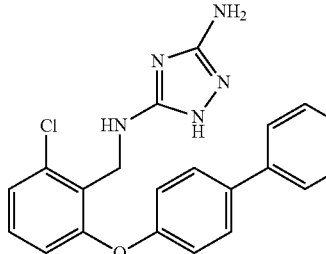 |
| M4 | 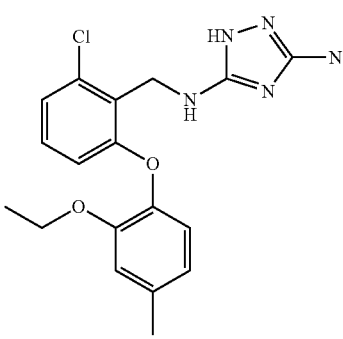 |
| M5 | 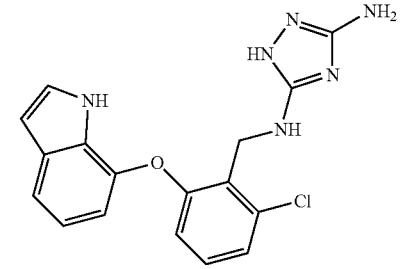 [SMILES: Nc1n[nH]c(NCc2c(Cl)cccc2Oc2cccc3cc[nH]c23)n1] |

TABLE 1-continued

Compounds of the Present Disclosure

| Compound ID | Structure |
|---|---|
| M6 | 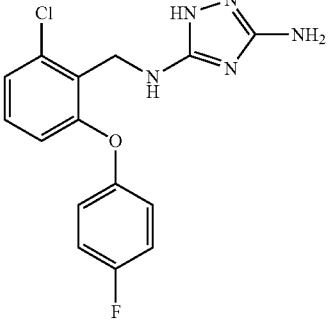 |
| M7 | 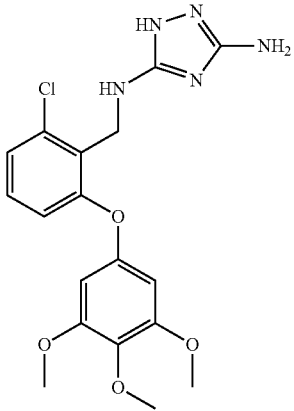 [SMILES: COc1cc(Oc2cccc(Cl)c2CNc2nc(N)n[nH]2)cc(OC)c1OC] |
| M8 | 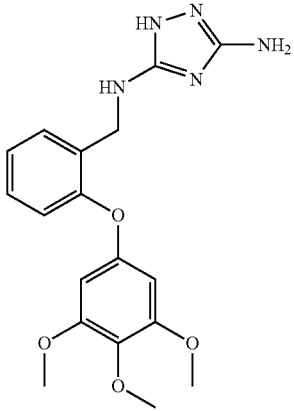 [SMILES: COc1cc(Oc2ccccc2CNc2nc(N)n[nH]2)cc(OC)c1OC] |
| M9 | 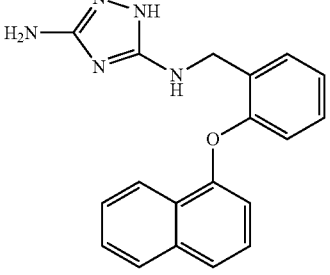 |
| M10 | 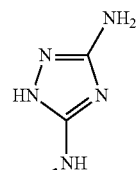 |
| H1 | 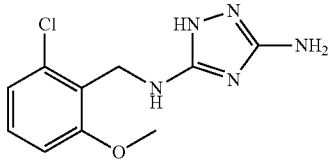 [SMILES: COc1cccc(Cl)c1CNc1nc(N)n[nH]1] |

The compounds may be made using the methods outlined in the Examples section. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

The heterocyclic compounds of the invention may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration.

Chemical formulas used to represent compounds of the invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Atoms making up the compounds of the present invention are intended to include all isotopic forms of such atoms. Compounds of the present invention include those with one or more atoms that have been isotopically modified or enriched, in particular those with pharmaceutically acceptable isotopes or those useful for pharmaceutically research. Isotopes, as used herein, include those atoms having the same atomic number but different mass numbers. By way of general example and without limitation, isotopes of hydrogen include deuterium and tritium, and isotopes of carbon include $^{13}$C and $^{14}$C. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

Compounds of the present invention may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It should be further recognized that the compounds of the present invention include those that have been further modified to comprise substituents that are convertible to hydrogen in vivo. This includes those groups that may be convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydropyranyl, diphenylphosphinyl, and the like. Examples of acyl groups include formyl, acetyl, trifluoroacetyl, and the like. Examples of groups having an oxycarbonyl group include ethoxycarbonyl, tert-butoxycarbonyl (—C(O)OC(CH$_3$)$_3$, Boc), benzyloxycarbonyl, p-methoxybenzyloxycarbonyl, vinyloxycarbonyl, β-(p-toluenesulfonyl)ethoxycarbonyl, and the like. Suitable amino acid residues include, but are not limited to, residues of Gly (glycine), Ala (alanine), Arg (arginine), Asn (asparagine), Asp (aspartic acid), Cys (cysteine), Glu (glutamic acid), His (histidine), Ile (isoleucine), Leu (leucine), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable amino acid residues also include amino acid residues that are protected with a protecting group. Examples of suitable protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$, Boc), and the like. Suitable peptide residues include peptide residues comprising two to five amino acid residues. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethoxycarbonyl groups (such as benzyloxycarbonyl and p-nitrobenzyloxycarbonyl), tert-butoxycarbonyl groups (—C(O)OC(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and haloethoxycarbonyl groups (such as β,β,β-trichloroethoxycarbonyl and β-iodoethoxycarbonyl).

Compounds of the invention may also have the advantage that they may be more efficacious than, be less toxic than, be longer acting than, be more potent than, produce fewer side effects than, be more easily absorbed than, have a better pharmacokinetic profile (e.g., higher oral bioavailability and/or lower clearance) and/or be easier to produce on industrial useful scales than, and/or have other useful pharmacological, physical, or chemical properties over, compounds known in the prior art, whether for use in the indications stated herein or otherwise.

III. Biological Activity of LSD1

Histone proteins occur as octamers that consist of one H3-H4 tetramer and two H2A-H2B dimers (Strahl and Allis, 2000). These proteins interact with double stranded DNA in such a way that approximately 146 base pairs of DNA are wrapped around the histone octamer to form nucleosomes. The lysine-containing tails of histones, consisting of up to 40 amino acid residues, protrude through the DNA strand, and act as a site for post-translational modification of chromatin (acetylation, methylation, phosphorylation, ubiquitylation, sumoylation, ADP ribosylation, deamination and proline isomerization), allowing alteration of higher order nucleosome structure (Jenuwein and Allis, 2001; Latham and Dent, 2007). There are numerous lysine methylation sites on histone tails, and specific lysine marks can promote transcriptional activation or silencing. Histone 3 lysine 4 (H3K4) is a transcription-activating chromatin mark at gene promoters, and demethylation of this mark by LSD1 may prevent expression of tumor suppressor genes important in human cancer (Huang, et al., 2007). By contrast, H3K9 methylation results transcription repression (Forneris, et al., 2005). The flavin-dependent demethylase LSD1, also known as BHC110 and KDM1A, (Shi, et al., 2007; Shi, et al., 2004) catalyzes the oxidative demethylation of histone 3 methyllysine 4 (H3K4me1) and histone 3 dimethyllysine 4 (H3K4me2). In some embodiments, because LSD1 is overexpressed in a number of human cancers (for example, neuroblastoma, retinoblastoma, prostate cancer, breast cancer, lung cancer and bladder cancer) (Hayami, et al., 2011; Lim, et al., 2010; Schulte, et al., 2009; Rotili and Mai, 2011), potential inhibitors of the protein are an effective target for the treatment of cancer (Stavropoulos and Hoelz, 2007).

IV. Cardiovascular Disease

In some aspects, the present disclosure provides a method of preventing or treating a cardiovascular disease. In some embodiments, the cardiovascular disease is a result of an ischemic event. Some non-limiting examples of cardiovascular diseases include reperfusion injury or heart failure. Histone deacetylase enzymes have been shown to be effective targets for cardiovascular diseases (Chandrasekaran, et al). Inhibition of histone demethylases such as LSD1 can provide an alternative way to modulate the activity of histone deacetylase enzymes.

V. Pharmaceutical Formulations and Routes of Administration

In some aspects, the pharmaceutical compositions, methods, or uses described herein comprise a compound of the formula:

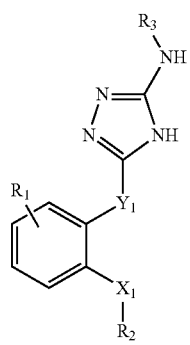
(I)

wherein: $R_1$ is hydrogen, halo, hydroxy, amino, nitro, cyano, alkyl$_{(C\leq12)}$, or substituted alkyl$_{(C\leq12)}$; $Y_1$ is alkanediyl$_{(C\leq12)}$, alkylaminodiyl$_{(C\leq12)}$, alkoxydiyl$_{(C\leq12)}$, or a substituted version of any of these groups; $X_1$ is —O—, —S—, or —NR$_3$—, wherein $R_3$ is hydrogen or alkyl$_{(C\leq6)}$; $R_2$ is alkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, or a substituted version of any of these groups; and $R_3$ is hydrogen, hydroxy, alkyl$_{(C\leq12)}$, substituted alkyl$_{(C\leq12)}$, alkoxy$_{(C\leq12)}$, or substituted alkoxy$_{(C\leq12)}$; or

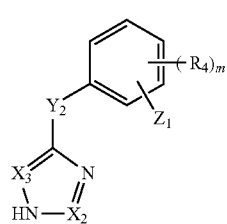
(III)

$R_4$ is each independently hydrogen, hydroxy, halo, nitro, or cyano, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, aryloxy$_{(C\leq12)}$, aralkoxy$_{(C\leq12)}$, or a substituted version of any of these groups; m is 0, 1, 2, 3, or 4; $X_2$ and $X_3$ are each independently CR$_5$ or N; wherein: $R_5$ is hydrogen, amino, alkyl$_{(C\leq12)}$, substituted alkyl$_{(C\leq12)}$, alkylamino$_{(C\leq12)}$, substituted alkylamino$_{(C\leq12)}$, aryl$_{(C\leq12)}$, substituted aryl$_{(C\leq12)}$, aralkyl$_{(C\leq12)}$, substituted aralkyl$_{(C\leq12)}$, aralkylamino$_{(C\leq12)}$, substituted aralkylamino$_{(C\leq12)}$, alkoxy$_{(C\leq12)}$, or substituted alkoxy$_{(C\leq12)}$; $Y_2$ is alkanediyl$_{(C\leq12)}$, alkylaminodiyl$_{(C\leq12)}$, alkoxydiyl$_{(C\leq12)}$, or a substituted version of any of these groups; and $Z_1$ is halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or

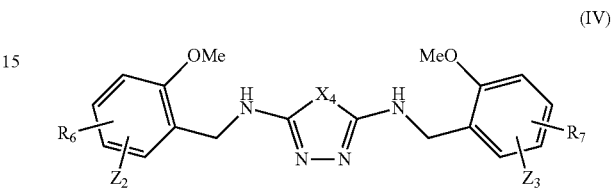
(IV)

$R_6$ and $R_7$ are each independently hydrogen, hydroxy, halo, nitro, cyano, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; $X_4$ is —CR$_8$R$_{8'}$—, —NR$_8$—, —O—, or S; wherein: $R_8$ and $R_{8'}$ are each independently hydrogen, alkyl$_{(C\leq12)}$, or substituted alkyl$_{(C\leq12)}$; and $Z_4$ and $Z_5$ are each independently hydrogen, halo, or alkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, alkoxy$_{(C\leq12)}$, or a substituted version of any of these groups; or

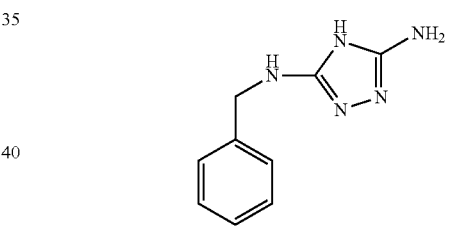

or a pharmaceutically acceptable salt or tautomer, thereof. The compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include: sterile aqueous solutions (where water soluble), dispersions, and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the subject has eaten or will eat.

VI. Combination Therapy

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another chemotherapeutic agent, surgery radiation therapy, an immunotherapy, or an anti-infective agent. Compounds of the invention may be combined with agents designed to improve a patient's immune response to cancer, including (but not limited to) cancer vaccines.

VII. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: LSD1 Inhibition

Figure 2:
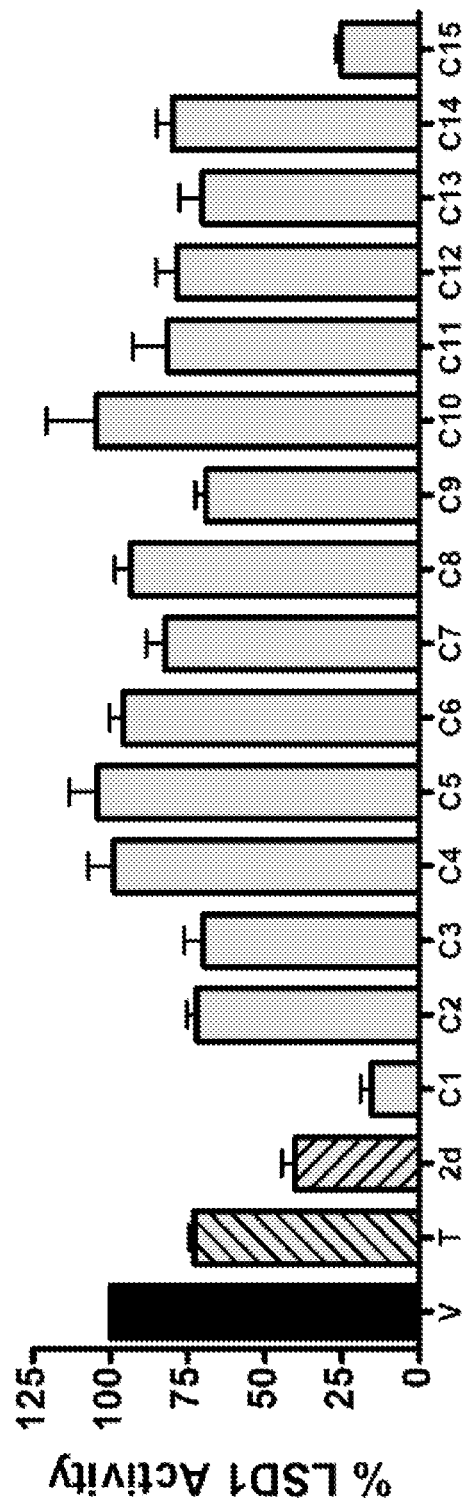
FIG. 2—Graphical representation of the inhibition of LSD1 by compounds C1-C15 in vitro. Tranylcypromine (T) and verlindamycin (aka 2d) were used as positive controls, while plain vehicle was used as a blank. Each bar represents the average of 3 determinations ±standard error of the mean.

Exploring potential inhibitors, compound C1 ($N^3$-(2-chloro-6-phenoxybenzyl)-4H-1,2,4-triazole-3,5-diamine) and 14 related analogues were purchased. These compounds were tested as inhibitors of LSD1. Two of these analogues, C1 and C15, proved to be potent inhibitors of LSD1 in an in vitro screen. The results of these screens can be seen in Table 1 and are represented graphically in FIG. 2.

TABLE 1

Analogues from the Chembridge Collection Evaluated as Inhibitors of LSD1 in vitro.

| Compound | Structure | Name | MW | % inhibition of recombinant LSD1 at 10 μM |
|---|---|---|---|---|
| Control | N/A | N/A | N/A | |
| TCP | [structure] | tranylcypromine | 133.19 | 27.4 |
| 2d | Verlindamycin tetrahydrochloride | N/A | 946.97 | 62.6 |
| C1 | [structure] | $N^3$-(2-chloro-6-phenoxybenzyl)-4H-1,2,4-triazole-3,5-diamine | 315.76 | 84.3 ± 4.5 |

TABLE 1-continued

Analogues from the Chembridge Collection Evaluated as Inhibitors of LSD1 in vitro.

| Compound | Structure | Name | MW | % inhibition of recombinant LSD1 at 10 μM |
|---|---|---|---|---|
| C2 | 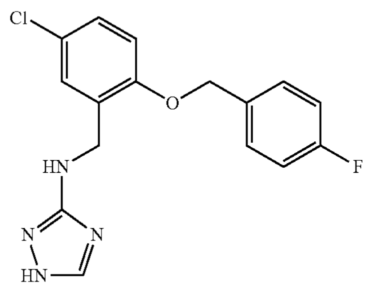 [SMILES: Fc1ccc(COc2ccc(Cl)cc2CNc2nc[nH]n2)cc1] | N-(5-chloro-2-((4-fluorobenzyl)oxy)benzyl)-1H-1,2,4-triazol-3-amine | 332.76 | 27.7 ± 9.0 |
| C3 | 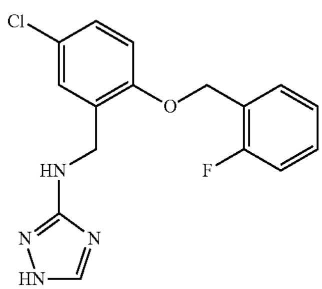 [SMILES: Fc1ccccc1COc1ccc(Cl)cc1CNc1nc[nH]n1] | N-(5-chloro-2-((2-fluorobenzyl)oxy)benzyl)-1H-1,2,4-triazol-3-amine | 332.76 | 30.6 ± 6.4 |
| C4 | 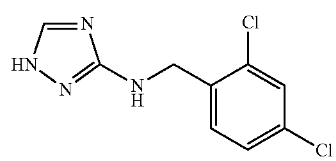 [SMILES: Clc1ccc(CNc2nc[nH]n2)c(Cl)c1] | N-(2,4-dichlorobenzyl)-1H-1,2,4-triazol-3-amine | 243.09 | 2.2 ± 6.9 |
| C5 | 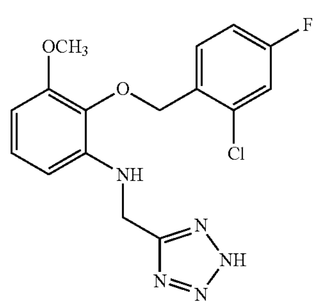 [SMILES: COc1cccc(NCc2nn[nH]n2)c1OCc1ccc(F)cc1Cl] | N-((2H-tetrazol-5-yl)methyl)-2-((2-chloro-4-fluorobenzyl)oxy)-3-methoxyaniline | 363.77 | −3.1 ± 7.8 |
| C6 | 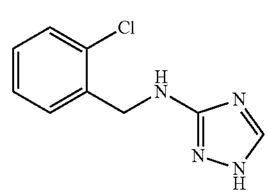 [SMILES: Clc1ccccc1CNc1nc[nH]n1] | N-(2-chlorobenzyl)-1H-1,2,4-triazol-3-amine | 208.65 | 4.6 ± 6.9 |
| C7 | 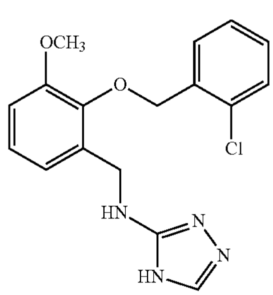 [SMILES: COc1cccc(CNc2nnc[nH]2)c1OCc1ccccc1Cl] | N-(2((2-chlorobenzyl)oxy)-3-methoxybenzyl)-4H-1,2,4-triazol-3-amine | 344.80 | 18.1 ± 8.2 |

TABLE 1-continued

Analogues from the Chembridge Collection Evaluated as Inhibitors of LSD1 in vitro.

| Compound | Structure | Name | MW | % inhibition of recombinant LSD1 at 10 μM |
|---|---|---|---|---|
| C8 | 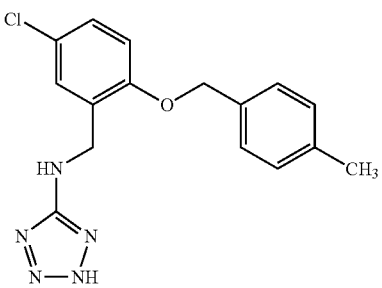 [SMILES: Cc1ccc(COc2ccc(Cl)cc2CNc2nn[nH]n2)cc1] | N-(5-chloro-2-((4-methylbenzyl)oxy)benzyl)-2H-tetrazol-5-amine | 329.78 | 6.9 ± 7.5 |
| C9 | 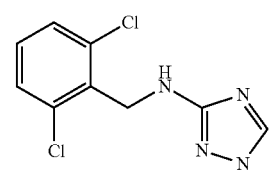 | N-(2,6-dichlorobenzyl)-1H-1,2,4-triazol-3-amine | 243.09 | 30.9 ± 7.7 |
| C10 | 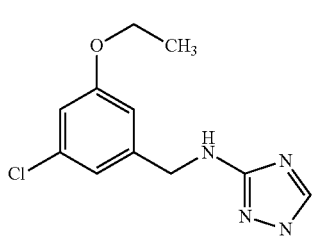 | N-(3-chloro-5-ethoxybenzyl)-1H-1,2,4-triazol-3-amine | 252.70 | −3.0 ± 12.7 |
| C11 | 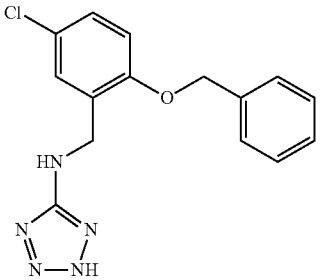 [SMILES: Clc1ccc(OCc2ccccc2)c(CNc2nn[nH]n2)c1] | N-(2-(benzyloxy)-5-chlorobenzyl)-2H-tetrazol-5-amine | 315.76 | 19.9 ± 8.4 |
| C12 | 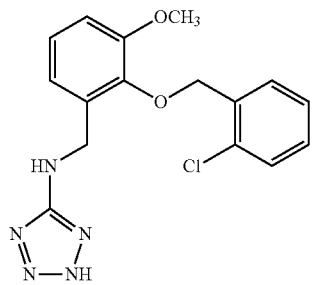 [SMILES: COc1cccc(CNc2nn[nH]n2)c1OCc1ccccc1Cl] | N-(2-((2-chlorobenzyl)oxy)-3-methoxybenzyl)-2H-tetrazol-5-amine | 345.78 | 22.1 ± 7.3 |

TABLE 1-continued

Analogues from the Chembridge Collection Evaluated as Inhibitors of LSD1 in vitro.

| Compound | Structure | Name | MW | % inhibition of recombinant LSD1 at 10 μM |
|---|---|---|---|---|
| C13 | 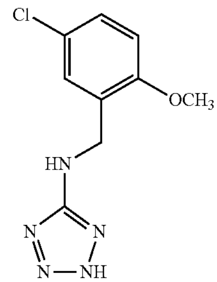 [SMILES: COc1ccc(Cl)cc1CNc1nn[nH]n1] | N-(5-chloro-2-methoxybenzyl)-2H-tetrazol-5-amine | 239.06 | 30.8 ± 5.7 |
| C14 | 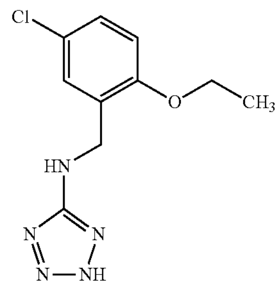 [SMILES: CCOc1ccc(Cl)cc1CNc1nn[nH]n1] | N-(5-chloro-2-ethoxybenzyl)-2H-tetrazol-5-amine | 253.69 | 20.8 ± 5.0 |
| C15 | 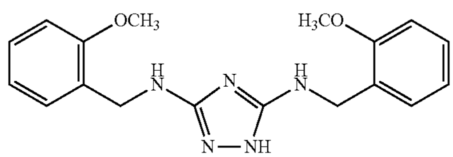 [SMILES: COc1ccccc1CNc1n[nH]c(NCc2ccccc2OC)n1] | $N^3,N^5$-bis(2-methoxybenzyl)-1H-1,2,4-triazole-3,5-diamine | 339.39 | 74.9 ± 1.9 |

Using a dose-response curve, the $IC_{50}$ of C1 and C15 were calculated. Compound C1 exhibited an $IC_{50}$ value of 1.1 μM (FIG. 3A), while C15 exhibited an $IC_{50}$ value of 2.2 μM (FIG. 3B) against recombinant human LSD1/CoREST.

Figure 4:
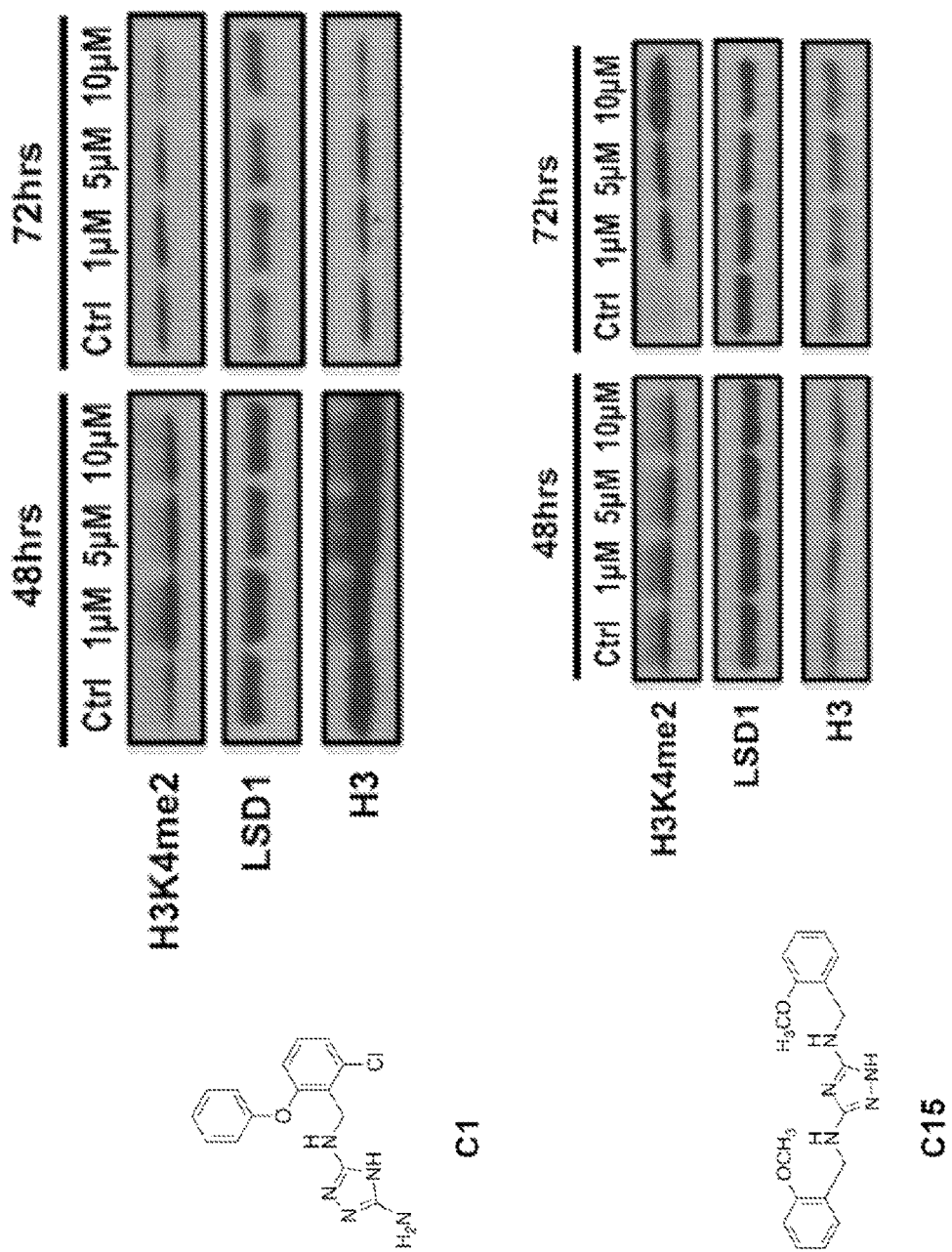
FIG. 4—Effect of LSD1 inhibitors C1 and C15 on H3K4me2 levels in the Calu 6 human anaplastic lung tumor cell line. Cells were treated for 48 or 72 hours with the indicated concentration of C1 or C15.
Figure 5:
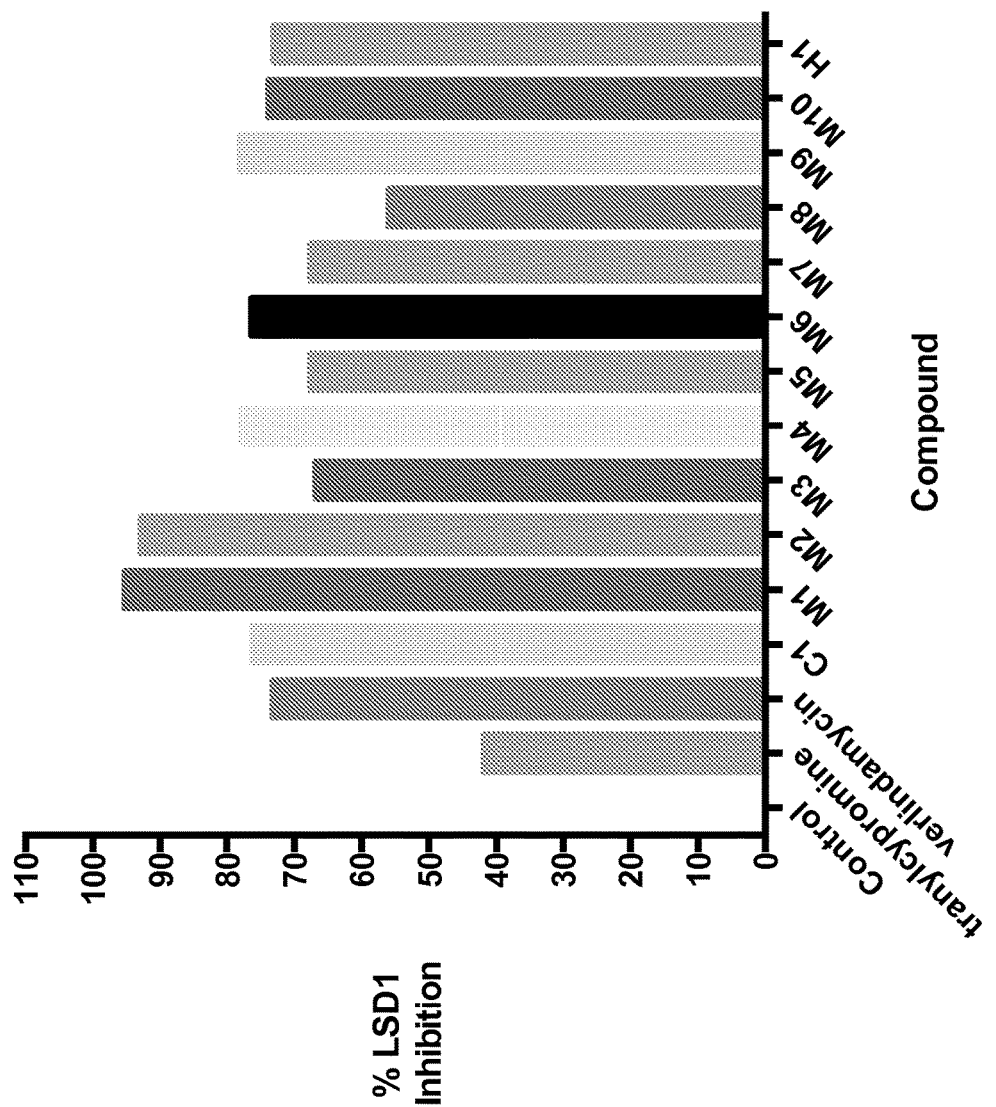
FIG. 5—Percent inhibition of LSD1 for control (no inhibitor), tranylcypromine, verlindamycin, compound C1, compounds M1-M10, and compound H1 at a concentration of 10 μM.

To verify that C1 and C15 have epigenetic effects in tumor cells, changes in H3K4 methylation in the Calu 6 human anaplastic lung tumor cell line were monitored, as shown in FIG. 4. Compound C1 did not appear to have a significant effect on H3K4 methylation at either 24 or 48 hours. However, C15 caused a significant, dose-dependent increase in H3K4me2 levels at 72 hours. Without being bound by theory, these data suggest that C15 penetrates into tumor cells, where the compound inhibits LSD1 and promotes increases in histine lysine methylation at the LSD1 substrate site.

LSD1 Inhibitor Screening Assay:

Compounds were screened as per manufacturer's guidelines (Cayman Chemical, Item #700120). In short, 10 μM of compound was combined with the fluorometic substrate 10-acetyl-3,7-dihydroxyphenoxazine, horseradish peroxidase, human recombinant LSD1, and 100 μM dimethylated lysine at residue 4 [ARTK(diMe)QTARKSTGG-KAPRKQLA] (Seq. ID No: 1) for 30 mins at 37° C. Plates were read using an excitation wavelength of 535 nm and an emission wavelength of 590 nm with a SpectraMax M5 Microplate reader.

Preparation of Cell Lysates:

Following treatment, cells were washed twice in sterile filtered cold 1×PBS. Cells were then lysed in 200 μL of lysis buffer (20 mM Tris, 150 mM NaCl, 1 mM EDTA, 1 mM EGTA, 1 mM β-glycerol, 2.5 mM sodium pyrophosphate, and 1% Triton X-100) Protease and phosphatase inhibitors were added to these buffers (1:100 dilutions of phosphatase inhibitor cocktail I and II and protease inhibitor cocktail; Sigma). The cells were then incubated on ice for 15 min, and insoluble material was pelleted by centrifugation at 4° C.

Western Blot Analysis for LSD1 Proteins:

Protein concentrations were determined by Pierce BCA protein assay kit (Thermo Sci, Product #23225). Cell lysates were subjected to SDS-PAGE, and Western blot analysis was performed with the appropriate antibodies. Primary antibodies against H3K4me2, H3K4me1, and LSD1 were from Cell Signaling; Histone H3 primary antibody was from Millipore. Proteins were visualized by enhanced chemiluminescence (ECL).

Pull-Down Experiment for HDAC1/CoREST/LSD1 Complex:

Primary feline cardiomyocytes were treated for 3 h with 5 mM verlindamycin (V), 1 mM C1 or 2 mM C15. Co-immunoprecipitation (pull down) of intact protein complexes works by selecting an antibody that targets a known protein that is believed to be a member of a larger complex of proteins. By targeting this known member with an antibody it may become possible to pull the entire protein complex out of solution and thereby identify unknown members of the complex. This works when the proteins involved in the complex bind to each other tightly, making it possible to pull multiple members of the complex out of solution by latching onto one member with an antibody. This concept of pulling protein complexes out of solution is sometimes referred to as a "pull-down". Co-immunoprecipitation is a powerful technique that is used regularly by molecular biologists to analyze protein-protein interactions. The co-repressor HDAC:CoREST:LSD1 complex was initially pulled down with an antibody for HDAC1 and a Western blot for CoREST was performed.

Langendorff Heart Model:

In the Langendorff preparation, the heart is removed with preservation of a portion of the afferent and efferent blood vessels; it is then perfused in a reverse fashion via the aorta, usually with a nutrient rich, oxygenated solution (e.g. Krebs-Henseleit solution or Tyrode's solution). The backwards pressure causes the aortic valve to shut, forcing the solution into the coronary vessels, which normally supply the heart tissue with blood. This feeds nutrients and oxygen to the cardiac muscle, allowing it to continue beating for several hours after its removal from the animal. This is a useful preparation because it allows the addition of drugs (via the perfusate) and observation of their effect on the heart without the complications involved with in vivo experimentation, such as neuronal and hormonal effects from living animal (Broadley, K. J., 1970). A pressure transducer is inserted to measure a number of cardiac performance parameters including left ventricular developed pressure, left ventricular end diastolic pressure, heart rate, etc. Following the Langendorff procedure, the myocardium is cut into cross sections, and infarcted tissue is identified by the inability to take up stain; thus infarcted areas appear white, while healthy areas appear red.

Pull-Down Experiment with LSD1 Antibody Determining LSD1:HDAC1:

Co-immunoprecipitation analysis for LSD1:CoREST complex following treatment from primary rat cardiomyocytes with 5 µM and 1 µM C1 was performed as described above. Lysates pulled down with LSD1 antibody and western blotted for CoREST (n=2).

Inhibition of Spermine Oxidase:

The assay procedure is very similar to the assay used for LSD1, except that the reaction is conducted by human recombinant spermine oxidase. the assay for C1 and related analogues was conducted as previously described (Goodwin et al., 2011).

Example 2: Synthetic Methodology and Compound Characterization

A chemical synthesis used to prepare C1 and its analogues is shown in Scheme 1. Depending on the availability of commercial starting materials, these analogues can be made in two steps. Thus the appropriate carboxylate 7 can be coupled to 4H-1,2,4-triazole-3,5-diamine 8 (DCC, HOBT, N-methylmorpholine) to form the corresponding amide 9, followed by diborane reduction of the amide carbonyl to form C1.

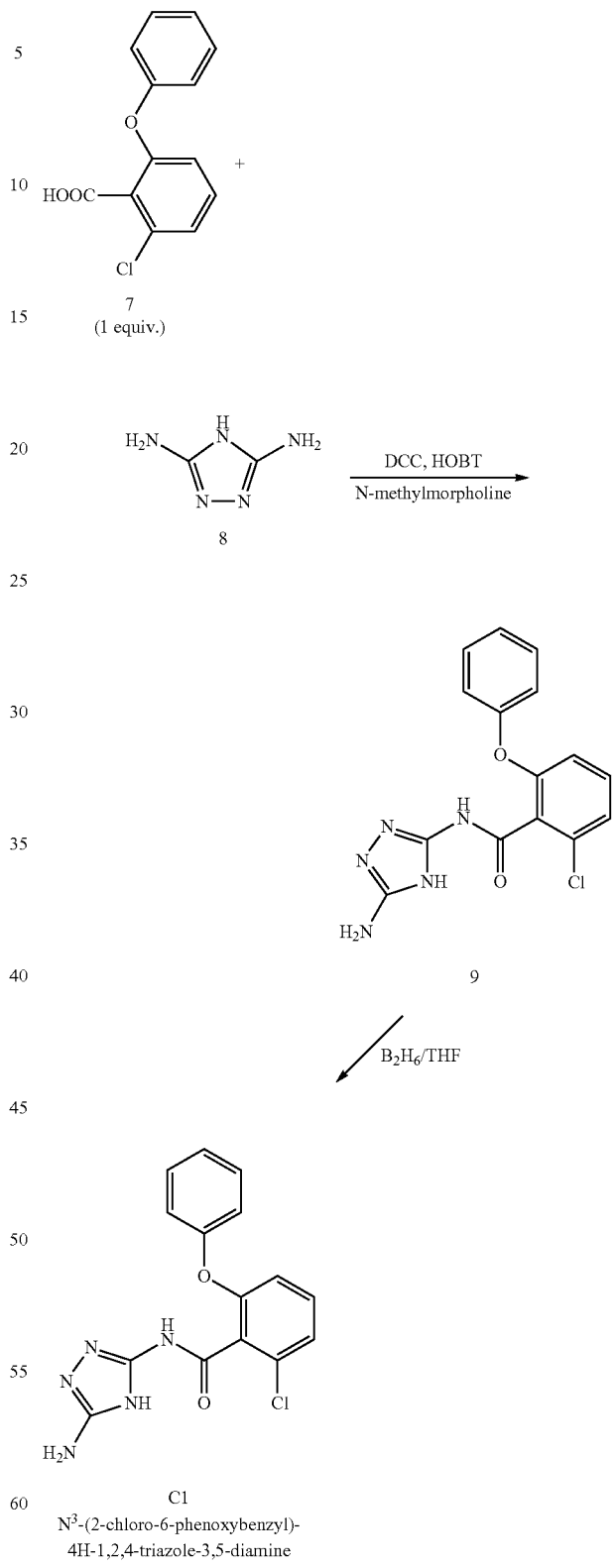

A similar approach to the preparation of C15 was developed and is shown in Scheme 2.

Scheme 2
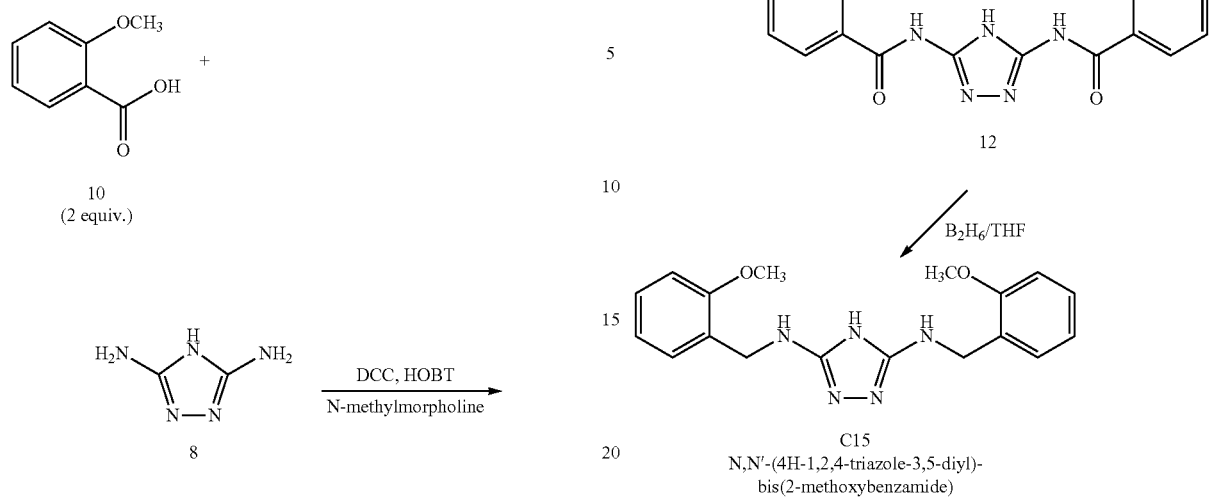
Scheme 3
Method A
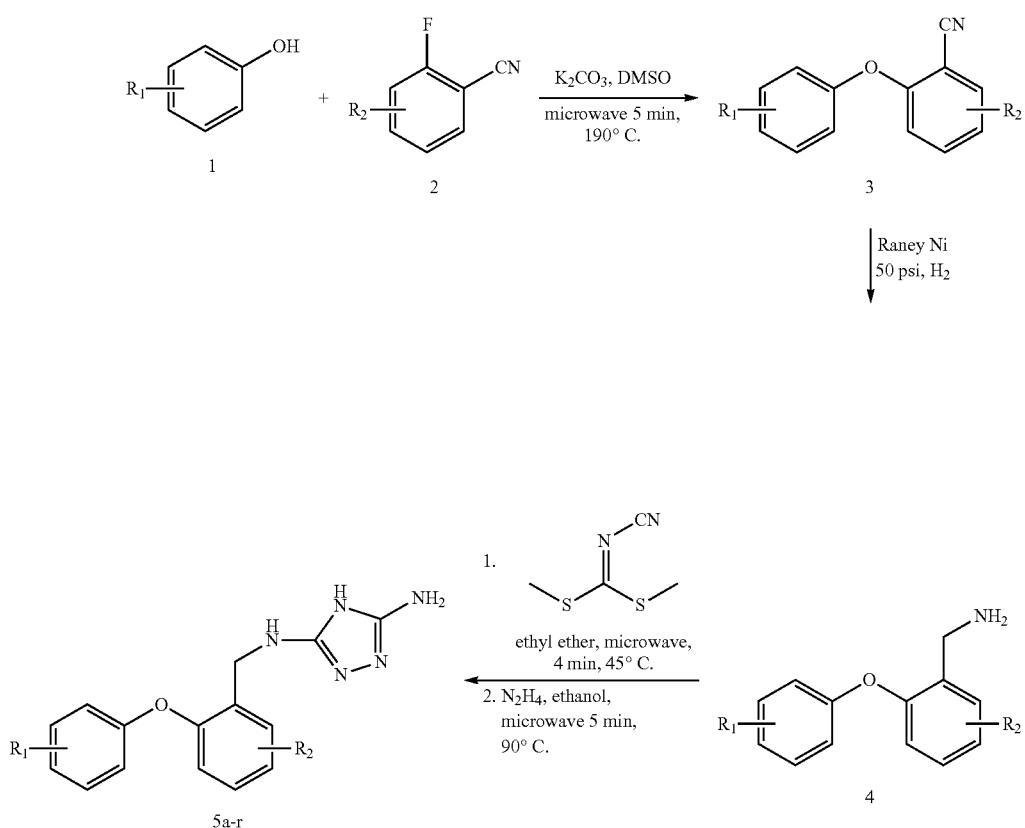

Method B

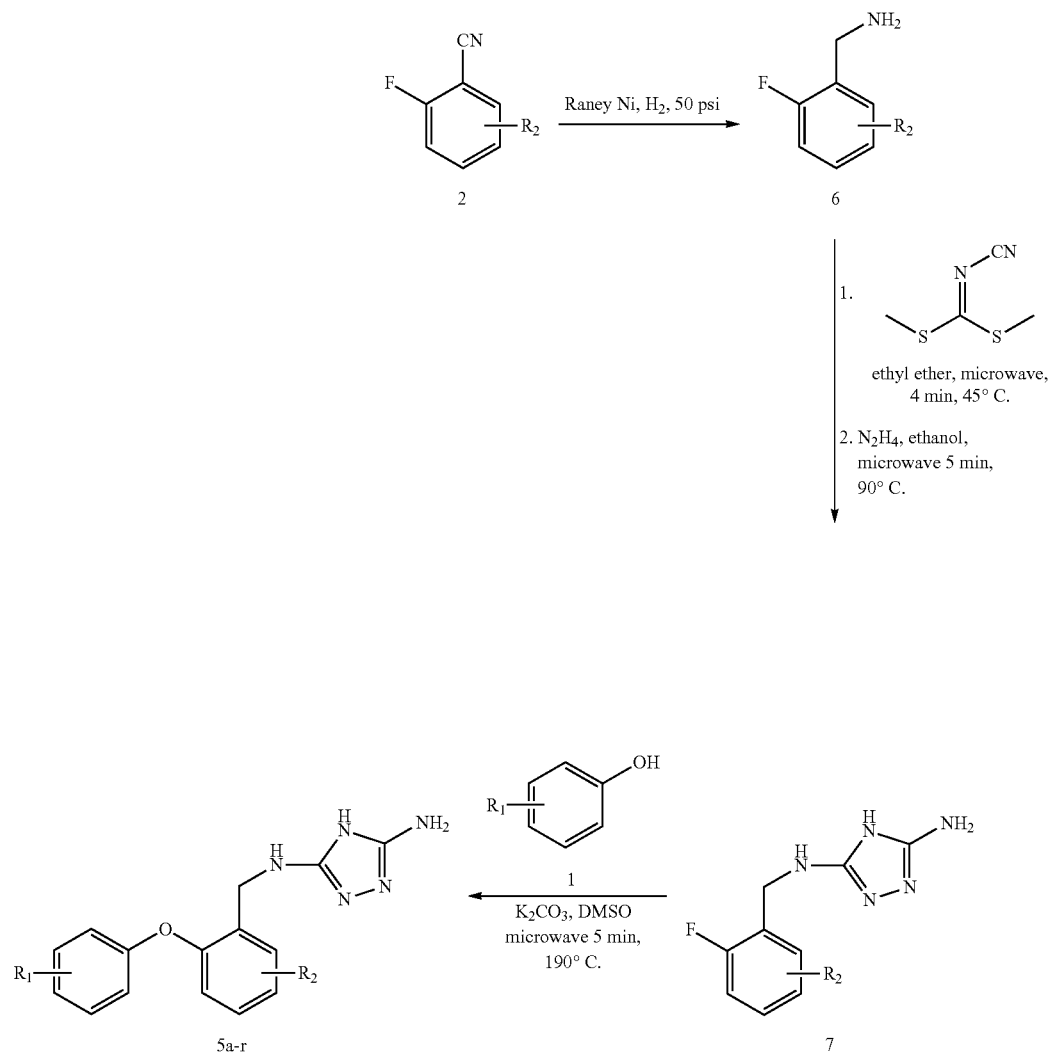

A rapid and facile synthetic route leading to C1 analogues was subsequently developed, as shown in Scheme 3. Method A: A substituted phenol 1 is coupled to a suitably substituted 2-fluorocyanobenzene 2 in the microwave using the procedure of Li, et al., which is incorporated herein by reference, (5 min, 190° C.) to afford the diarylether 3. Compound 3 is then reduced to the corresponding aminomethyl intermediate 4 (Raney Ni, $H_2$, 50 psi, ethanol, 25° C.). Intermediate 4 can then be reacted by microwave with dimethyl cyanocarbonimidodithioate using the method of Hansen, et al., which is incorporated herein by reference, (ethyl ether, 4 min, 45° C.), and the resulting intermediate is then exposed to hydrazine (ethanol, 5 min, 90° C.) to afford the desired target triazole 5a-t. Method B: Method B employs the identical reactions, except that the Raney Ni reduction is first used to convert 2 to the substituted benzyl amine 6, after which the Hansen and Li methods are applied in sequence to afford the desired target molecules 5a-t. Using the methods and synthetic schemes described in Schemes 1-4 above, the following compounds have been produced:

TABLE 2

Synthetic analogues of C1 and percent inhibition of LSD1 at 10 μM

| Compound | Structure | MW | % Inhibition of recombinant LSD1 at 10 μM |
|---|---|---|---|
| C1 | 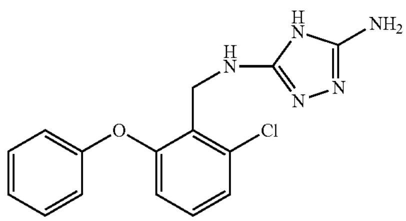 [SMILES: Nc1nnc(NCc2c(Cl)cccc2Oc2ccccc2)[nH]1] | 315.76 | 84.9 ± 4.7 |
| 5a | 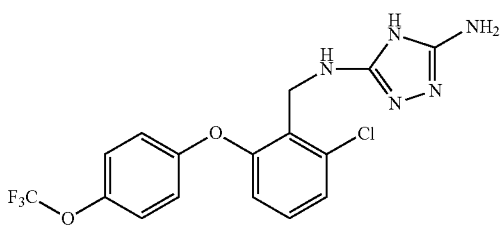 [SMILES: Nc1nnc(NCc2c(Cl)cccc2Oc2ccc(OC(F)(F)F)cc2)[nH]1] | 399.75 | 38.6 ± 5.6% |
| 5b | 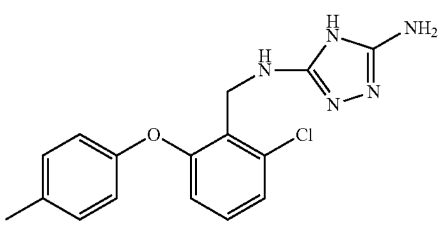 [SMILES: Cc1ccc(Oc2cccc(Cl)c2CNc2nnc(N)[nH]2)cc1] | 329.78 | 59.3 ± 6.1% |
| 5c | 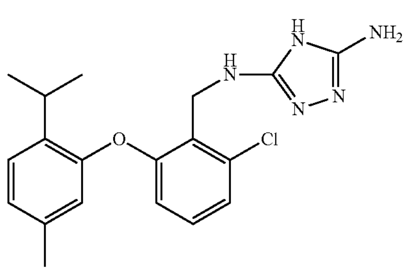 [SMILES: Cc1ccc(C(C)C)c(Oc2cccc(Cl)c2CNc2nnc(N)[nH]2)c1] | 371.86 | 56.3 ± 3.2% |
| 5d | 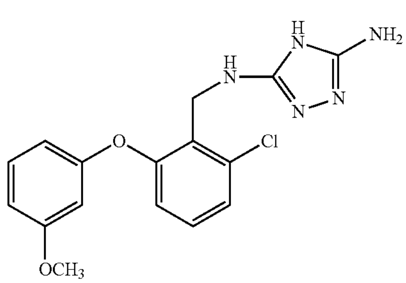 [SMILES: COc1cccc(Oc2cccc(Cl)c2CNc2nnc(N)[nH]2)c1] | 345.78 | 44.6 ± 5.1% |

TABLE 2-continued

Synthetic analogues of C1 and percent inhibition of LSD1 at 10 μM 5a-r

| Compound | Structure | MW | % Inhibition of recombinant LSD1 at 10 μM |
|---|---|---|---|
| 5e | 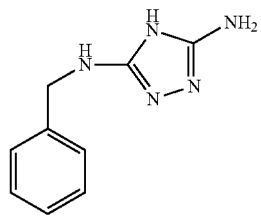 [SMILES: Nc1nnc(NCc2ccccc2)[nH]1] | 189.22 | 41.0 ± 17.4% |
| 5f | 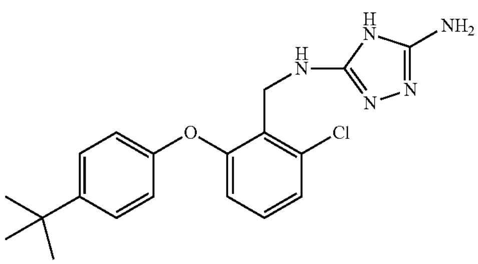 [SMILES: CC(C)(C)c1ccc(Oc2cccc(Cl)c2CNc2nnc(N)[nH]2)cc1] | 371.86 | 58.2 ± 8.8% |
| 5g | 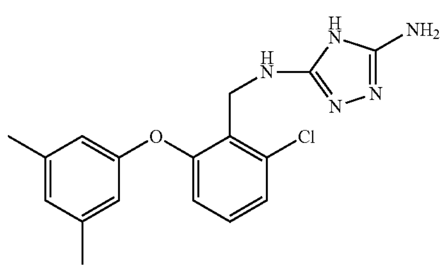 [SMILES: Cc1cc(C)cc(Oc2cccc(Cl)c2CNc2nnc(N)[nH]2)c1] | 343.81 | 67.9 ± 6.5% |
| 5h | 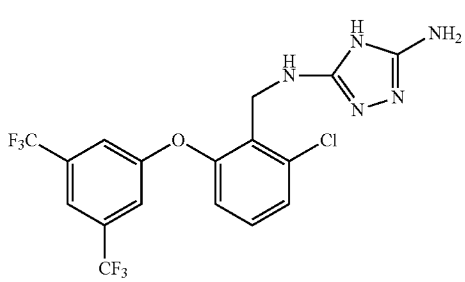 [SMILES: Nc1nnc(NCc2c(Cl)cccc2Oc2cc(C(F)(F)F)cc(C(F)(F)F)c2)[nH]1] | 451.75 | 44.9 ± 4.6% |
| 5i | 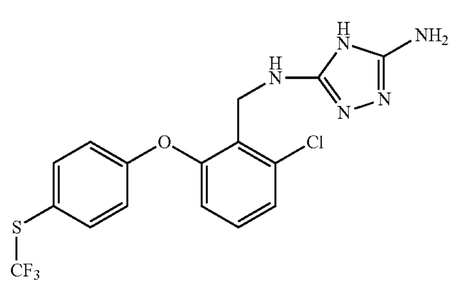 [SMILES: CSc1ccc(Oc2cccc(Cl)c2CNc2nnc(N)[nH]2)cc1] | 415.82 | Not Determined (Insoluble) |

TABLE 2-continued

Synthetic analogues of C1 and percent inhibition of LSD1 at 10 μM 5a-r

| Compound | Structure | MW | % Inhibition of recombinant LSD1 at 10 μM |
|---|---|---|---|
| 5j | (2,4-dibromophenoxy, 2-Cl benzyl triazole-amine) | 473.55 | Not Determined (Insolube) |
| 5k | (2-CF$_3$, 4-Br phenoxy, 2-Cl benzyl triazole-amine) | 462.65 | 67.8 ± 5.4% |
| 5l | (4-SCH$_3$ phenoxy, 2-Cl benzyl triazole-amine) | 361.85 | Not Determined (Insolube) |
| 5m | (2-OCH$_3$, 4-CH$_3$ phenoxy, 2-Cl benzyl triazole-amine) | 359.81 | 84.7 ± 3.2% |
| 5n | (3,5-dimethoxyphenoxy, 2-Cl benzyl triazole-amine) | 375.81 | 63.3 ± 8.6% |

TABLE 2-continued

Synthetic analogues of C1 and percent inhibition of LSD1 at 10 μM 5a-r

| Compound | Structure | MW | % Inhibition of recombinant LSD1 at 10 μM |
|---|---|---|---|
| 5p | 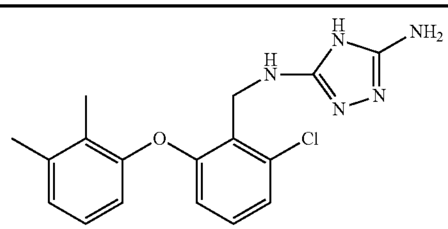 | 343.81 | 80.6 ± 1.9% |
| 5q | 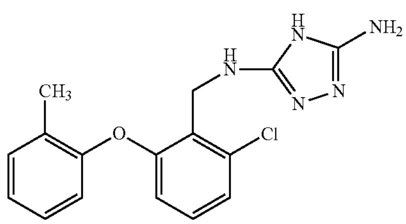 [SMILES: Cc1ccccc1Oc1cccc(Cl)c1CNc1nnc(N)[nH]1] | 329.78 | 74.2 ± 5.2% |
| 5r | 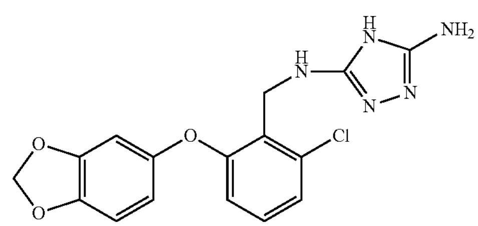 [SMILES: Nc1nnc(NCc2c(Cl)cccc2Oc2ccc3c(c2)OCO3)[nH]1] | 359.77 | 65.8 ± 6.4% |
| 5s | 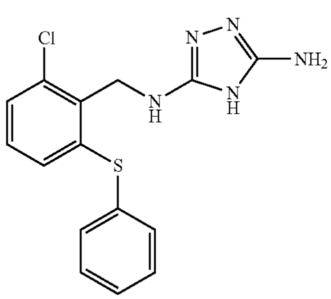 [SMILES: Nc1nnc(NCc2c(Cl)cccc2Sc2ccccc2)[nH]1] | 331.82 | 60.8 ± 3.9% |
| 5t | 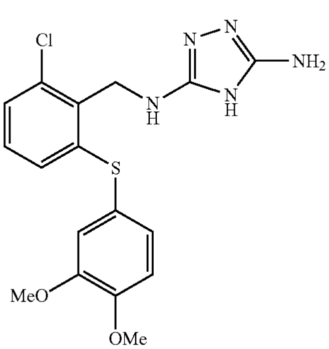 [SMILES: COc1ccc(Sc2cccc(Cl)c2CNc2nnc(N)[nH]2)cc1OC] | 391.87 | 53.2 ± 1.7% |

TABLE 2-continued
Synthetic analogues of C1 and percent inhibition of LSD1 at 10 μM
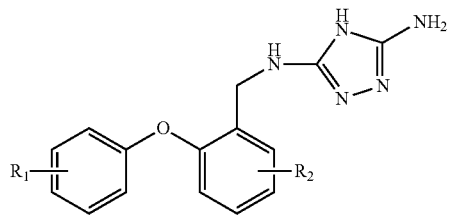
5a-r
| Compound | Structure | MW | % Inhibition of recombinant LSD1 at 10 μM |
|---|---|---|---|
| M1 | 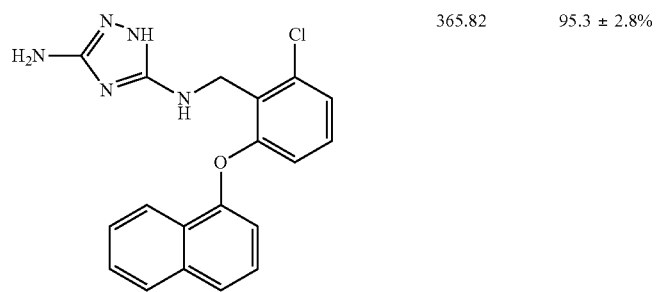 | 365.82 | 95.3 ± 2.8% |
| M2 | 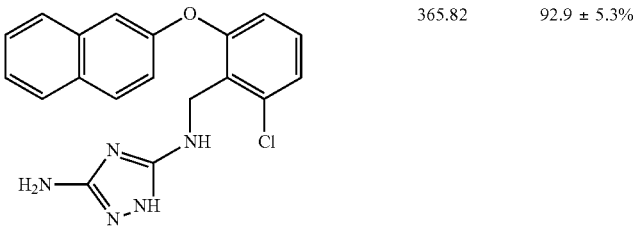 | 365.82 | 92.9 ± 5.3% |
| M3 | 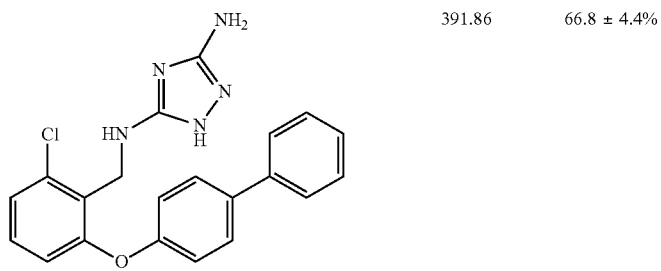 | 391.86 | 66.8 ± 4.4% |
| M4 | 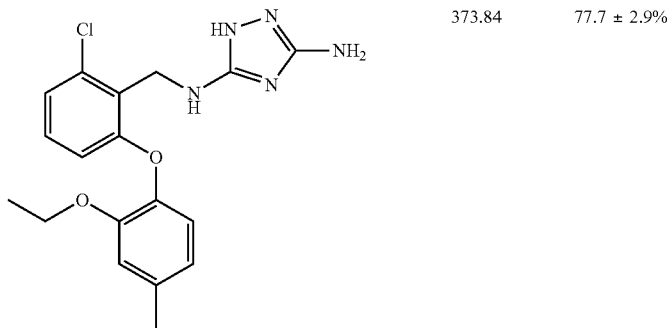 | 373.84 | 77.7 ± 2.9% |

TABLE 2-continued
Synthetic analogues of C1 and percent inhibition of LSD1 at 10 μM
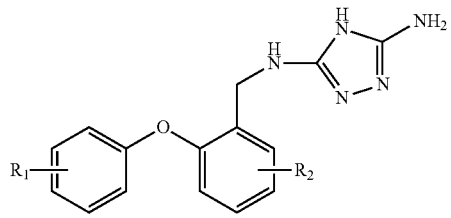
5a-r
| Compound | Structure | MW | % Inhibition of recombinant LSD1 at 10 μM |
|---|---|---|---|
| M5 | 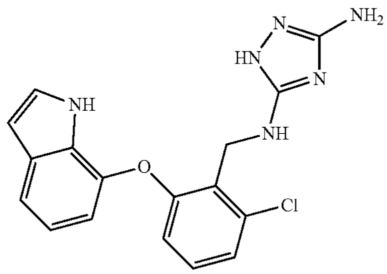 [SMILES: Nc1n[nH]c(NCc2c(Cl)cccc2Oc2cccc3cc[nH]c23)n1] | 354.80 | 67.6 ± 3.7% |
| M6 | 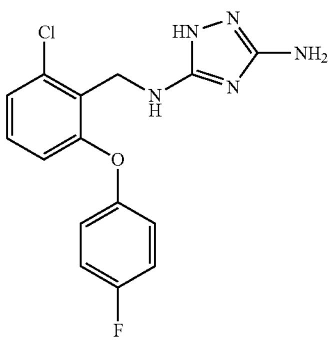 [SMILES: Nc1n[nH]c(NCc2c(Cl)cccc2Oc2ccc(F)cc2)n1] | 333.75 | 76.4 ± 2.2% |
| M7 | 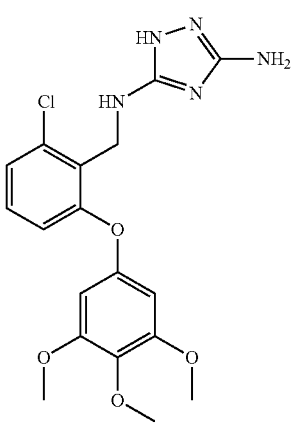 [SMILES: COc1cc(Oc2cccc(Cl)c2CNc2nc(N)n[nH]2)cc(OC)c1OC] | 405.84 | 67.6 ± 6.2% |

TABLE 2-continued
Synthetic analogues of C1 and percent inhibition of LSD1 at 10 μM
5a-r
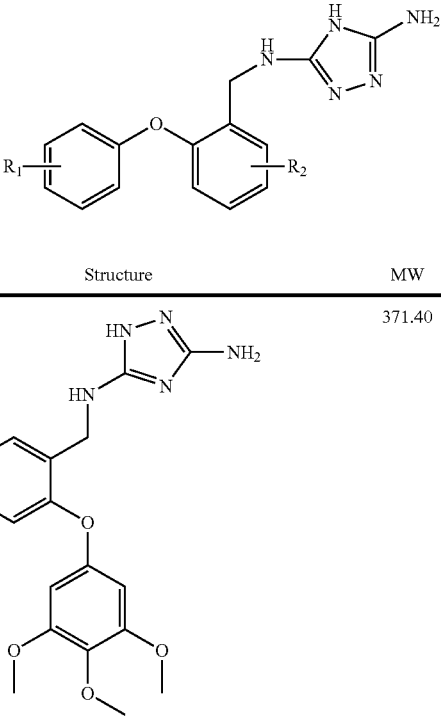
| Compound | Structure | MW | % Inhibition of recombinant LSD1 at 10 μM |
|---|---|---|---|
| M8 | 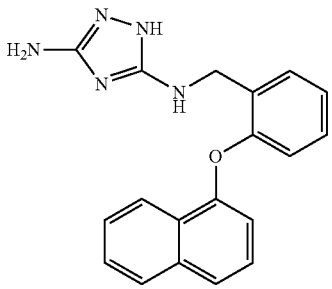 [SMILES: Nc1n[nH]c(NCc2ccccc2Oc2cccc3ccccc23)n1] | 371.40 | 56.0 ± 4.1% |
| M9 | 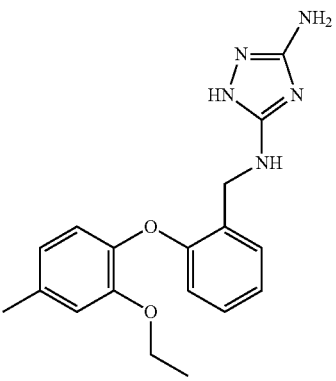 [SMILES: CCOc1cc(C)ccc1Oc1ccccc1CNc1nc(N)n[nH]1] | 331.39 | 78.1 ± 2.6% |
| M10 | 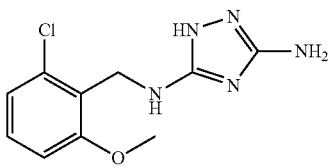 | 339.40 | 73.8 ± 4.4% |
| H1 | 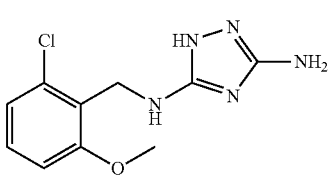 [SMILES: COc1cccc(Cl)c1CNc1nc(N)n[nH]1] | 253.69 | 73.1 ± 1.6% |

General Procedure for the Preparation of Target Molecules 5a-5r:

Synthesis of $N^3$-(2-chloro-6-phenoxybenzyl)-4H-1,2,4-triazole-3,5-diamine C1. A 0.935 g portion of benzylamine (4.0 mmol) was dissolved in 12 mL of diethyl ether and added to a 20 mL microwave vial equipped with a magnetic stir bar. A 0.702 g portion of dimethyl cyanodithioiminocarbonate (4.8 mmol) was added and the vial was sealed. The contents were microwaved at 45° C. for 5 min, cooled to room temperature, and the ether was removed in vacuo to yield the intermediate as a white to pale yellow solid. A 0.192 g portion of hydrazine hydrate (6.0 mmol) in 12 mL of dry ethanol was then injected, the vial was stirred to break up the solid intermediate, and the resulting mixture was microwaved at 90° C. for 10 min at high absorption. The ethanol was removed in vacuo to yield crude C1, which was purified on silica (9% MeOH in $CH_2Cl_2$) to afford 1.07 g of pure C1 (85%) as an off-white, amorphous solid. $^1$H-NMR (400 MHz, $CD_3OD$/TMS) δ 4.21 (s, 2H), 6.77-6.80 (dd, 1H), 6.99-7.01 (d, 2H), 7.11-7.15 (t, 1H), 7.20-7.27 (m, 2H), 7.33-7.38 (t, 2H). UPLC retention time: 12.1 min. MS calculated 315.09, found 316.33 ([M+1]$^+$).

$N^3$-(2-chloro-6-(4-(trifluoromethoxy)phenoxy)benzyl)-4H-1,2,4-triazole-3,5-diamine 5a. Compound 5a was synthesized exactly as described above in 86% yield as a white solid. $^1$H-NMR (400 MHz, $CD_3OD$/TMS) δ 4.31 (s, 2H), 6.72 (s, 1H), 6.85-6.87 (dd, 2H), 7.04-7.08 (d, 1H), 7.26-7.33 (m, 2H), 7.49 (s, 1H). UPLC retention time: 15.5 min. MS calculated 399.07, found 400.27 ([M+1]$^+$).

$N^3$-(2-chloro-6-(p-tolyloxy)benzyl)-4H-1,2,4-triazole-3,5-diamine 5b. Compound 5b was synthesized exactly as described above in 82% yield as a white solid. $^1$H-NMR (400 MHz, $CD_3OD$/TMS) δ 2.17 (s, 3H), 4.39 (s, 2H), 6.71-6.78 (m, 3H), 7.19 (d, 1H), 7.37-7.45 (m, 2H). UPLC retention time 14.4 min. MS calculated 329.79, found 330.36 ([M+1]$^+$).

$N^3$-(2-chloro-6-(2-isopropyl-5-methylphenoxy)benzyl)-4H-1,2,4-triazole-3,5-diamine 5c. Compound 5c was synthesized exactly as described above in 78% yield as a white solid. $^1$H-NMR (400 MHz, $CD_3OD$/TMS) δ 1.15-1.21 (d, 6H), 2.26 (s, 3H), 3.09-3.15 (m, 1H), 4.07 (s, 2H), 6.56-6.58 (dd, 1H), 6.97-7.00 (1H), 7.13-7.25 (m, 3H), 7.51 (s, 1H). UPLC retention time 16.0 min. MS calculated 371.15, found 372.37 ([M+1]$^+$).

$N^3$-(2-chloro-6-(3-methoxyphenoxy)benzyl)-4H-1,2,4-triazole-3,5-diamine 5d. Compound 5d was synthesized exactly as described above in 81% yield as a white solid. $^1$H-NMR (400 MHz, $CD_3OD$/TMS) δ 3.80 (s, 3H), 4.29 (s, 2H), 6.56-6.59 (dd, 1H), 6.60-6.61 (t, 1H), 6.72-6.75 (dd, 1H), 6.85-6.88 (dd, 1H), 7.25-7.32 (m, 3H). UPLC retention time 15.5 min. MS calculated 345.10, found 346.30 ([M+1]$^+$).

$N^3$-(2-(4-(tert-butyl)phenoxy)-6-chlorobenzyl)-4H-1,2,4-triazole-3,5-diamine 5f. Compound 5f was synthesized exactly as described above in 81% yield as a white solid. $^1$H-NMR (400 MHz, $CD_3OD$/TMS) δ 1.35 (s, 9H), 4.02 (s, 2H), 6.78-6.81 (dd, 1H), 6.95-6.98 (dt, 2H), 7.21-7.28 (m, 2H), 7.42-7.45 (dt, 2H). UPLC retention time 16.1 min. MS calculated 371.15, found 372.37 ([M+1]$^+$).

$N^3$-(2-chloro-6-(3,5-dimethylphenoxy)benzyl)-4H-1,2,4-triazole-3,5-diamine 5g. Compound 5g was synthesized exactly as described above in 74% yield as a white solid. $^1$H-NMR (400 MHz, $CD_3OD$/TMS) δ 2.30 (s, 6H), 4.41 (s, 2H), 6.64 (s, 2H), 6.81 (s, 2H), 7.21-7.29 (m, 2H). UPLC retention time 14.5 min. MS calculated 343.82, found 344.33 ([M+1]$^+$).

$N^3$-(2-(3,5-bis(trifluoromethyl)phenoxy)-6-chlorobenzyl)-4H-1,2,4-triazole-3,5-diamine 5h. Compound 5h was synthesized exactly as described above in 77% yield as a white solid. $^1$H-NMR (400 MHz, $CD_3OD$/TMS) δ 4.01 (S, 2H), 7.14 (S, 1H), 7.25 (S, 2H), 7.33 (S, 1H), 7.49 (S, 1H), 7.57 (S, 1H). UPLC retention time 15.4 min. MS calculated 451.76, found 452.63 ([M+1]$^+$).

$N^3$-(2-chloro-6-(4-((trifluoromethyl)thio)phenoxy)benzyl)-4H-1,2,4-triazole-3,5-diamine 5i. Compound 5i was synthesized exactly as described above in 79% yield as a white solid. $^1$H-NMR (400 MHz, $CD_3OD$/TMS) δ 4.22 (s, 2H), 7.14 (d, 1H), 7.28-7.39 (m, 5H), 7.40 (d, 1H). UPLC retention time 14.0 min. MS calculated 415.05, found 416.24 ([M+1]$^+$).

$N^3$-(2-(4-bromo-2-(trifluoromethyl)phenoxy)-6-chlorobenzyl)-4H-1,2,4-triazole-3,5-diamine 5k. Compound 5k was synthesized exactly as described above in 61% yield as a white solid. $^1$H-NMR (400 MHz, $CD_3OD$/TMS) δ 4.28 (s, 2H), 7.04 (d, 1H), 7.22 (d, 1H), 7.27 (dd, 1H), 7.44 (d, 1H), 7.55 (d, 1H), 7.71 (s, 1H). UPLC retention time 15.4 min. MS calculated 460.99, found 462.18 ([M+1]$^+$).

$N^3$-(2-chloro-6-(4-((methyl)thio)phenoxy)benzyl)-4H-1,2,4-triazole-3,5-diamine 5l. $^1$H-NMR (400 MHz, $CD_3OD$/TMS) δ 2.32 (s, 3H), 4.07 (s, 2H), 7.14 (d, 1H), 7.31 (m, 2H), 7.39-7.47 (m, 2H), 7.55 (d, 1H). UPLC retention time 14.6 min. MS calculated 361.08, found 362.23 ([M+1]$^+$).

$N^3$-(2-chloro-6-(2-methoxy-4-methylphenoxy)benzyl)-4H-1,2,4-triazole-3,5-diamine 5m. Compound 5m was synthesized exactly as described above in 40% yield as a white solid. $^1$H-NMR (400 MHz, $CD_3OD$/TMS) δ 2.40 (s, 3H), 3.75 (s, 3H), 6.54-6.57 (m, 3H), 6.83-6.88 (d, 1H), 7.06-7.18 (m, 2H). UPLC retention time 14.7 min. MS calculated 359.11, found 360.29 ([M+1]$^+$).

$N^3$-(2-chloro-6-(3,5-dimethoxyphenoxy)benzyl)-4H-1,2,4-triazole-3,5-diamine 5n. Compound 5n was synthesized exactly as described above in 76% yield as a white solid. $^1$H-NMR (400 MHz, $CD_3OD$/TMS) δ 3.75 (s, 6H), 6.14 (s, 1H), 6.22 (s, 2H), 6.90 (d, 1H), 7.26-7.33 (m, 2H). UPLC retention time 14.1 min. MS calculated 375.11, found 376.29 ([M+1]$^+$).

$N^3$-(2-chloro-6-(2,3-dimethylphenoxy)benzyl)-4H-1,2,4-triazole-3,5-diamine 5p. Compound 5p was synthesized exactly as described above in 43% yield as a white solid. $^1$H-NMR (400 MHz, $CD_3OD$/TMS) δ 2.14-2.21 (m, 3H), 2.35-2.37 (m, 3H), 6.52 (d, 1H), 6.73-6.79 (m, 3H), 7.01-7.20 (m, 2H). UPLC retention time 15.0 min. MS calculated 343.12, found 344.33 ([M+1]$^+$).

$N^3$-(2-(benzo[d][1,3]dioxol-5-yloxy)-6-chlorobenzyl)-4H-1,2,4-triazole-3,5-diamine 5r. Compound 5r was synthesized exactly as described above in 80% yield as a white solid. $^1$H-NMR (400 MHz, $CD_3OD$/TMS) δ 4.41 (s, 2H), 5.51 (s, 2H), 6.00 (s, 1H), 6.99-7.11 (m, 3H), 7.33-7.39 (m, 2H). UPLC retention time 13.7 min. MS calculated 359.08, found 360.25 ([M+1]$^+$).

$N^3$-(2-chloro-6-(phenylthio)benzyl)-4H-1,2,4-triazole-3,5-diamine 5s. Compound 5s was synthesized exactly as described above in 91% yield as a white solid. $^1$H-NMR (400 MHz, $CD_3OD$/TMS) δ 4.31 (s, 2H), 7.19 (m, 1H), 7.36-7.44 (m, 6H), 7.61 (d, 1H). UPLC retention time 14.2 min. MS calculated 331.07, found 332.28 ([M+1]$^+$).

$N^3$-(2-chloro-6-((3,4-dimethoxyphenyl)thio)benzyl)-4H-1,2,4-triazole-3,5-diamine 5t. Compound 5t was synthesized exactly as described above in 82% yield as a white solid. $^1$H-NMR (400 MHz, $CD_3OD$/TMS) δ 3.67 (s, 6H), 4.40 (s, 2H), 6.56 (m, 2H), 7.04 (m, 2H), 7.39 (d, 1H), 7.49 (d, 1H). UPLC retention time 13.7 min. MS calculated 391.09, found 392.29 ([M+1]$^+$).

Example 3: Cardiac Reperfusion Injury

Figure 6:
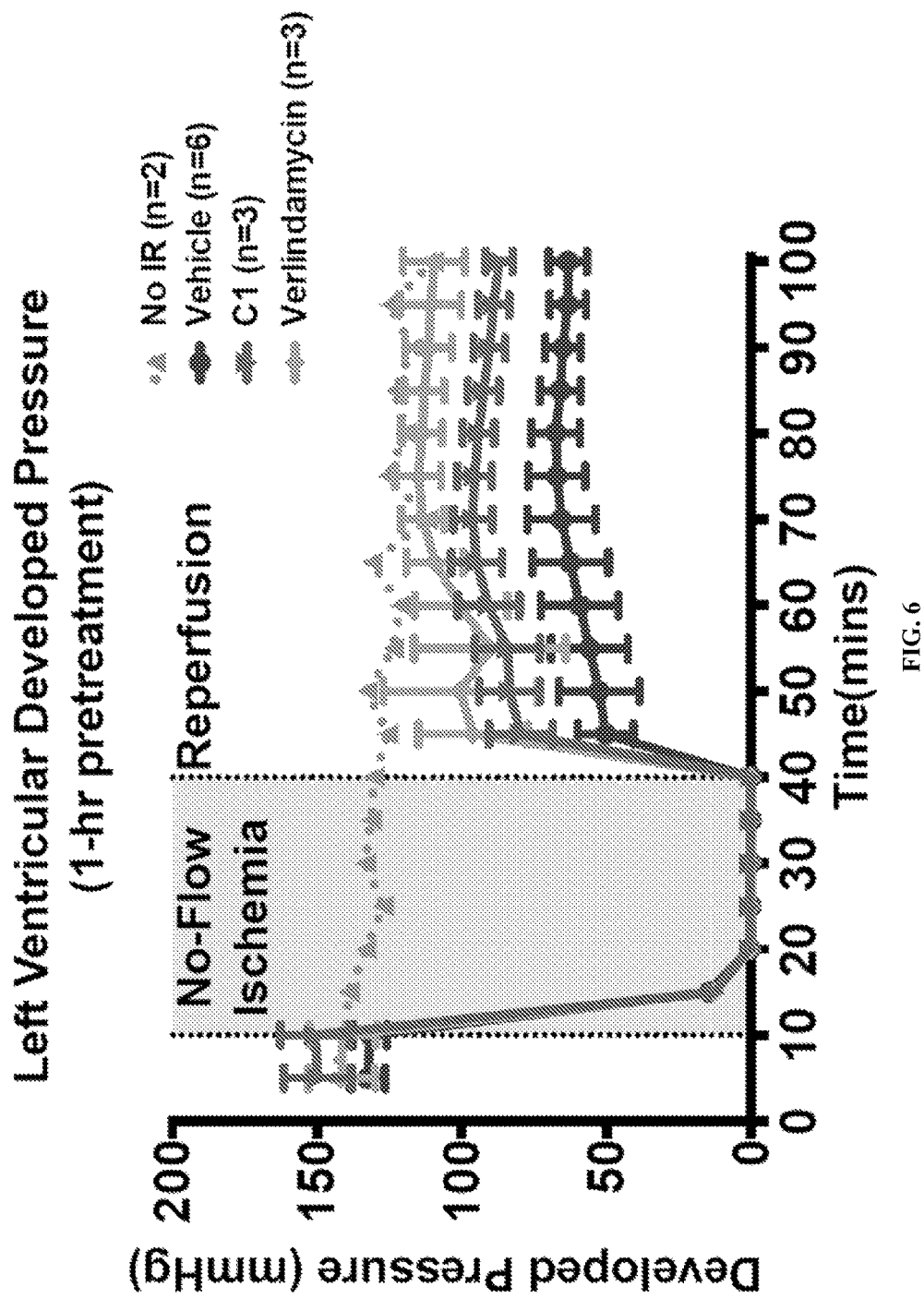
FIG. 6—Graph of left ventricular developed pressure (mm Hg) as a function of time in minutes following a 1-hour pre-treatment with C1 or verlindamycin using the Langendorff heart model. The developed pressure was higher than the vehicle for both verlindamycin and C1 after reperfusion began.
Figure 7:
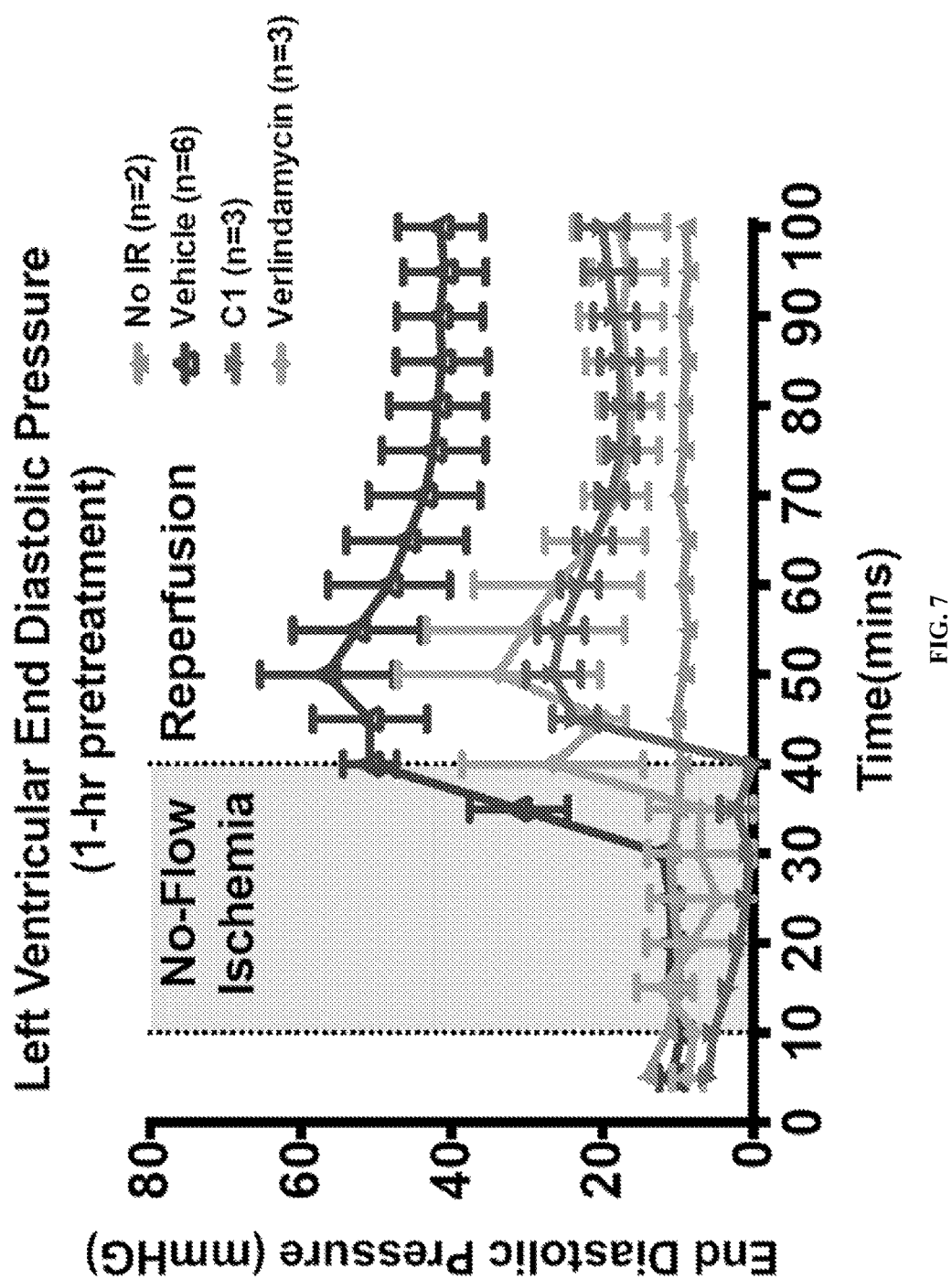
FIG. 7—Left ventricular end diastolic pressure (mm Hg) as a function of time following a 1 hour pre-treatment with 1.0 μM C1 or verlindamycin in the Langendorff isolated heart model. Both compounds were more effective than vehicle in restoring normal left ventricular developed pressure following reperfusion of the ischemic myocardium.
Figure 8:
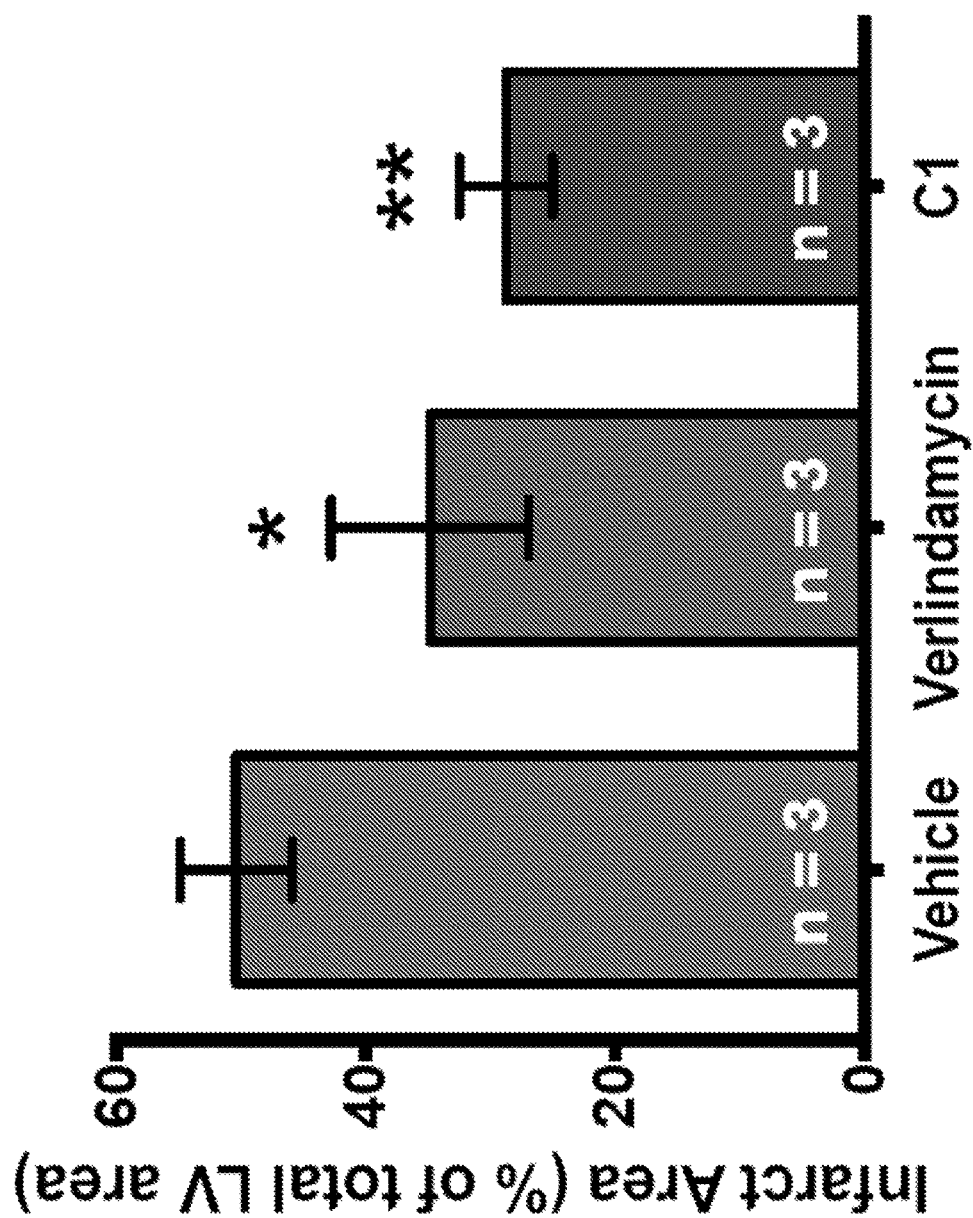
FIG. 8—Infarct area as a percentage of the total left ventricular area in the murine myocardium. Both verlindamycin (10 mg/kg) and C1 (10 mg/kg) were significantly more effective than treatment with vehicle. * is p-value <0.05 and ** is p-value <0.01.
Figure 9:
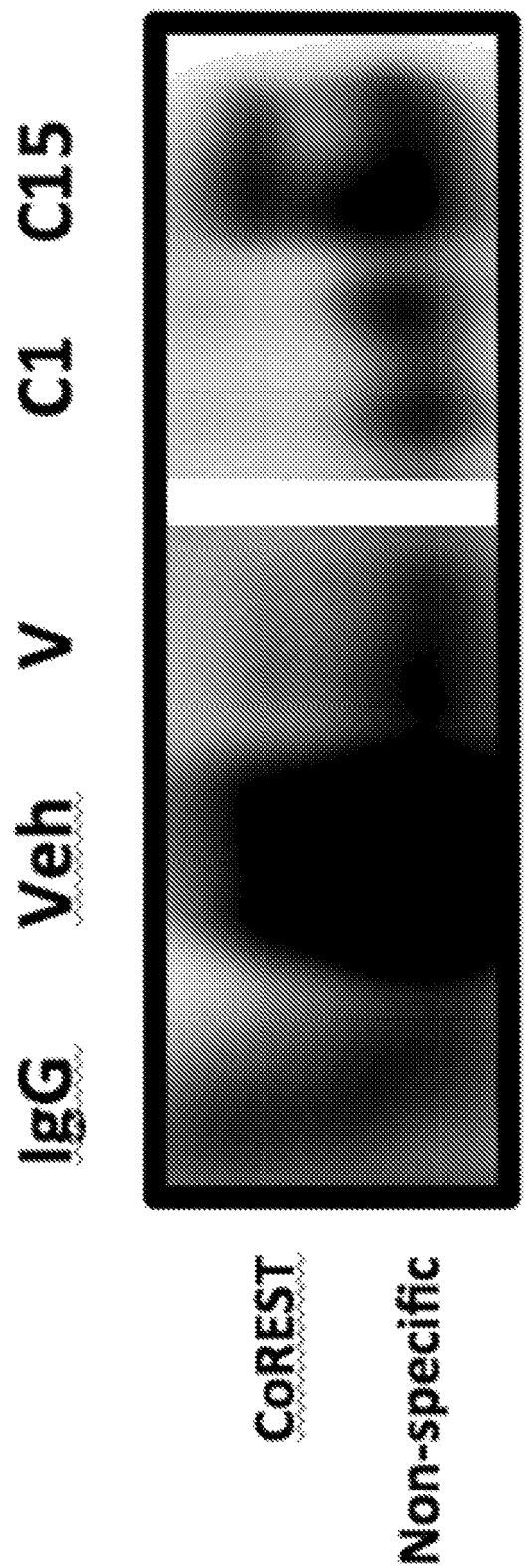
FIG. 9—Primary feline cardiomyocytes were treated for 3 h with 5 μM compound C1 or C15. The HDAC1/CoREST/LSD1 complex was pulled down with an HDAC1 antibody and a Western blot for CoREST was performed. Both C1 and C15 disrupted the association of HDAC1 and CoREST.
Figure 10:
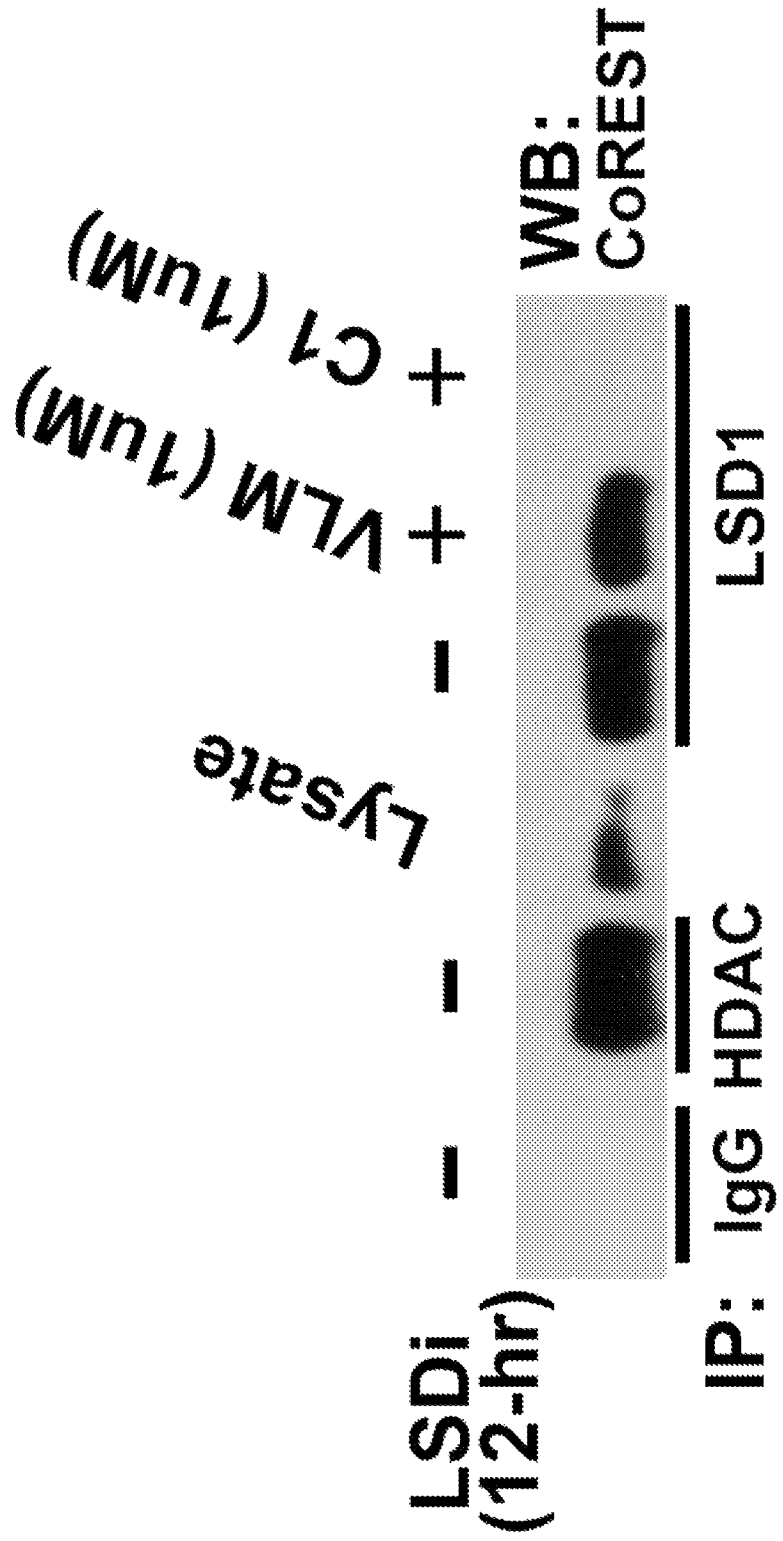
FIG. 10—Primary feline cardiomyocytes were treated for 3 h with 1 μM verlindamycin (VLM) or compound C1. The HDAC1/CoREST/LSD1 complex was pulled down with an LSD1 antibody and a Western blot for CoREST was performed. Only compound C1 disrupted the association between LSD1 and CoREST.

The compounds described herein may be used to protect the myocardium from injury following an ischemic event. In FIG. 6, a mouse heart was subjected to ischemia by ligation of the afferent vessel in a Langendorff preparation, as described above. Prior to the induction of ischemia, hearts were either pre-treated with vehicle, verlindamycin or C1. The treated hearts showed significantly better recovery from ischemia, in that the left ventricular developed pressure was restored to nearly normal levels. Similarly, left ventricular end diastolic pressure (FIG. 7) was reduced to near-normal levels in treated hearts, but not in hearts treated with vehicle. In FIG. 8, the results of an experiment to measure infarcted tissue in a myocardial cross-section are shown. Results are expressed as a percentage of the area of infarct with respect to total surface area. As shown in the figure, C1 was most effective in limiting the spread of infarct following induced myocardial ischemia. FIG. 9 shows the results of a co-immunoprecipitation experiment wherein HDAC1/CoREST/LSD1 complex was pulled down with an HDAC1 antibody and a Western blot for CoREST was performed. Both C1 and C15 disrupted the association of HDAC1 and CoREST, although C1 was more effective. Without wishing to be bound by any theory, FIG. 9 suggests that LSD1 inhibition may cause disruption of the entire co-repressor complex leading to its cardioprotective effects. FIG. 10 shows the result of an experiment wherein primary feline cardiomyocytes were treated for 3 h with 1 µM verlindamycin (VLM) or 1 µM compound C1. The HDAC1/CoREST/LSD1 complex was pulled down with an LSD1 antibody and a Western blot for CoREST was performed. Compound C1 disrupted the association between LSD1 and CoREST.

Example 4: Inhibition of Spermine Oxidase

Figure 11:
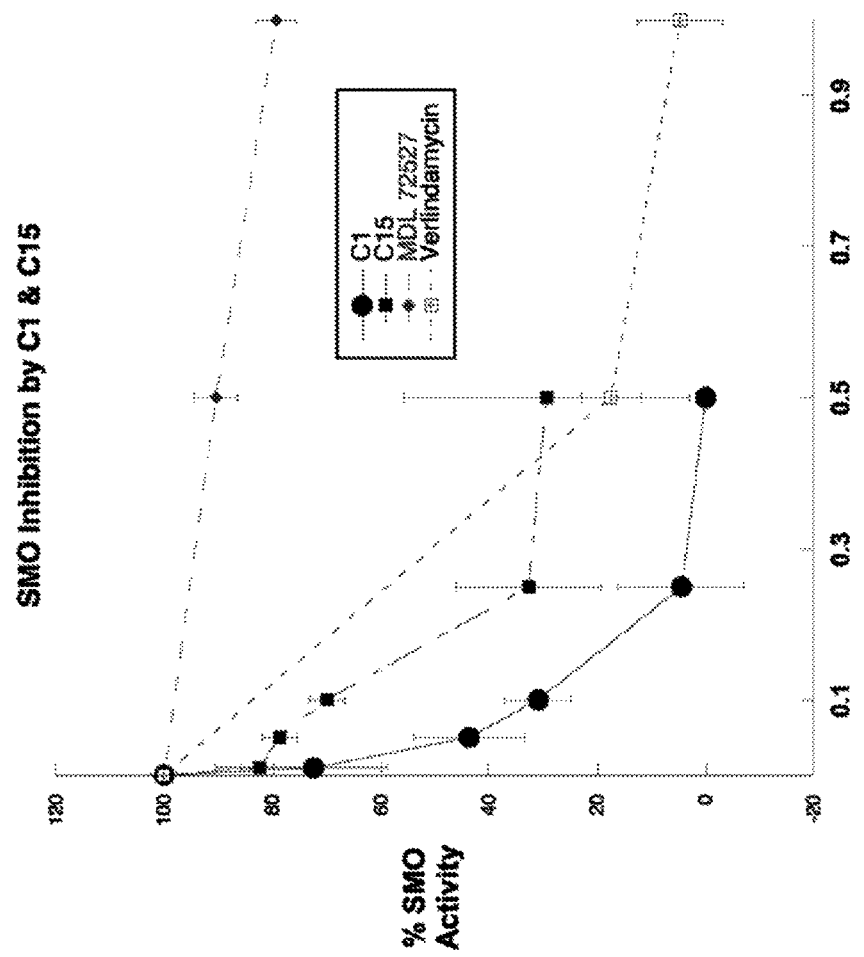
FIG. 11—Comparison of the IC$_{50}$ values for inhibition of human recombinant spermine oxidase by C1, C15, the known spermine oxidase inhibitor MDL72527 and verlindamycin. Compounds were assayed at concentrations between 0.1 and 1.0 μM. The IC$_{50}$ for C1 against spermine oxidase is 40 nM.

The compounds described herein have been shown to also inhibit spermine oxidase (SMOX). FIG. 11 shows a comparison of the $IC_{50}$ values for inhibition of human recombinant spermine oxidase by C1, C15, the known spermine oxidase inhibitor MDL72527, and verlindamycin. Each of these compounds was assayed at concentrations between 0.1 and 1.0 µM. Both C1 and C15 showed improved inhibition of spermine oxidase over verlindamycin. Compound C1 was a competitive inhibitor of the amine oxidase enzyme spermine oxidase (SMOX), with an $IC_{50}$ value of 40 nM. Without wishing to be bound by any theory, spermine oxidase inhibitors may be useful as therapeutic agents for gastric cancers. Spermine oxidase has been implicated in the development of gastric cancer in patients who experience chronic *Helicobacter pylori* infections (Chaturvedi, et al., 2014).

All of the compounds, compositions and methods disclosed and claimed herein can be made and executed without undue experimentation in light of the present disclosure. While the disclosure may have only been described in terms of certain embodiments, it will be apparent to those of skill in the art that variations may be applied to the compounds, compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

PCT Application No. 2010/084160
PCT Application No. 2011/131697
Broadley, *Brit. J. Pharmacol.*, 40(4):617-629, 1970.
Chandrasekaran, et al., *FASEB J.*, 23(11):3851-64, 2009.
Chaturvedi, et al., *Oncogene*, 1 Sep. 2014, Epub. online.
Culhane, et al., *J. Am. Chem. Soc.*, 128(14):4536-4537, 2006.
Culhane, et al., *J. Am. Chem. Soc.*, 132(9):3164-3176, 2010.
Duan, et al., *Eur. J. Med. Chem.*, 64:99-110, 2013a.
Duan, et al., *Eur. J. Med. Chem.*, 62, 11-19, 2013b.
Forneris, et al., *J. Biol. Chem.*, 280(50):41360-41365, 2005.
Forneris, et al., *J. Biol. Chem.*, 282(28):20070-20074, 2007.
Goodwin, et al., *Meth. Mol. Biol.*, 720:173-181, 2011.
*Handbook of Pharmaceutical Salts: Properties, and Use*, Stahl and Wermuth Eds., Verlag Helvetica Chimica Acta, 2002.
Hansen, F. K. et al., *Heterocycles*, 84(1):515-526, 2012.
Hayami, et al., *Int. J. Cancer*, 128(3):574-586, 2011.
Hazeldine, et al., *J. Med. Chem.*, 55(17):7378-7391, 2012.
Huang, et al., *Proc. Natl. Acad. Sci. USA*, 104:8023-8028, 2007.
Jenuwein and Allis, *Science*, 293(5532):1074-1080, 2001.
Jones, et al., *J. Mol. Biol.*, 245(1):43-53, 1995.
Kolb, et al., *Angew. Chem. Int. Ed. Engl.*, 40(11):2004-2021, 2001.
Latham and Dent, *Nat. Struct. Mol. Biol.*, 14(11):1017-1024, 2007.
Li, F. et al., *Org. Lett.*, 5(12):2169-2171, 2003
Lim, et al., *Carcinogenesis*, 31(3):512-520, 2010.
*March's Advanced Organic Chemistry: Reactions, Mechanisms, and Structure*, 2007.
Rotili and Mai, *Genes Cancer*, 2(6):663-679, 2011.
Schulte, et al., *Cancer Res.*, 69(5):2065-2071, 2009.
Sharma, et al., *J. Med. Chem.*, 53(14):5197-5212, 2010.
Sharma, et al., *Med Chem Comm*, 3:14-21, 2012.
Shi, et al., *Cell*, 119(7):941-953, 2004.
Shi, *Nat. Rev. Genet.*, 8(11):829-833, 2007.
Stavropoulos and Hoelz, *Expert Opin. Ther. Targets*, 11(6): 809-820, 2007.
Strahl and Allis, *Nature*, 403(6765):41-45, 2000.
Szewczuk, et al., *Biochemistry*, 46(23):6892-6902, 2007.
Yang, et al., *Nat. Struct. Mol. Biol.*, 14(6):535-539, 2007.
Zheng, et. al., *J. Med. Chem.*, 2013.

What is claimed is:

1. A compound of the formula:

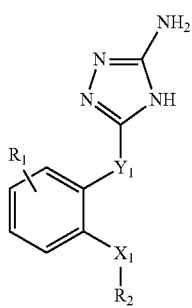

(I)

wherein:

$R_1$ is halo, hydroxy, amino, nitro, cyano, alkyl$_{(C≤12)}$, or substituted alkyl$_{(C≤12)}$;

$Y_1$ is alkanediyl$_{(C≤12)}$, alkylaminodiyl$_{(C≤12)}$, alkoxydiyl$_{(C≤12)}$, or a substituted version of any of these groups;

$X_1$ is —O—, —S—, or —NR$_3$—, wherein $R_3$ is hydrogen or alkyl$_{(C≤6)}$; and $R_2$ is aryl$_{(C≤12)}$, aralkyl$_{(C≤12)}$, heteroaryl$_{(C≤12)}$, heteroaralkyl$_{(C≤12)}$, or a substituted version of any of these groups;

provided that $R_2$ is not phenyl when $X_1$ is —O—;

or a pharmaceutically acceptable salt or tautomer thereof.

2. The compound of claim 1, wherein the formula is further defined as:

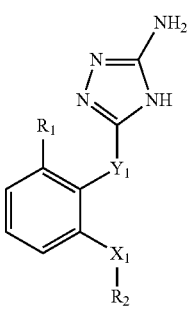

(II)

wherein:

$R_1$ is halo, hydroxy, amino, nitro, cyano, alkyl$_{(C≤12)}$, or substituted alkyl$_{(C≤12)}$;

$Y_1$ is alkanediyl$_{(C≤12)}$, alkylaminodiyl$_{(C≤12)}$, alkoxydiyl$_{(C≤12)}$, or a substituted version of any of these groups;

$X_1$ is —O—, —S—, or —NR$_3$—, wherein $R_3$ is hydrogen or alkyl$_{(C≤6)}$;

$R_2$ is aryl$_{(C≤12)}$, aralkyl$_{(C≤12)}$, heteroaryl$_{(C≤12)}$, heteroaralkyl$_{(C≤12)}$, or a substituted version of any of these groups;

provided that $R_2$ is not phenyl when $X_1$ is —O—;

or a pharmaceutically acceptable salt of tautomer thereof.

3. The compound of claim 1, wherein $R_1$ is halo.

4. The compound of claim 3, wherein $R_1$ is —Cl.

5. The compound of claim 1, wherein $X_1$ is —O—.

6. The compound of claim 1, wherein $R_2$ is aryl$_{(C≤12)}$.

7. The compound of claim 6, wherein $R_2$ is 1-napthyl or 2-napthyl.

8. The compound of claim 1, wherein the formula is selected from:

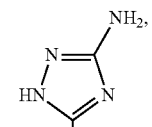

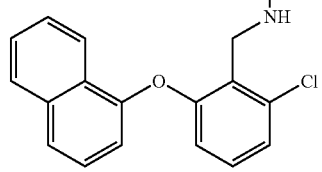

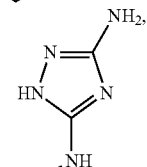

85
-continued
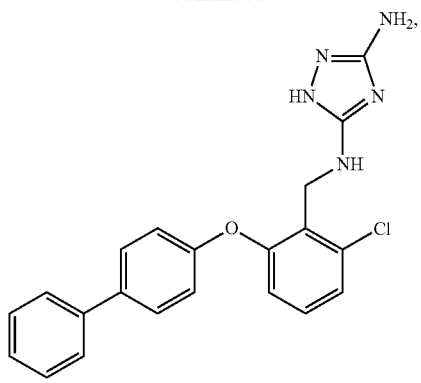
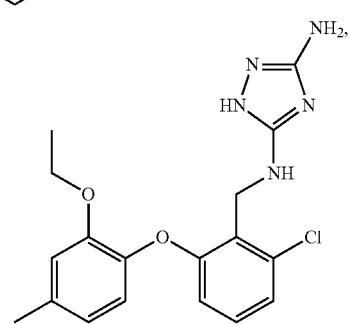
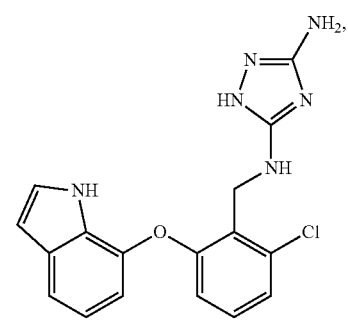
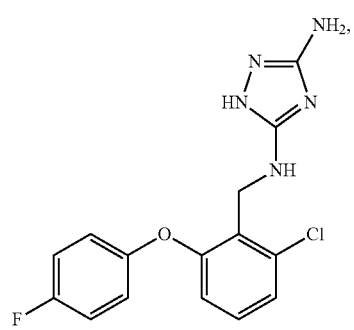
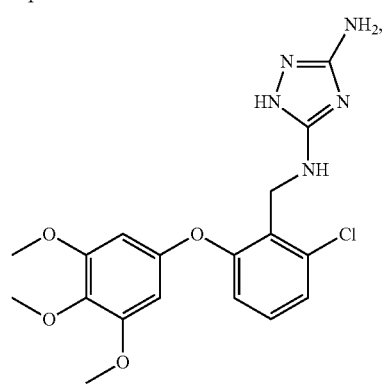
86
-continued
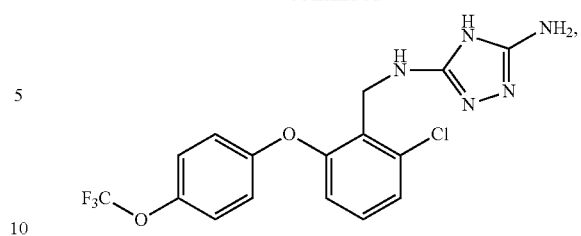
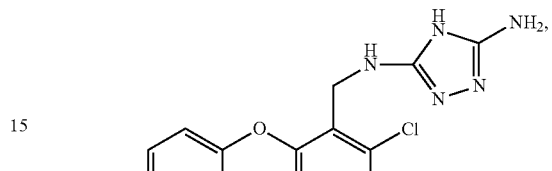
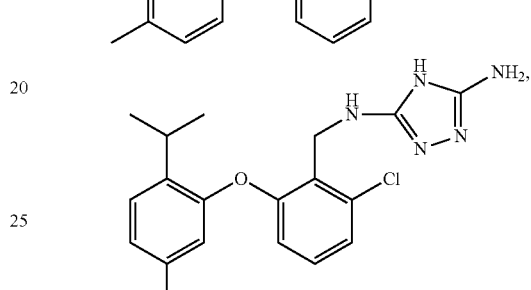
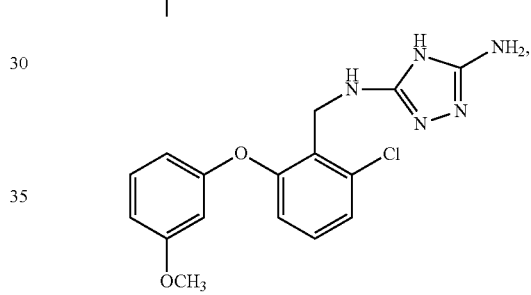
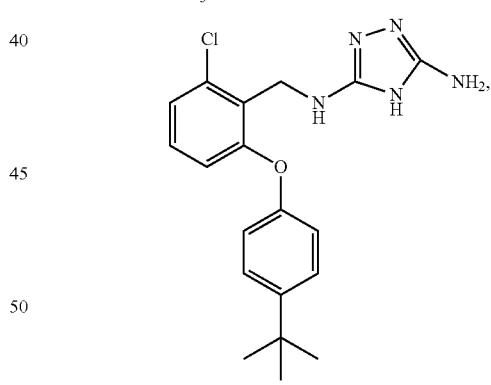
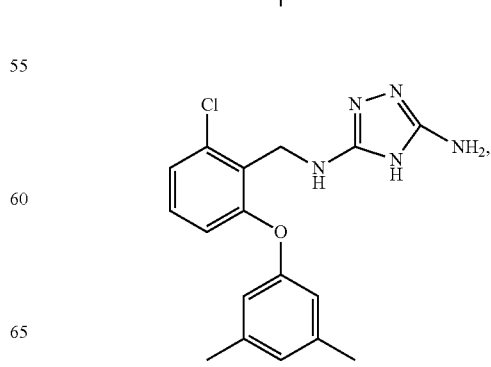

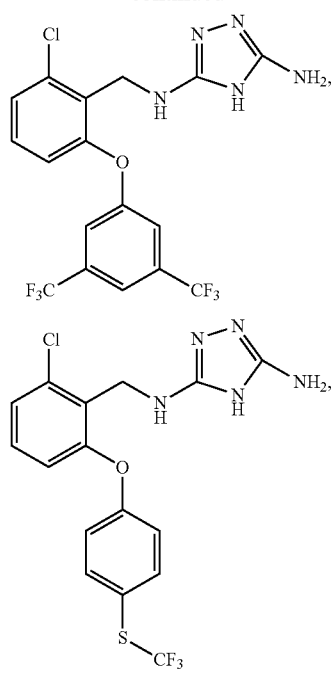
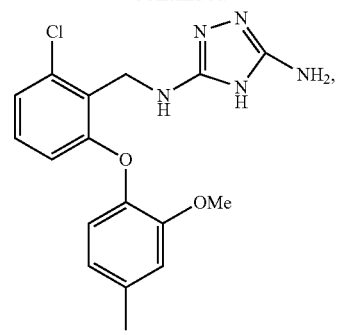
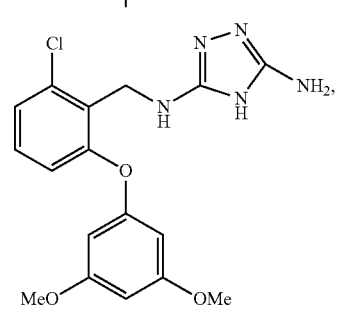
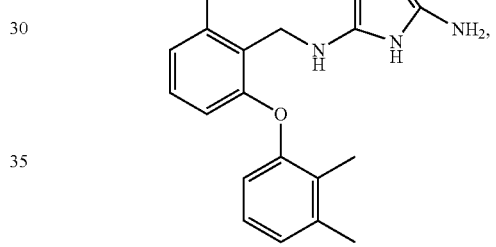
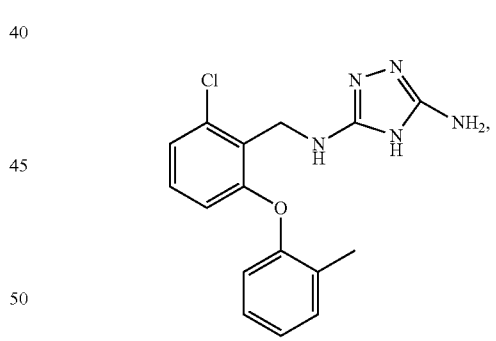
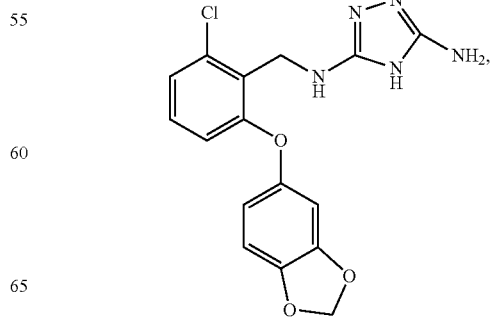

89

-continued

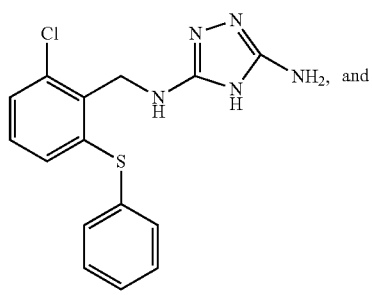

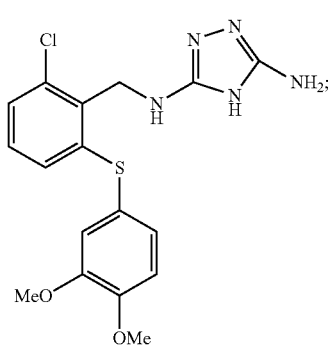

or a pharmaceutically acceptable salt or tautomer thereof.

9. A compound of the formula:

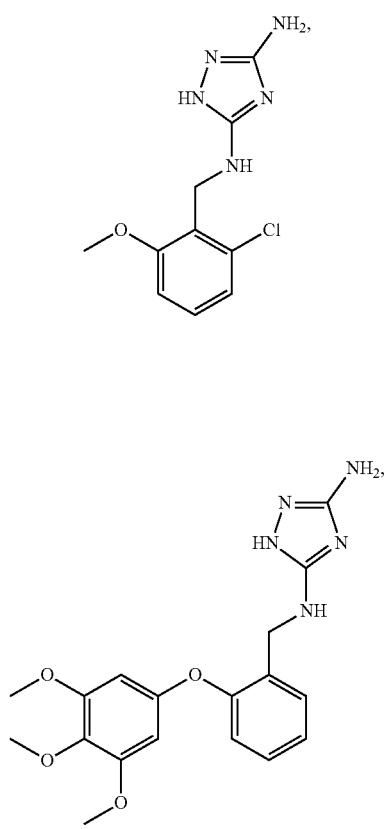

90

-continued

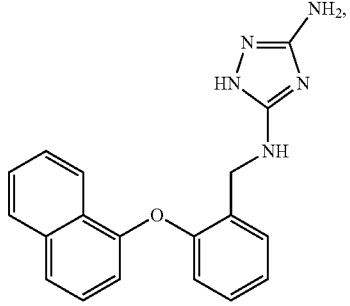

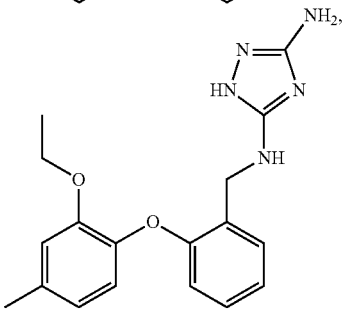

or a pharmaceutically acceptable salt thereof.

10. A pharmaceutical composition comprising a compound of claim 1 and an excipient.

11. A method of treating a cardiac reperfusion injury comprising administering to a patient a therapeutically effective amount of a compound of claim 1.

12. The method of claim 11, wherein $R_1$ is halo.

13. The method of claim 11, wherein $Y_1$ is alkylaminodiyl$_{(C \leq 12)}$.

14. The method of claim 11, wherein $X_1$ is —O—, —S—, or —NH—.

15. The method of claim 11, wherein $R_2$ is aryl$_{(C \leq 12)}$ or substituted aryl$_{(C \leq 12)}$.

16. The method of claim 11, wherein the compound is selected from:

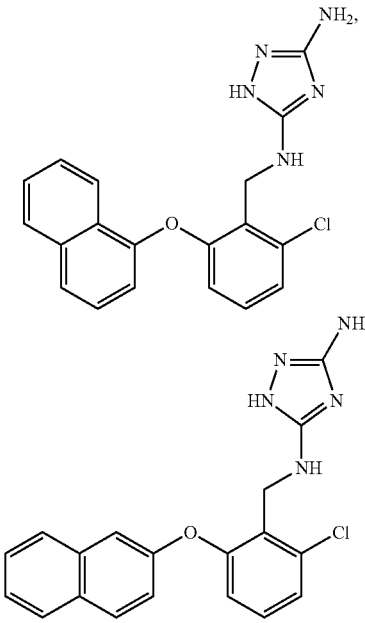

-continued
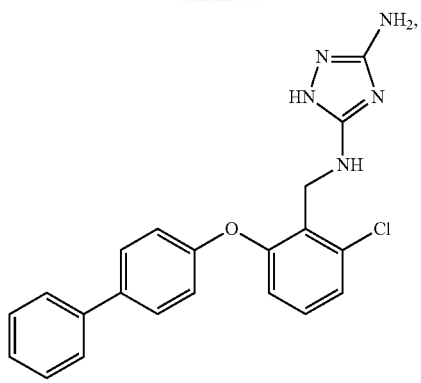
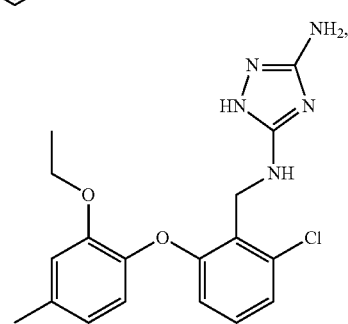
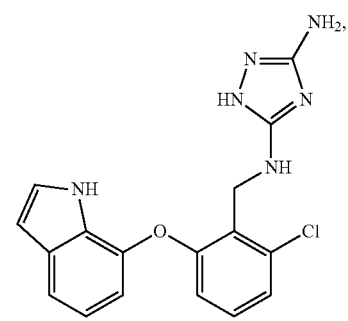
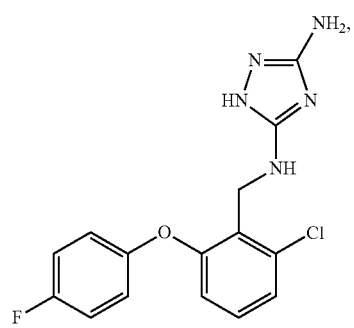
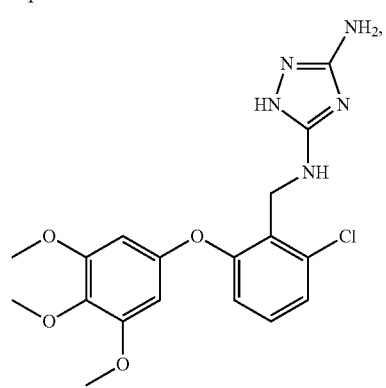
-continued
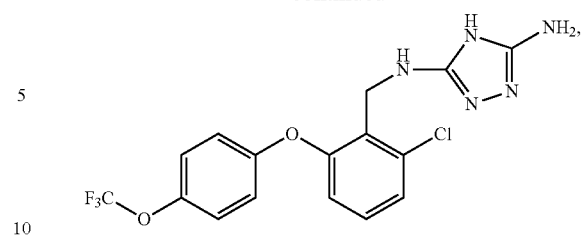
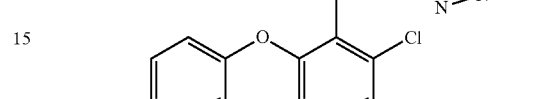
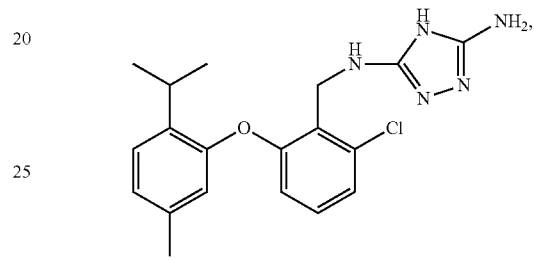
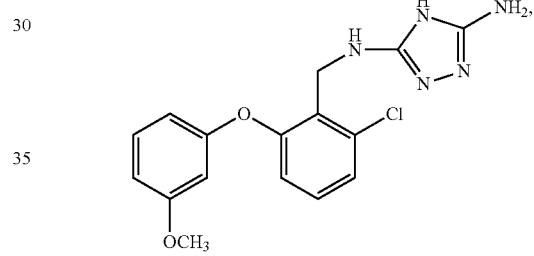
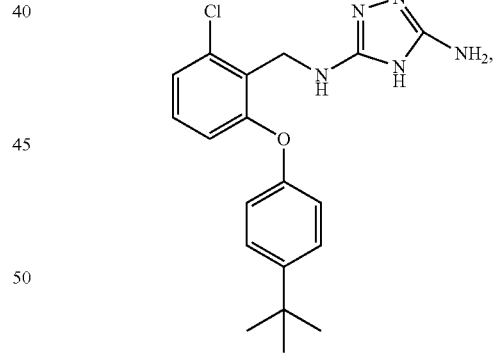
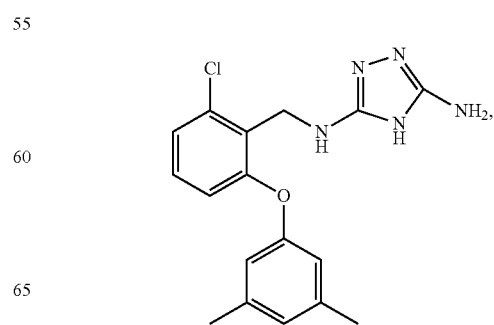

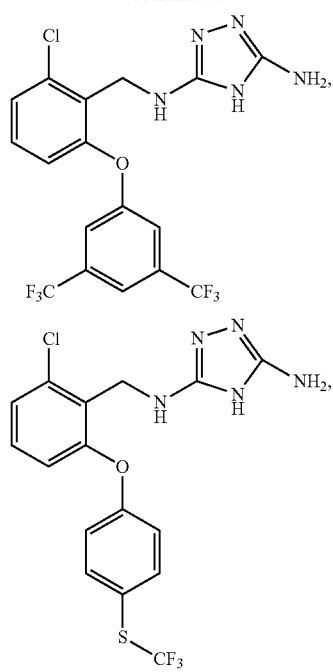
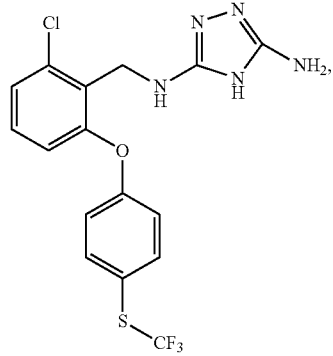
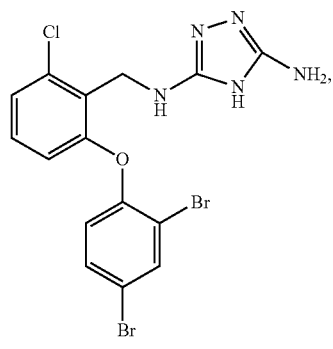
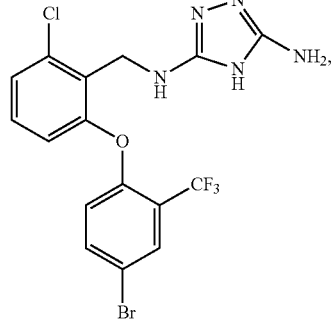
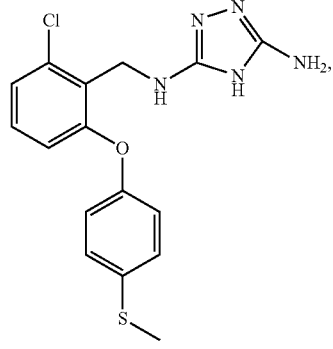
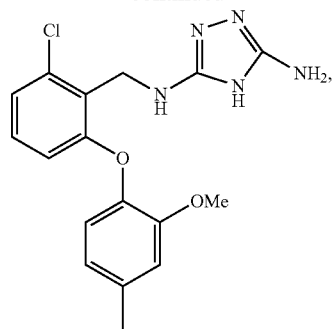
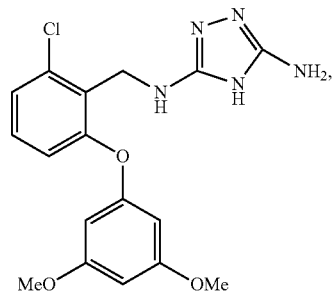
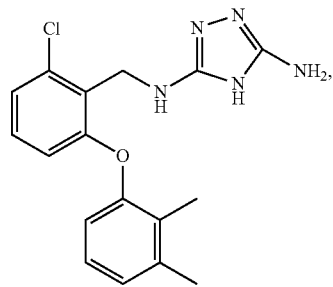
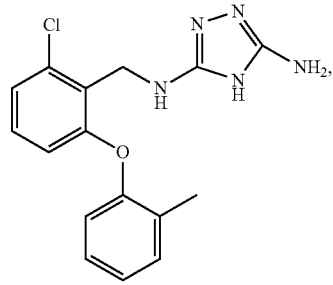
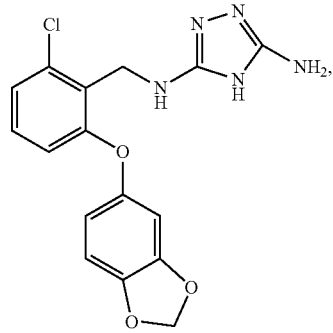

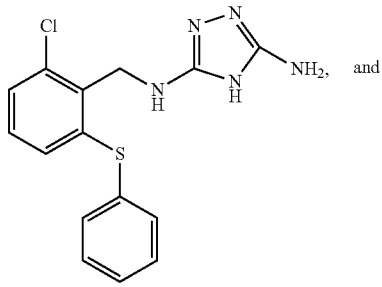 and
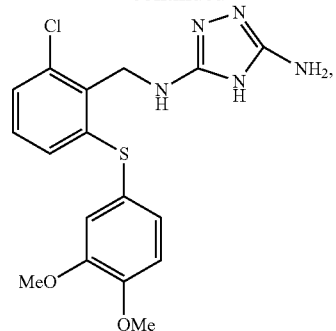
or a pharmaceutically acceptable salt or tautomer, thereof.
17. A method of preventing tissue damage related to ischemia or reperfusion injury comprising administering to a patient in need thereof a therapeutically effective amount of a compound of claim 1.
18. The method of claim 17, wherein the tissue is cardiac tissue.
* * * * *